United States Patent
Sinha et al.

(10) Patent No.: US 6,936,636 B2
(45) Date of Patent: Aug. 30, 2005

(54) 5-[PHENYL-TETRAHYDRONAPHTHALENE-2-YL DIHYDRONAPHTHALEN-2-YL AND HETEROARYL-CYCLOPROPYL]-PENTADIENOIC ACID DERIVATIVES HAVING SERUM GLUCOSE REDUCING ACTIVITY

(75) Inventors: Santosh Sinha, Irvine, CA (US); Kwok Yin Tsang, Irvine, CA (US); Smita Bhat, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/606,603

(22) Filed: Jun. 26, 2003

(65) Prior Publication Data

US 2005/0004213 A1 Jan. 6, 2005

(51) Int. Cl.$^7$ .............................................. A61K 31/19
(52) U.S. Cl. ...................... 514/557; 514/532; 514/529; 514/569; 514/561; 514/562; 514/568; 514/534; 560/38; 560/39; 560/10; 560/103; 560/104; 560/56; 562/466; 562/435; 562/492; 562/427; 562/493; 562/495
(58) Field of Search .............................. 560/56, 38, 39, 560/10, 103, 104; 562/466, 427, 435, 492, 493, 495; 514/532, 529, 557, 569, 561, 562, 568, 534

(56) References Cited

U.S. PATENT DOCUMENTS

| | | |
|---|---|---|
| 4,980,369 A | 12/1990 | Chandraratna |
| 5,015,658 A | 5/1991 | Chandraratna |
| 5,023,341 A | 6/1991 | Chandraratna |
| 5,455,265 A | 10/1995 | Chandraratna |
| 5,675,033 A | 10/1997 | Vuligonda et al. |
| 5,917,082 A | 6/1999 | Vuligonda et al. |
| 6,034,242 A | 3/2000 | Vuligonda et al. |
| 6,048,873 A | 4/2000 | Vasudevan et al. |
| 6,114,533 A | 9/2000 | Vuligonda et al. |
| 6,147,224 A | 11/2000 | Vuligonda et al. |
| 6,403,638 B1 | 6/2002 | Vuligonda et al. |

FOREIGN PATENT DOCUMENTS

WO  WO 93/11755  6/1993

OTHER PUBLICATIONS

Mangelsdorf et al. *The Retinoids Receptors In: The Retinoids.*, 1994, p. 319–349. Raven Press, Ltd., New York.
Dawson et al. *Chemistry and Biology of Synthetic Retinoids.*(1990) p. 324–363. CRC Press Inc.
Mukherjee et al. "Sensitization of Diabetic and Obese Mice to Insulin by Retinoid X Receptor Agonists", *Nature*, 1997, p. 407–410, vol. 386.
Feigner P.L. et al. (1989) "Cationic Lipsome–Mediated Transfection" *Focus,* 1989, p. 21–24, v.11–No. 2.
Heyman et al. "9–Cis Retinoic Acid Is a High Affinity Ligand for the Retinoid X Receptor" *Cell,* 1992, vol. 68, p. 397–406.
Allegretto et al. "Transactivation Properties of Retinoic Acid and Retinoid X Receptors in Mammalian Cells and Yeast" *J. Biol. Chem..* 1993, vol. 268, p. 26625–26633.
Cheng et al. Relationship Between the Inhibition Constant (K1) and the Concentration of Inhibitor which Causes 50 Per Cent Inhibition (I50) of an Enzymatic Reaction *Biolochemical Pharmacology,* 1973, vol. 22, p. 3099–3108.

*Primary Examiner*—Amelia A. Owens
(74) *Attorney, Agent, or Firm*—Gabor L. Szekeres

(57) ABSTRACT

Compounds of the formula:

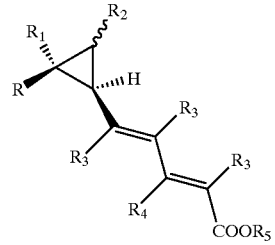

where the variables have the meaning defined in the specification are capable of reducing serum glucose levels in diabetic mammals without the undesirable side effects of reducing serum thyroxine levels and transiently increasing triglyceride levels.

42 Claims, No Drawings

5-[PHENYL-TETRAHYDRONAPHTHALENE-2-YL DIHYDRONAPHTHALEN-2-YL AND HETEROARYL-CYCLOPROPYL]-PENTADIENOIC ACID DERIVATIVES HAVING SERUM GLUCOSE REDUCING ACTIVITY

BACKGROUND OF THE INVENTION

Field of Invention

The present invention relates to compounds that have the property of reducing serum glucose and serum triglyceride levels in diabetic mammals without the undesirable properties of reducing serum thyroxine levels and transiently raising triglyceride levels. More particularly, the present invention relates to 5-[phenyl, tetrahydronaphthalene-2-yl dihydronaphthalen-2-yl and heteroaryl-cyclopropyl]-pentadienoic acid derivatives having the above-noted biological property.

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC. Press Inc., 1990, pages 324–356.

The following United States patents disclose compounds that include a pentadienoic acid moiety attached to a cyclopropyl group, with retinoid or like biological activity: U.S. Pat. Nos. 6,403,638; 6,147,224; 6,034,242; 6,048,873; 6,147,224; 5,917,082 and 5,675,033.

Relatively recently it has become known that certain retinoid compounds are capable of reducing serum glucose levels in diabetic mammals. Mukherjee, R.; Davies, P. J.; Crombie, D. L. Bishoff, E. D.; Cesario, R. M.; Jow Hamann, L. G.; Boehm, M. F.; Mondon, C. E.; Nadzan, A. M.; Paterniti, J. R. Jr.; Heyman, R. A. Sensitization of Diabetic and Obese Mice to Insulin by Retinoid X Receptor Agonists, *Nature* 1997, 386 (6623), 407–410. The compound (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid, described in U.S. Pat. No. 6,114,533, has this property. A disadvantage of the prior art retinoid compounds that reduce serum glucose levels is that their administration usually also results in the pharmacologically undesirable reduction of serum thyroxine levels and a transient increase in serum triglyceride levels. The present invention is directed to novel compounds which do not have these undesirable side effects.

SUMMARY OF THE INVENTION

The present invention relates to compounds of Formula 1

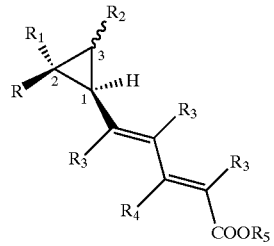

Formula 1 where a wavy line represents a bond in the up or in the down configuration, a dashed arrow represents a bond in the down configuration, a solid arrow represents a bond in the up configuration, $R_1$ is H, methyl, or ethyl, fluoro-substituted methyl or fluoro-substituted ethyl;

$R_2$ is normal alkyl of 1 to 4 carbons, fluoro-substituted normal alkyl of 1 to 4 carbons, $CH_2OCH_3$, $CH_2$—O—$CH_2$—$CH_3$, $CH_2$—O—$CH_2$—$OCH_3$, $CH_2$—$CH_2$—O—$CH_3$, $CH_2SCH_3$, $CH_2$—S—$CH_2$—$CH_3$, $CH_2$—S—$CH_2$—$OCH_3$, $CH_2$—$CH_2$—S—$CH_3$, $CH_2$—S—$CH_2$—S—$CH_3$, $CH_2$—O—$CH_2$—S—$CH_3$, $CH_2$—$NHCH_3$, $CH_2$—NH—$CH_2$—$CH_3$, $CH_2$—NH—$CH_2$—$OCH_3$, $CH_2$—$CH_2$—NH—$CH_3$, $CH_2$—O—$CH_2$—$NHCH_3$;

$R_3$ is H or F;

$R_4$ is H, alkyl of 1 to 3 carbons;

$R_5$ is H alkyl of 1 to 6 carbons, $OCH_2OR_6$ or $OCH_2OCOR_6$ where $R_6$ is alkyl of 1 to 3 carbons, and R is selected from the groups consisting of the radicals defined by formulas (a) through (f)

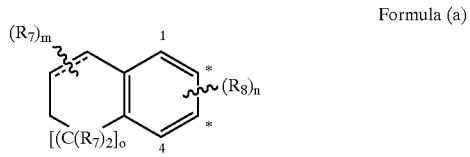

Formula (a)

-continued

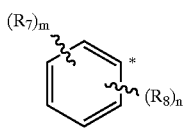
Formula (b)

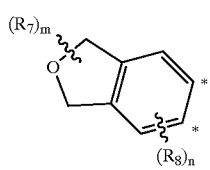
Formula (c)

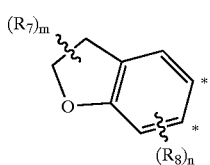
Formula (d)

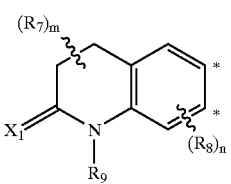
Formula (e)

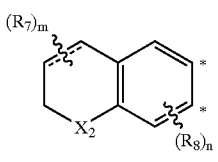
Formula (f)

where the dashed line in a ring represents a bond, or absence of a bond, a * denotes a ring carbon to which the pentadienoyl-cyclopropyl group is attached, with the proviso that the pentadienoyl-cyclopropyl group is attached to only one carbon on the ring;

$X_1$ is Q or S attached to the adjacent carbon with a double bond, or $X_1$ represents two hydrogens or $R_7$ groups attached to the adjacent carbon;

$X_2$ is O or S;

m is an integer having the values 0 to 6;

n is an integer having the values 0 to 3;

o is an integer having the values 0 or 1;

$R_7$ is independently H, alkyl of 1 to 6 carbons, F, Cl, Br or I;

$R_8$ is independently H alkyl of 1 to 6 carbons, F, Cl, Br, I, $OC_{1-6}$alkyl or $SC_{1-6}$alkyl, $R_9$ is H or alkyl of 1 to 6 carbons, or a pharmaceutically acceptable salt of said compound.

The present invention also relates to pharmaceutical compositions incorporating the compounds of Formula 1 and to methods of treatment of diabetic mammals with pharmaceutical compositions containing one or more corn pounds of Formula 1 to reduce serum glucose levels in said mammals.

The present invention also relates to the methods of using the compounds of the invention to treat diseases and conditions which are responsive to treatment by retinoids.

DETAILED DESCRIPTION OF THE INVENTION

General Embodiments and Synthetic Methodology

Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include olephinic double bonds about which trans and cis (E and Z) stereoisomerism can exist. The compounds of the present invention have the specific orientations of substituents relative to the double bonds as is indicated in the name of the respective compound, and/or by specific showing in the structural formula of the orientation of the substituents relative to the respective double bonds.

The compounds of the present invention also contain three or more chiral centers and therefore may exist in enantiomeric and diastereomeric forms.

With respect to carbons 1 and 2 of the cyclopropyl ring (numbering shown in Formula 1) all compounds of the invention have the orientation of substituents shown in Formula 1. With regard to other chiral centers in the compounds, the scope of the invention is intended to cover all possible orientations of the substituents, thus including pure enantiomers (optical isomers), diastereomers, mixtures of diastereomers and racemic mixtures of enantiomers.

Reaction Scheme 1 discloses a presently preferred general synthetic route to compounds of the invention where the variable R is a tetrahydronaphthalene derivative in accordance with Formula (a) and where the tetrahydronaphthalene is connected with its 2-position to the pentadienoyl-cyclopropyl group

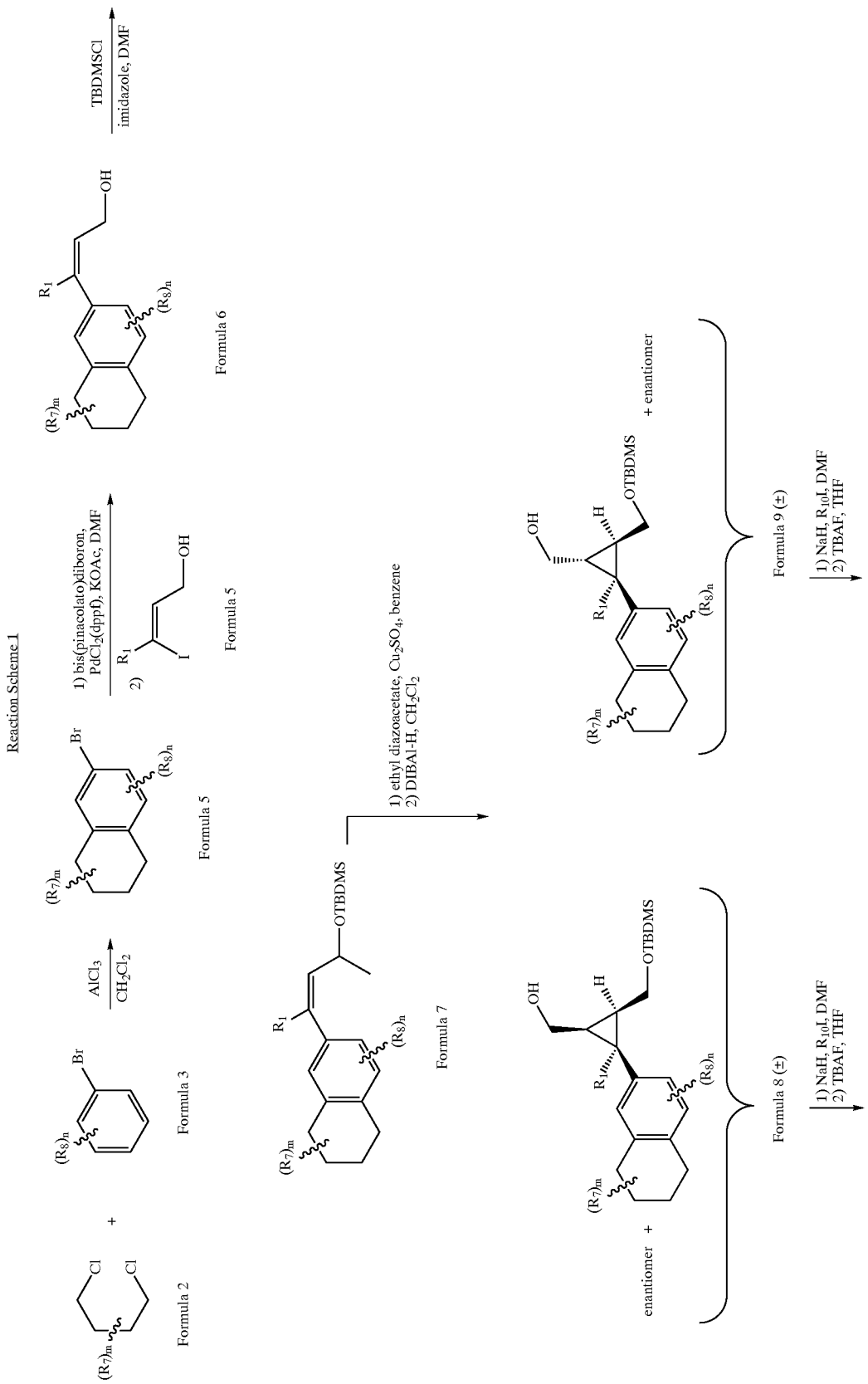
Reaction Scheme 1

-continued
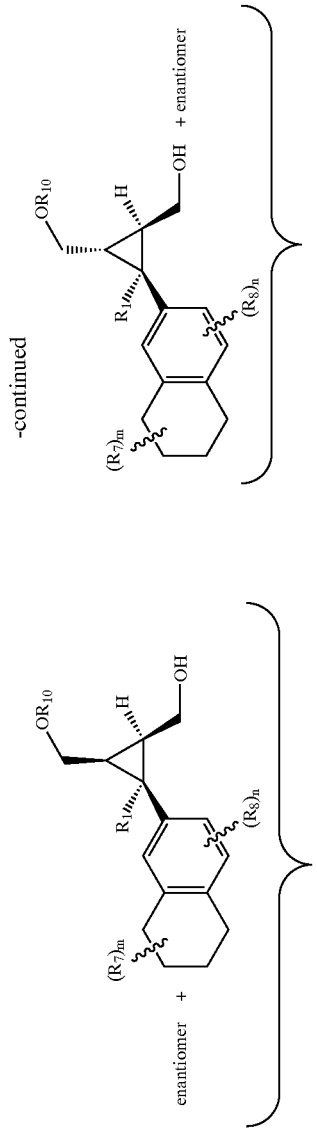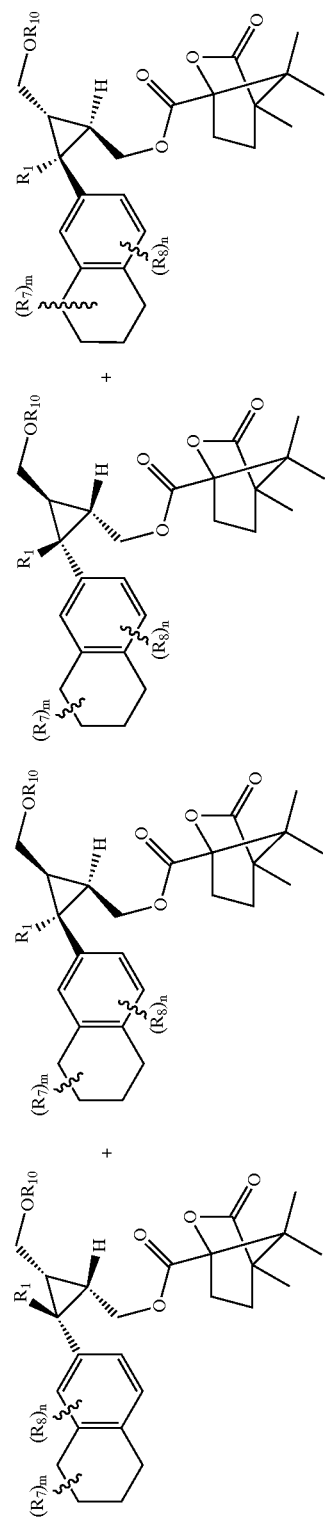

-continued

Although Reaction Scheme 1 is general, for the sake of easier exemplification and illustration the variable $R_3$ of Formula 1 is H in this scheme, the variable $R_4$ is methyl and the variable $R_2$ is $CH_2OR_{10}$, as in the preferred examples. Based on the present disclosure those skilled in the art would be able to employ state-of-the-art reactions to obtain compounds of the invention where $R_3$, $R_4$ and $R_2$ have the scopes defined in Formula 1.

Referring now to Reaction Scheme 1, one starting material is a dichloro substituted alkane compound of Formula 2 that already has the $R_7$ susbtituent or substituents. Another starting material is a bromobenzene derivative of Formula 3 that already has the $R_8$ substituent. The substitituted dichloro alkanes of Formula 2 and the substituted bromobenzenes of Formula 3 are either available commercially, or can be prepared in accordance with the chemical scientific and patent literature, or by such modifications of known synthetic procedures that are readily apparent to those skilled in the art. An example for the dichloro alkane derivative of Formula 2 that is utilized for the synthesis of several preferred compounds of the invention is 2,5-dichloro-2,5-dimethylhexane. Bromobenzene is used for the synthesis of several preferred compounds and serves as an example for the compounds of Formula 3. The compounds of Formula 2 and of Formula 3 are reacted under Friedel Crafts conditions to provide a substituted bromo-tetrahydronaphthalene derivative of Formula 4. The substituted bromo-tetrahydronaphthalene derivative of Formula 4 is reacted with a 3-iodo-alk-2Z-en-1-ol of Formula 5 in the presence of bis(pinacolato)diboron, potassium acetate and [1,1'-bis(diphenylphosphino)-ferrocene]dichloropalladium ($PdCl_2$(dppf)$_2$) in dimethylformamide (DMF) to give a 3-(5,6,7,8-tetrahydro-naphthalen-2-yl)-alk-2Z-en-1-ol compound of Formula 6. In Formula 5 $R_1$ is defined as in connection with Formula 1. An example for the reagent of Formula 5 that is utilized for the synthesis of several preferred compounds of the invention is 3-iodo-but-2Z-en-1-ol that can be obtained in accordance with the disclosure of U.S. Pat. No. 6,147,224, incorporated herein by reference.

The free hydroxyl group of the compound of Formula 6 is protected by treatment with tert-butyldimethylsilyl chloride (TBDMSCl) in the presence of imidazol; to give the tert-butyldimethyl-[3-(5,6,7,8-tetrahydronaphthalen-2-yl)-alk-2Z-enyloxy]silane compound of Formula 7. The compound of Formula 7 is then reacted with ethyl diazoacetate in an inert solvent, such as benzene, in the presence of anhydrous copper (II) sulfate, and the resulting carboxylic acid ester derivative is reduced to the primary alcohol level by treatment with di-iso-butyl aluminum hydride (DIBAl-H). A pair of diastereomeric cyclopropyl derivatives are the result of the latter reaction, with each diastereomer of the pair being present in a substantially racemic form, formed of two enantiomers. The diastereomers are shown as Formula 8 and Formula 9, respectively. It can be seen that the difference between the two diastereomers is in the configuration of the C-3 carbon of the cyclopropyl ring. Each of the diastereomers of Formula 8 and of Formula 9, respectively, is reacted with an alkylating agent of the formula $R_{10}I$ in the presence of strong base, such as sodium hydride, to introduce the $R_{10}$ group into the free primary hydroxyl function of the molecule. Thereafter the tert-butyldimethylsilyl protecting group is removed by treatment with tetrabutyl-ammonium fluoride (TBAF). The variable $R_{10}$ is defined in this connection as a radical that together with the $CH_2O$ group already attached to the C-3 carbon of the cyclopropyl ring would provide the $R_2$ radical defined in connection with Formula 1. Preferred examples for the reagent $R_{10}I$ are methyl or ethyl iodide. Instead of an iodo containing alkylating group other alkylating agents could also be used, and may become readily apparent to those skilled in the art in light of the present disclosure. The products of the alkylations and removal of the tert-butyldimethylsilyl protecting group are the diastereomeric racemates 3-alkoxymethyl-2-alkyl-2-(5,6,7,8-tetrahydro-naphthalen-2-yl)-cyclopropyl-methanols of Formulas 10 and 11, respectively.

The two diastereomers of Formulas 10 and 11, respectively are resolved into the corresponding pure enantiomers by treatment with 1-(S)-(−)-camphanic chloride and N,N-dimethylaminopyridine (DMAP) followed by high pressure liquid chromatography (UPLC) separation, of the resulting 1-(S)-(−)-camphanic esters of Formulas 12, 13 and of Formulas 14 and 15, respectively. After separation, each of the four compounds is saponified to remove the 1-(S)-(−)-camphanoyl group and the resulting primary alcohols are oxidized to the aldehyde level by treatment with tetrapropylammonium perruthenate (TPAP) in the presence of added molecular sieves and 4-methylmorpholine N-oxide (NMO). The resulting aldehydes are shown as compounds of Formulas 16, 17, 18 and 19. Each of the aldehydes is subjected to a Horner Emmons reaction with the reagent triethylphosphono-3-methyl-2E-butenoate (available from Aldrich) in the presence of strong base, such as n-butyl lithium and 1,3-dimethyl-3,4,5,6-tetrahydro-2(1H)-pyrimidinone (DMPU) in an aprotic solvent such as tetrahydrofuran (THF), to give the corresponding ethyl 5-[3-alkoxymethyl-2-alkyl-2-(-5,6,7,8-tetrahydro-naphthalen-2-yl)-cyclopropyl]-3-methyl-penta-2E,4E-dienoates of Fomulas 20, 21, 22 and 23. The compounds of Formulas 21 and 23 have the configuration at the C-1 and C-2 carbons of the cyclopropyl ring as shown in Formula 1, and are within the scope of the invention. These ester compounds are saponified by treatment with base, such as potassium hydroxide, to provide the free carboxylic acids or their salts, of the Formulas 24, 25, 26 and 27. The compounds of Formulas 25 and 27 have the configuration at the C-1 and C-2 carbons of the cyclopropyl ring as shown in Formula 1, and are within the scope of the invention.

Reaction Scheme 2 discloses a general synthetic route to compounds of the invention where the R group of Formula 1 is phenyl, as shown by Formula (b). Again, although Reaction Scheme 2 is general, for the sake of easier exemplification and illustration the variable $R_3$ of Formula 1 is H in this scheme, the variable $R_4$ is methyl and the variable $R_2$ is $CH_2OR_{10}$, as in the preferred examples. Based on the present disclosure those skilled in the art would be able to employ state-of-the-art reactions to obtain compounds of the invention where the $R_2$, $R_3$ and $R_4$ groups have the scopes defined in Formula 1.

Reaction Scheme 2
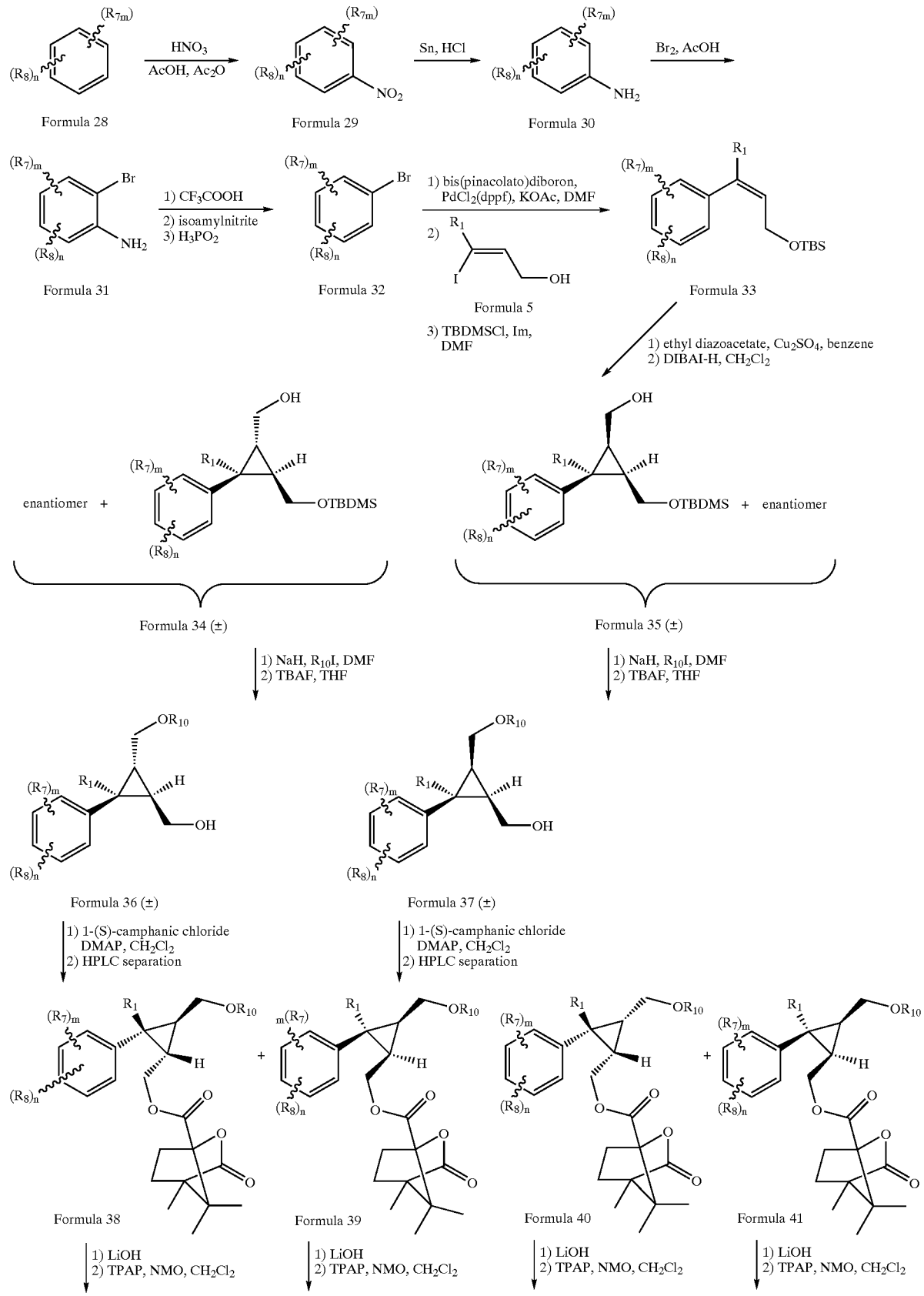

-continued

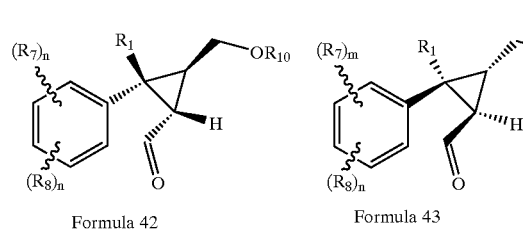

Formula 42    Formula 43    Formula 44    Formula 45

| Homer-Emmons Reaction | Homer-Emmons Reaction | Homer-Emmons Reaction | Homer-Emmons Reaction |

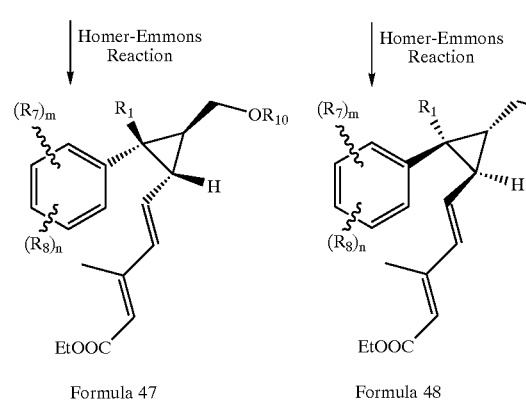

Formula 47    Formula 48    Formula 49    Formula 50

| KOH | KOH | KOH | KOH |

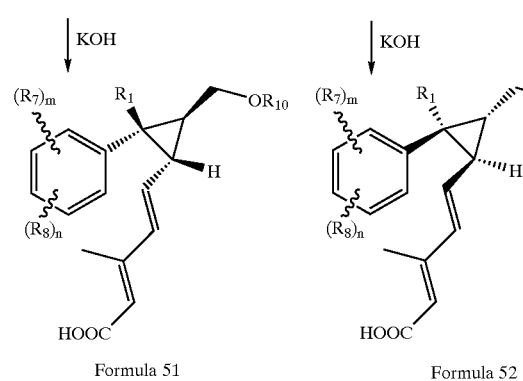

Formula 51    Formula 52    Formula 53    Formula 54

Referring now to Reaction Scheme 2, one starting material is a phenyl compound of Formula 28 that already has the $R_7$ and $R_8$ substituents. The substitituted phenyl compounds of Formula 28 are either available commercially, or can be prepared in accordance with the chemical scientific and patent literature, or by such modifications of known synthetic procedures that are readily apparent to those skilled in the art. An example for the phenyl compound of Formula 28 that is utilized for the synthesis of several preferred compounds of the invention is 1,3-di-iso-propylbenzene (available from Aldrich). A nitro group is introduced into the phenyl compound of Formula 28 by treatment with nitric acid in acetic acid and acetic anhydride and the resulting nitrophenyl compound of Formula 29 is reduced by treatment with mossey tin and hydrochloric acid to provide a substituted aniline compound of Formula 30. The substituted aniline compound of Formula 30 is brominated in acetic acid to provide the substituted bromo-aniline of Formula 31. The substituted bromo-aniline of Formula 31 is converted into a bromo-phenyl compound of Formula 32. Those skilled in the art will recognize that depending on the nature of the substituents $R_7$ and $R_8$, other synthetic routes may be available to obtain the bromo compound of Formula 32, or the bromo-phenyl compound of Formula 32 may be available commercially.

The bromo-phenyl compound of Formula 32 is then reacted with a 3-iodo-alk-2Z-en-1-ol of Formula 5 in the presence of bis(pinacolato)diboron, potassium acetate and [1,1'-bis(diphenylphosphino)-ferrocene]dichloropalladium ($PdCl_2(dppf)_2$) in dimethylformamide (DMF) to give a phenyl-alk-2Z-en-1-ol compound, the free hydroxyl group of which is protected by treatment with tert-butyldimethylsilyl chloride (TBDMSCl) in the presence of imidazol, to give the tert-butyldimethyl-[(phenyl)-alk-2Z-enyloxy]silane compound of Formula 33. An example for the reagent of Formula 5 that is utilized for the synthesis of several preferred compounds of the invention in the series where the R variable of Formula 1 is phenyl, is 3-iodo-but-2Z-en-1-ol.

The compound of Formula 33 is then reacted with ethyl diazoacetate in an inert solvent, such as benzene, in the presence of anhydrous copper (II) sulfate, and the resulting carboxylic acid ester derivative is reduced to the primary alcohol level by treatment with di-iso-butyl aluminum hydride (DIBAl-H). A pair of diastereomeric cyclopropyl derivatives are the result of the latter reaction, with each diastereomer of the pair being present in a substantially racemic form, formed of two enantiomers. The diastereomers are shown by Formula 34 and Formula 35, respectively. It can be seen that the difference between the two diastereomers is in the configuration of the C-3 carbon of the cyclopropyl ring.

Each of the diastereomers of Formula 34 and of Formula 35, respectively, is reacted with an alkylating agent of the formula $R_{10}I$ in the presence of strong base, such as sodium hydride, to introduce the $R_{10}$ group into the free primary hydroxyl function of the molecule. Thereafter the tert-butyldimethylsilyl protecting group is removed by treatment with tetrabutyl ammonium fluoride (TBAF). The variable $R_{10}$ is defined as in connection with Reaction Scheme 1. In this sequence of reaction also, the preferred examples for the reagent $R_{10}I$ are methyl or ethyl iodide. The products of the alkylations and removal of the tert-butyldimethylsilyl protecting group are the diastereomeric racemates 3-alkoxymethyl-2-alkyl-(phenyl)-cyclopropyl-methanols of Formulas 36 and 37, respectively.

The two diastereomers of Formulas 36 and 37, respectively, are resolved into the corresponding pure enantiomers, and the resolved primary alcohols are subjected to substantially the same sequence of reactions as shown and described in connection with Reaction Scheme 1, to give the ethyl [3-alkoxymethyl-2-methyl-2-(phenyl)-cyclopropyl]-3-methyl-penta-2E,4E-dienoates of Formulas 47, 48, 49 and 50. The compounds of Formulas 48 and 50 have the configuration at the C-1 and C-2 carbons of the cyclopropyl ring as shown in Formula 1, and are within the scope of the invention. These ester compounds are saponified by treatment with base, such as potassium hydroxide, to provide the free carboxylic acids or their salts, of the Formulas 51, 52, 53 and 54. The compounds of Formulas 52 and 54 have the configuration at the C-1 and C-2 carbons of the cyclopropyl ring as shown in Formula 1, and are within the scope of the invention.

Generally speaking, compounds of the invention where the variable R of Formula 1 is other than the examples specifically shown in Reaction Schemes 1 and 2 can be made by subjecting bromo-compounds analogous to the bromo compounds of Formulas 4 and 32 to the same sequence of reactions to which the bromo compounds of Formulas 4 and 32, are subjected to in Reaction Schemes 1 and 2, respectively. These bromo compounds can generally speaking be obtained in accordance with the chemical literature of by such modifications of known synthetic procedures which will become readily apparent to those skilled in the art in light of the present disclosure. Reaction Schemes 3 to 9 serve as examples how to obtain these bromo compounds.

Reaction Scheme 3 discloses a synthetic route to compounds of the invention which are indan derivatives, that is where the variable o of Formula (a) is zero and where the dashed line of formula (a) represents absence of a bond. For the sake of simplicity of illustration the scheme illustrates the synthesis of the compounds of the invention where the variable $(R_7)_m$ represent geminal dimethyl groups substituting carbons 5 and 7 of the indan nucleus. Thus, in accordance with this scheme 4-methyl-pent-3-en-2-one is reacted under Friedel Crafts conditions with a benzene derivative of Formula 55 to yield 4-phenyl-4,4-dimethyl-but-2-one derivative of Formula 56. The variables $R_8$ and m are defined as in connection with Formula 1. The 4-phenyl-4,4-dimethyl-but-2-one derivative of Formula 56 is then reacted with methylmagnesium bromide and thereafter cyclized by treatment with acid to yield the indan derivative of Formula 57. The indane derivative of Formula 57 is brominated with bromine in acetic acid to provide the bromo-indan derivative of Formula 58.

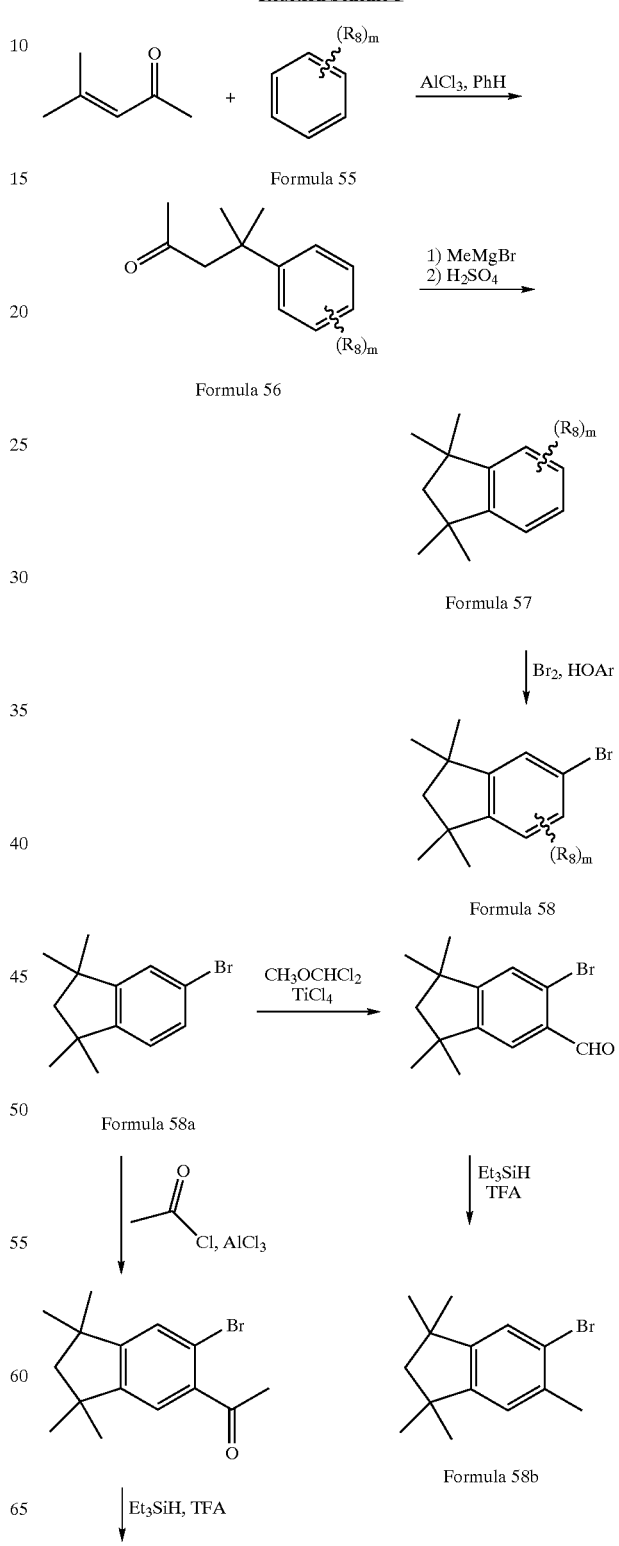

Reaction Scheme 3

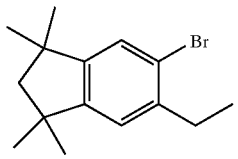

Formula 58c

The bromo-indan of Formula 58 is thereafter subjected to the same sequence of reactions (not shown in Scheme 3) as the bromo compounds of Formulas 4 and 32 of Reaction Schemes 1 and 2, respectively, to provide compounds of the invention in accordance with Formula 1 where the variable R is an indan radical. Reaction Scheme 3 also shows alternative routes whereby a methyl or ethyl subtituent corresponding to the variable $R_8$ can be introduced into the aromatic portion of the indan nucleus.

Reaction Scheme 4 discloses a synthetic route to compounds of the invention which are indene derivatives, that is where the variable o of Formula (a) is zero and where the dashed line of formula (a) represents a bond. For the sake of simplicity of illustration the scheme illustrates the synthesis of the compounds of the invention where the variable $(R_7)_m$ represent a geminal dimethyl groups substituting carbons 5 of the indene nucleus. Thus, in accordance with this scheme 3-methyl-but-2-en-oyl chloride (available from Aldrich) is reacted with 2-bromoanisol (available from Aldrich) under Friedel Crafts conditions to provide an acylated bromoanisole derivative of Formula 59. The compound of Formula 59 is then ring closed by treatment with polyphosphoric acid (PPA) to give the bromo-indanone derivative of Formula 60. The bromo-indanone of Formula 60 is reacted with a Grignard reagent $R_7MgX$ (where $R_7$ is defined as in connection with Formula 1 and X is halogen) and the resulting tertiary alcohol (not shown) is treated with acid such as para-toluenesulfonic acid (pTsOH) to provide the bromo indene derivative of Formula 61. The methyl group of the methoxy group of the compound of Formula 61 is removed by treatment with boron tribromide to give the hydroxy-bromoindene compound of Formula 62. The hydroxy-bromo-indene of Formula 62 is reacted with trifluoromethylsulfonic acid anhydride ($Tf_2O$) in pyridine (Py) to give the corresponding trifluoromethylsulfonate (triflate) of Formula 63. The triflate of Formula 63 is then reacted with formic acid in the presence of $PdCl_2(PPh_3)_2$ catalyst to give the bromoindene derivative of Formula 64. The compound of Formula 64 is subjected to the same sequence of reactions (not shown in Scheme 4) as the bromo compounds of Formulas 4 and 32 of Reaction Schemes 1 and 2, respectively, to provide compounds of the invention in accordance with Formula 1 where the variable R is an indene radical.

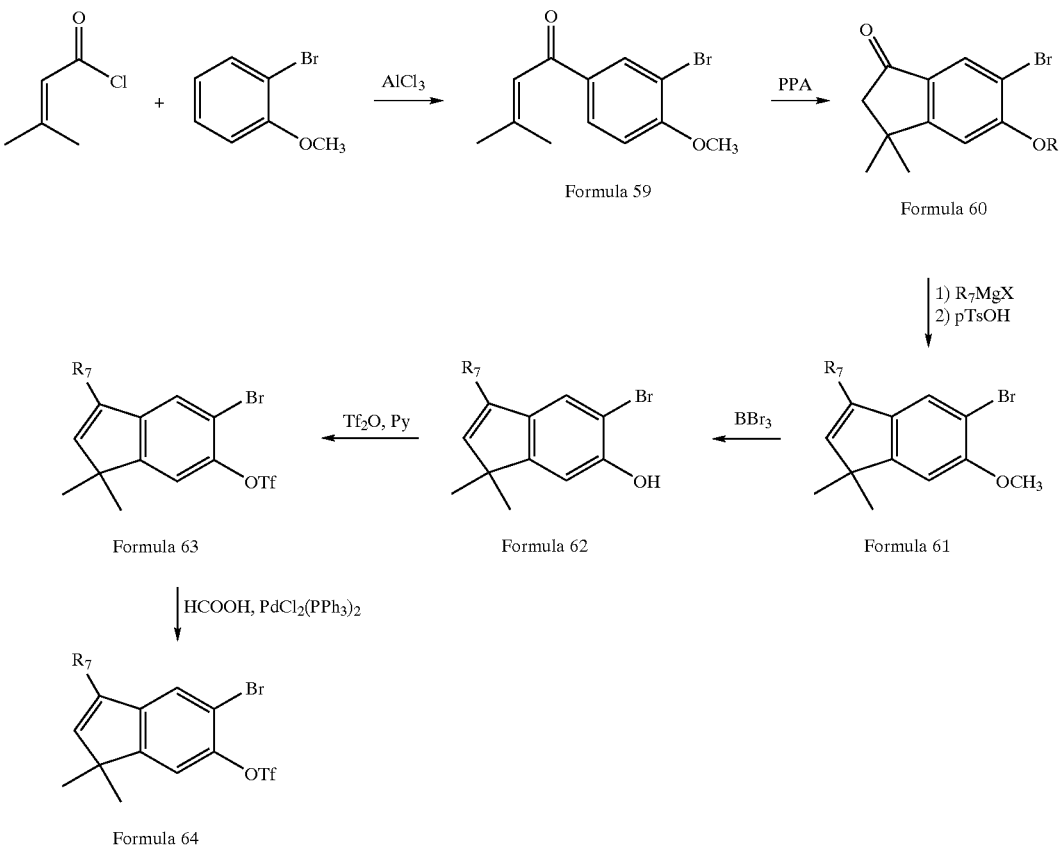

Reaction Scheme 4

Reaction Scheme 5 discloses a synthetic route to compounds of the invention which are tetrahydroquinoline or tetrahydroquinolinone derivatives, that is where the variable R of Formula 1 is represented by Formula (e). For the sake of simplicity of illustration, the scheme illustrates the synthesis of the compounds of the invention where the variable $(R_7)_m$ represents a geminal dimethyl groups substituting carbon 4 of the tetrahydroquinoline nucleus. Thus, in accordance with this scheme 4-bromoaniline is reacted with dimethyl-acryloyl chloride in the presence of triethylamine (TEA) to give the corresponding amide compound of Formula 65. The amide of Formula 65 is ring closed under Friedel Crafts conditions ($AlCl_3$) to give the 6-bromo-tetrahydroquinoline-2-one compound of Formula 66. The 6-bromo-tetrahydroquinoline-2-one compound of Formula 66 is reacted with borane ($BH_3$) to remove the keto group and provide the 6-bromoquinoline of Formula 67. Alternatively the 6-bromo-tetrahydroquinoline-2-one compound of Formula 66 alkylated on the nitrogen atom by treatment with an alkylating agent, such as $R_9I$ where $R_9$ is an alkyl group of 1 to 6 carbons, to give the compound of Formula 68. The keto function of the N-alkylated 6-bromo-tetrahydroquinoline-2; one compound of Formula 68 can also be removed by treatment with borane ($BH_3$) to provide N-alkylated 6-bromoquinoline compounds of Formula 69. The bromo compounds of Formulas 66, 67, 68 and 69 are subjected to the same sequence of reactions (not shown in Scheme 5) as the bromo compounds of Formulas 4 and 32 of Reaction Schemes 1 and 2, respectively, to provide compounds of the invention in accordance with Formula 1 where the variable R is a tetrahydroquinoline or tetrahydroquinolin-2-one radical.

Reaction Scheme 5

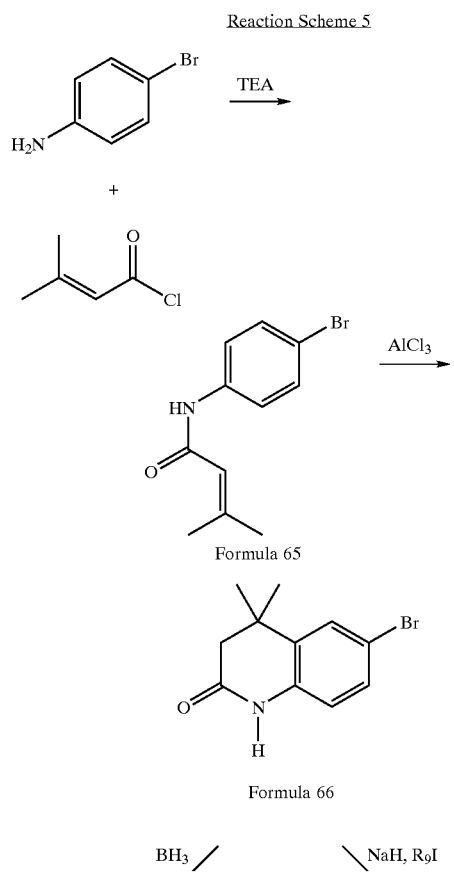

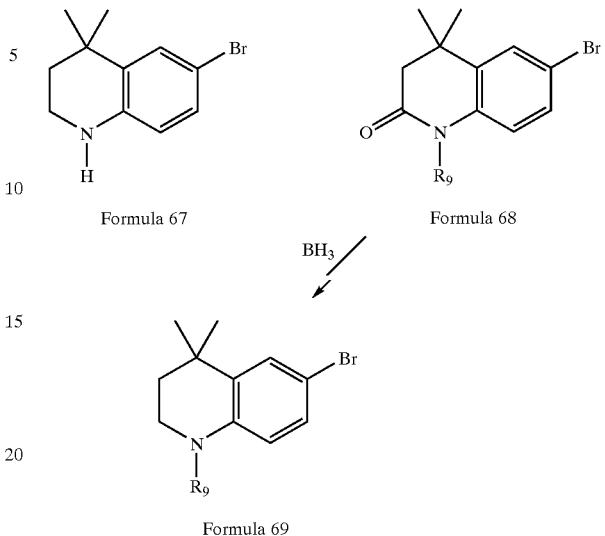

Reaction Scheme 6 discloses a synthetic route to compounds of the invention which are dihydronaphthalene derivatives, that is where the variable R of Formula 1 is represented by Formula (a) where the dashed line represents a bond and where the variable o represents the integer one (1). For the sake of simplicity of illustration the scheme illustrates the synthesis of the compounds of the invention where the variable $(R_7)_m$ represents geminal dimethyl groups substituting a carbon of the non-aromatic portion of the dihydronaphthalene nucleus. Thus, in accordance with this scheme, tetrahydronaphthalene-1-one (available from Aldrich) is brominated to provide 3-bromo-tetrahydronaphthalene-1-one. The keto function of 3-bromo-tetrahydronaphthalene-1-one is converted by treatment with dimethylzinc and titanium tetrachloride to geminal dimethyl groups, to give 1-bromo-3,3-dimethyl tetrahydronaphthalene. 1-Bromo-3,3-dimethyl tetrahydronaphthalene is oxidized by treatment with chromium trioxide in acetic acid to give 1-bromo-3,3-dimethyl-tetrahydronaphthalene-6-one. 1-Bromo-3,3-dimethyl-tetrahydronaphthalene-6-one is then reacted with a Grignard reagent of the formula $R_7MgX$ (where $R_7$ is defined as in connection with Formula 1 and X is halogen) to give the bromo-dihydronaphthalene derivative of Formula 70.

The bromo compound of Formula 70 is subjected to the same sequence of reactions (not shown in Scheme 6) as the bromo compounds of Formulas 4 and 32 of Reaction Schemes 1 and 2, respectively, to provide compounds of the invention in accordance with Formula 1 where the variable R is a dihydronaphthalene radical.

Reaction Scheme 6

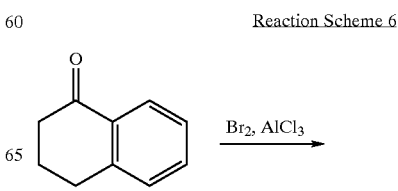

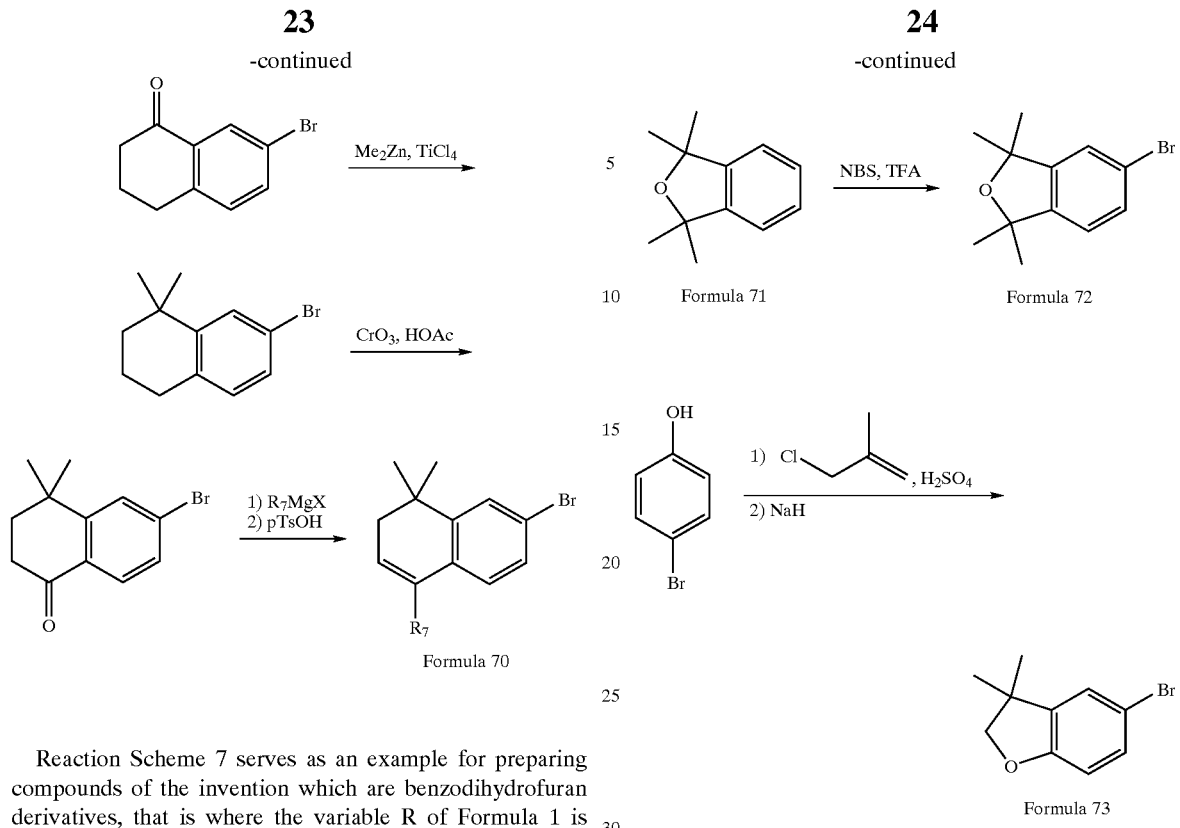

Reaction Scheme 7 serves as an example for preparing compounds of the invention which are benzodihydrofuran derivatives, that is where the variable R of Formula 1 is represented by Formula (c) or Formula (d). For the sake of simplicity of illustration the scheme illustrates the synthesis of the compounds of the invention where the variable $(R_7)_m$ represents geminal dimethyl groups substituting one or two carbons of the non-aromatic portion of the dihydrobenzofuran nucleus. Thus, in accordance with this scheme phtalic acid diethylester (available from Aldrich) is reacted methylmagnesium bromide and thereafter with acid to provide 2,2,7,7-tetramethyl-dihydro-iso-benzofuran of Formula 71. The dihydro-iso-benzofuran of Formula 71 is then reacted with N-bromosuccinimide (NBS) in tetrahydrofuran (THF) to give 4-bromo-2,2,7,7-tetramethyl-dihydro-iso-benzofuran of Formula 72.

In another exemplary sequence of reactions, 4-bromophenol is reacted with 3-chloro-2-methyl-prop-1-ene in the presence of strong acid ($H_2SO_4$), and thereafter with strong base (NaH) to provide 3,3-dimethyl-5-bromo-dihydrobenzofuran of Formula 73. The bromo compounds of Formulas 72 and 73 are subjected to the same sequence of reactions (not shown in Scheme 7) as the bromo compounds of Formulas 4 and 32 of Reaction Schemes 1 and 2, respectively, to provide compounds of the invention in accordance with Formula 1 where the variable R is dihydro-iso-benzofuran or dihydrobenzofuran radical.

Reaction Scheme 7

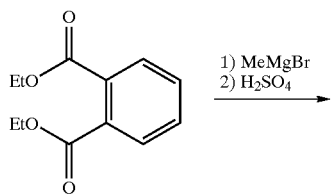

Reaction Scheme 8 serves as an example for preparing compounds of the invention which are chroman or thiochroman derivatives, that is where the variable R of Formula 1 is represented by Formula (f) and where the dashed line in the formula represents absence of a bond. For the sake of simplicity of illustration the scheme illustrates the synthesis of the compounds of the invention where the variable $(R_7)_m$ represents geminal dimethyl groups substituting carbons 2 and 4 of the non-aromatic portion of the chroman or thiochroman nucleus. A detailed description of preparing the 6-bromo thiochroman derivatives shown in Formulas 74 and 75 when $X_2$ is sulfur (S), through the reactions that are shown in Reaction Scheme 8 can be found in U.S. Pat. No. 4,980,369. U.S. Pat. No. 4,980,369 is expressly incorporated herein by reference. Analogous 6-bromo-4,4-dimethylthiochromans can be made in accordance with the teachings of U.S. Pat. Nos. 5,015,658 and 5,023,341, both of which are also incorporated herein by reference. The corresponding 6-bromo chroman derivatives shown in Formulas 74 and 75 when $X_2$ is oxygen (O) can be made by the reactions shown in the scheme. The bromo compounds of Formulas 74 and 75 are subjected to the same sequence of reactions (not shown in Scheme 7) as the bromo compounds of Formulas 4 and 32 of Reaction Schemes 1 and 2, respectively, to provide compounds of the invention in accordance with Formula 1 where the variable R is a chroman-2-one, thiochroman-2-one chroman or thiochroman radical.

Reaction Scheme 8

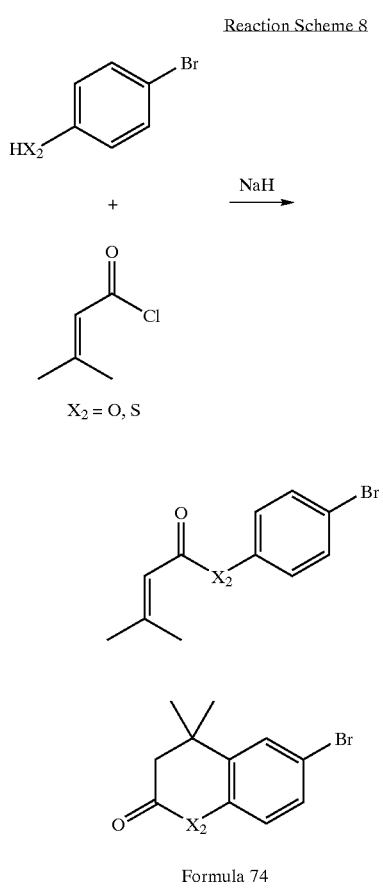

Formula 74

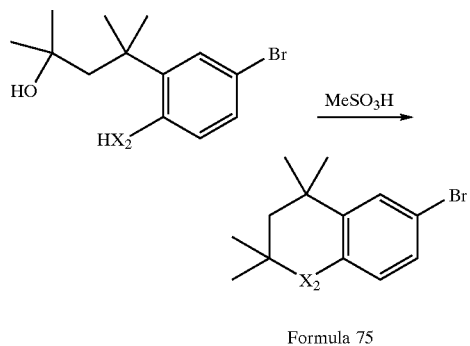

Formula 75

Reaction Scheme 9 provides examples for preparing compounds of the invention which are chromene or thiochromene derivatives, that is where the variable R of Formula 1 is represented by Formula (f) and where the dashed line represents presence of a bond. For the sake of simplicity of illustration the scheme illustrates the synthesis of the compounds of the invention where the variable $(R_7)_m$ represents geminal dimethyl groups substituting carbon 2 of the non-aromatic portion of the chromene or thiochromene nucleus. Thus, in accordance with this scheme, 4-bromophenol or 4-bromothiophenol is reacted with dimethylacryloyl chloride to provide the corresponding ester or thioester of Formula 76. The ester, or thioester of Formula 76 is then cyclized under Friedel Crafts conditions to provide the 7-bromo-thiochroman-4-one or the 7-bromo-chroman-4-one of Formula 77. The compound of Formula 77 is reacted with a Grignard reagent of the formula $R_7MgX$ (where X is halogen and $R_7$ is defined as in connection with Formula 1) and then with acid to provide the 7-bromo-2,2-dimethyl-thio-chromene or corresponding chromene derivative of Formula 78.

In another exemplary reaction sequence shown in Reaction Scheme 9, 4-bromophenol is reacted with acetyl chloride (AcCl) to provide the corresponding ester, and the ester made to undergo a Fries rearrangement under Friedel Crafts conditions to provide 2-acetyl-4-bromophenol. 2-Acetyl-4-bromnophenol is reacted with acetone in the presence of piperidine and trifluoroacetic acid (TFA) to give 6-bromo-2,2-dimethyl-chroman-4-one. The latter compound is reacted with the Grignard reagent of the formula $R_7MgX$ and then with acid to provide the 6-bromo-2,2-dimethyl-chromene derivative of Formula 79.

In still another exemplary reaction sequence shown in Reaction Scheme 9 4-bromo-thiophenol is reacted with 2,2-dimethylacryloic acid in the presence of piperidine to provide an adduct of Formula 80 that is cyclized by treatment with methylsulfonic acid to give 6-bromo-2,2-dimethyl-thiochroman-4-one of Formula 81. The compound of Formula 81 is reacted with the Grignard reagent of the formula $R_7MgX$ and then with acid to provide the 6-bromo-2,2-dimethyl-thiochromene derivative of Formula 82.

The bromo compounds of Formulas 78, 79 and 82 are subjected to, the same sequence of reactions (not shown in Scheme 9) as the bromo compounds of Formulas 4 and 32 of Reaction Schemes 1 and 2, respectively, to provide compounds of the invention in accordance with Formula 1 where the variable R is a chromene or a thiochromene radical.

Reaction Scheme 9

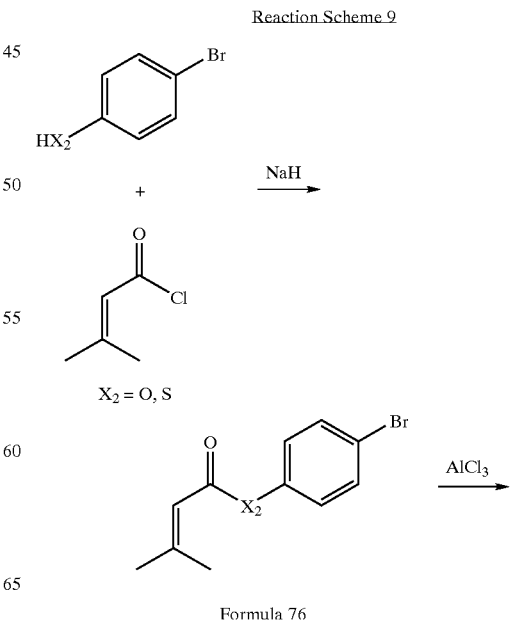

Formula 76

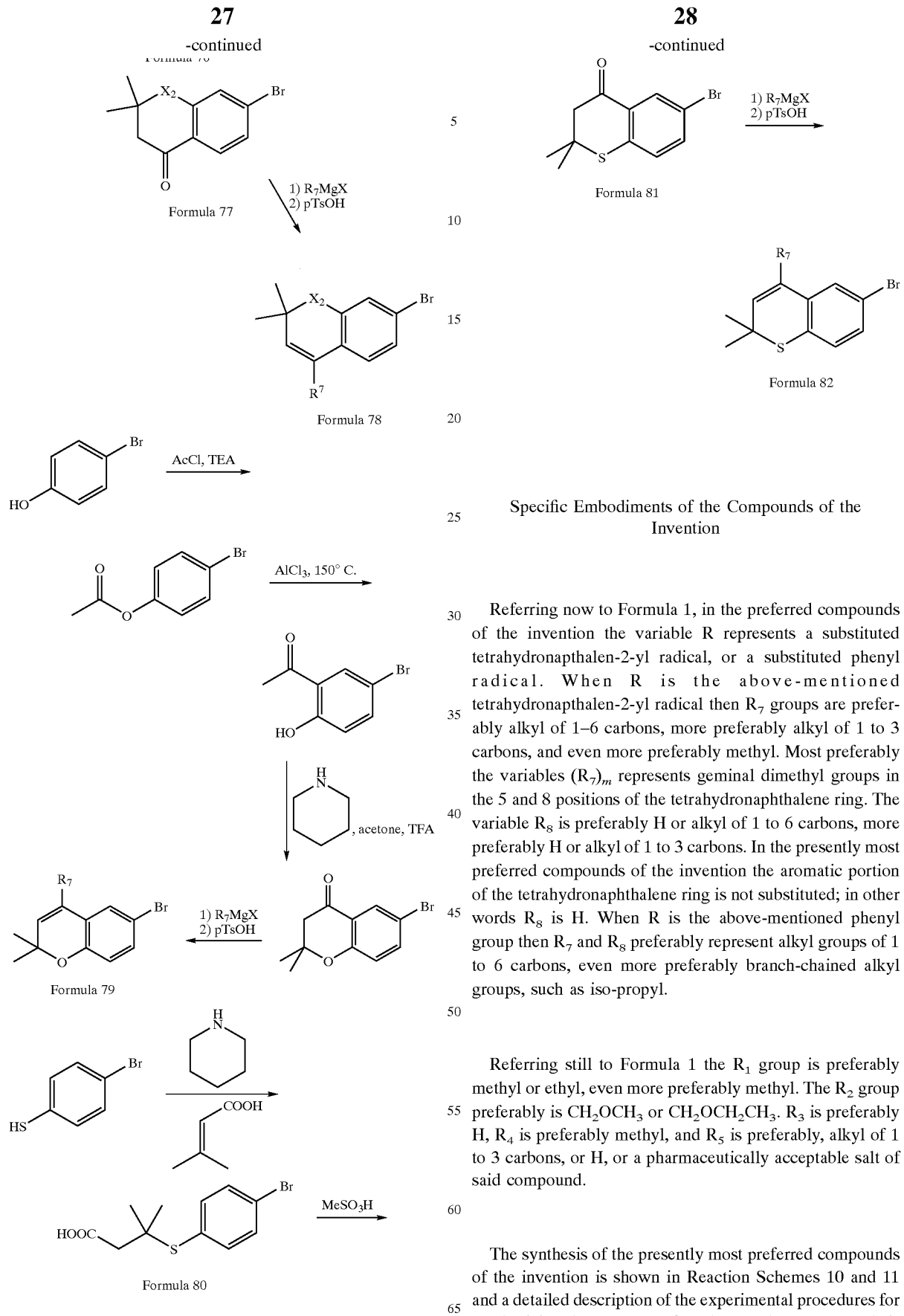

Specific Embodiments of the Compounds of the Invention

Referring now to Formula 1, in the preferred compounds of the invention the variable R represents a substituted tetrahydronapthalen-2-yl radical, or a substituted phenyl radical. When R is the above-mentioned tetrahydronapthalen-2-yl radical then $R_7$ groups are preferably alkyl of 1–6 carbons, more preferably alkyl of 1 to 3 carbons, and even more preferably methyl. Most preferably the variables $(R_7)_m$ represents geminal dimethyl groups in the 5 and 8 positions of the tetrahydronaphthalene ring. The variable $R_8$ is preferably H or alkyl of 1 to 6 carbons, more preferably H or alkyl of 1 to 3 carbons. In the presently most preferred compounds of the invention the aromatic portion of the tetrahydronaphthalene ring is not substituted; in other words $R_8$ is H. When R is the above-mentioned phenyl group then $R_7$ and $R_8$ preferably represent alkyl groups of 1 to 6 carbons, even more preferably branch-chained alkyl groups, such as iso-propyl.

Referring still to Formula 1 the $R_1$ group is preferably methyl or ethyl, even more preferably methyl. The $R_2$ group preferably is $CH_2OCH_3$ or $CH_2OCH_2CH_3$. $R_3$ is preferably H, $R_4$ is preferably methyl, and $R_5$ is preferably, alkyl of 1 to 3 carbons, or H, or a pharmaceutically acceptable salt of said compound.

The synthesis of the presently most preferred compounds of the invention is shown in Reaction Schemes 10 and 11 and a detailed description of the experimental procedures for synthesizing these most preferred exemplary compounds is also provided below.

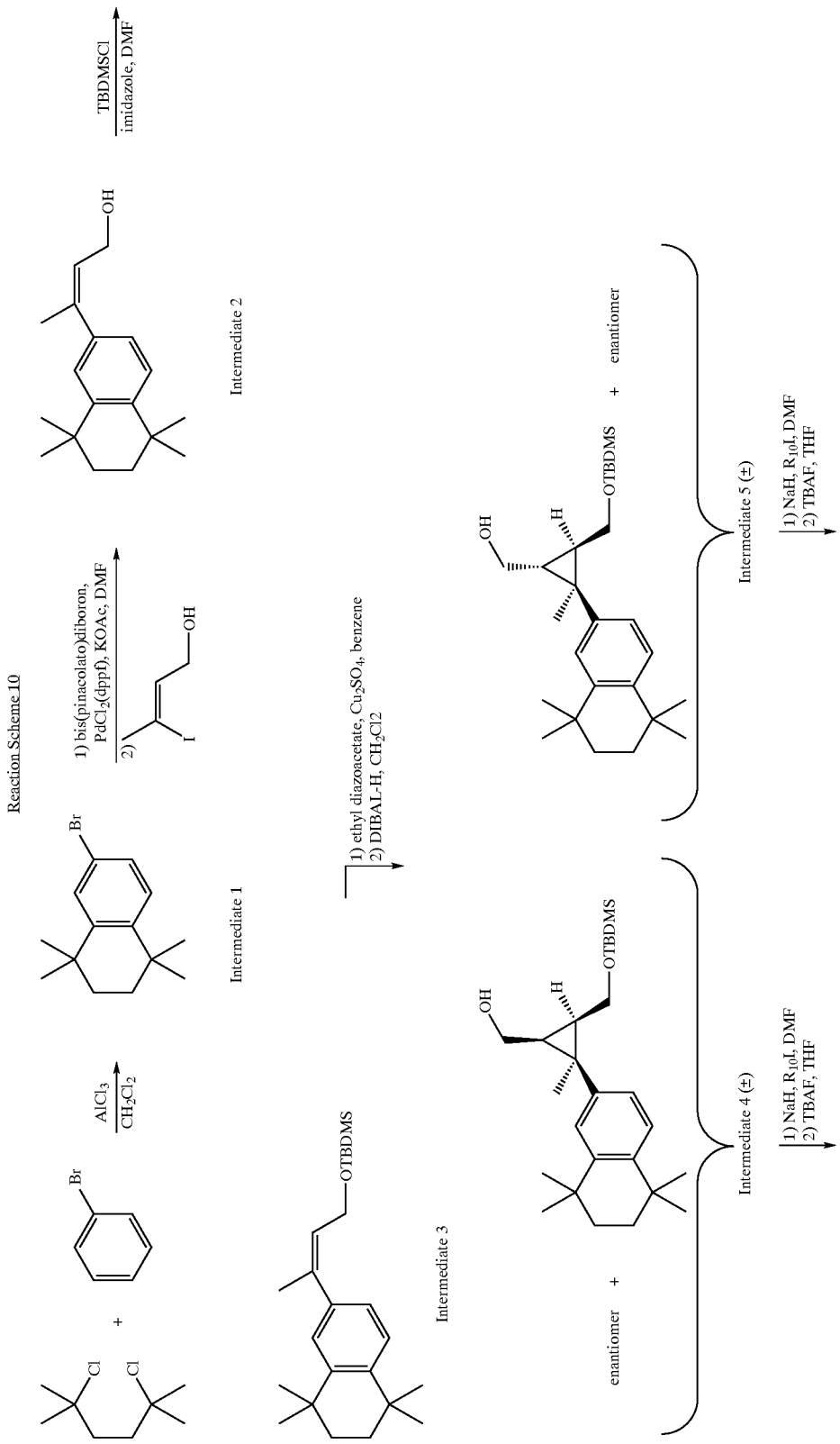

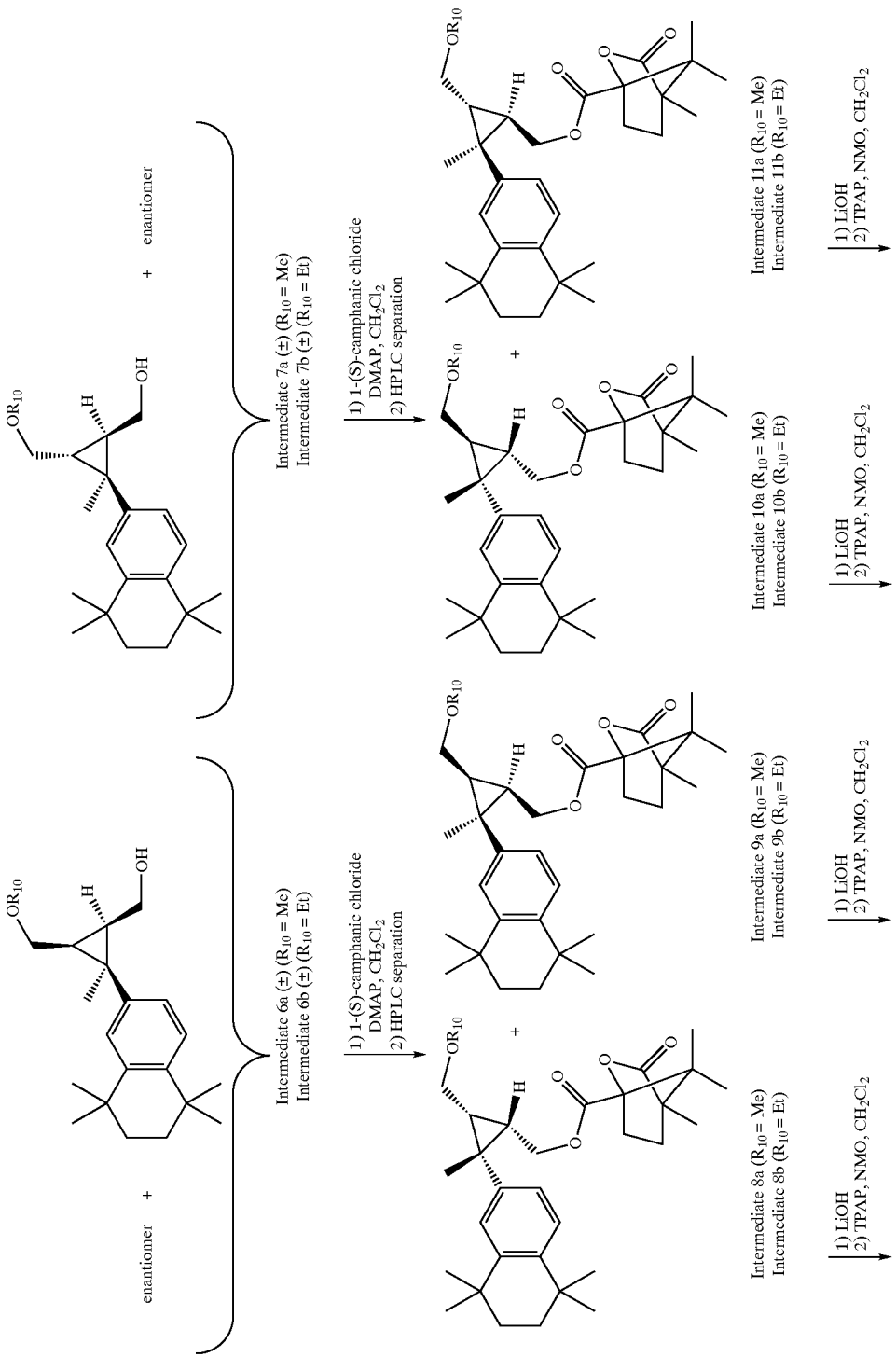

-continued
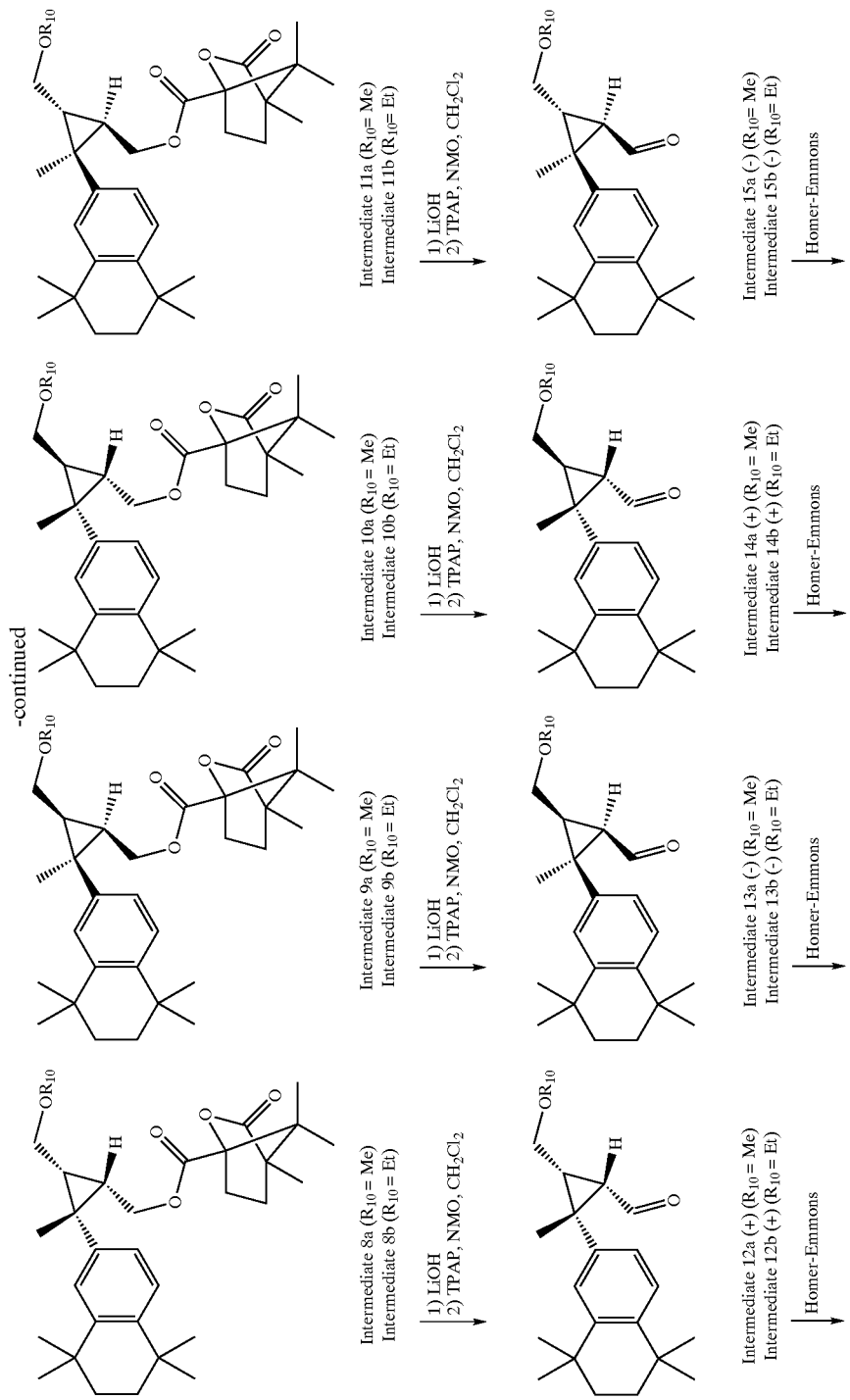

-continued
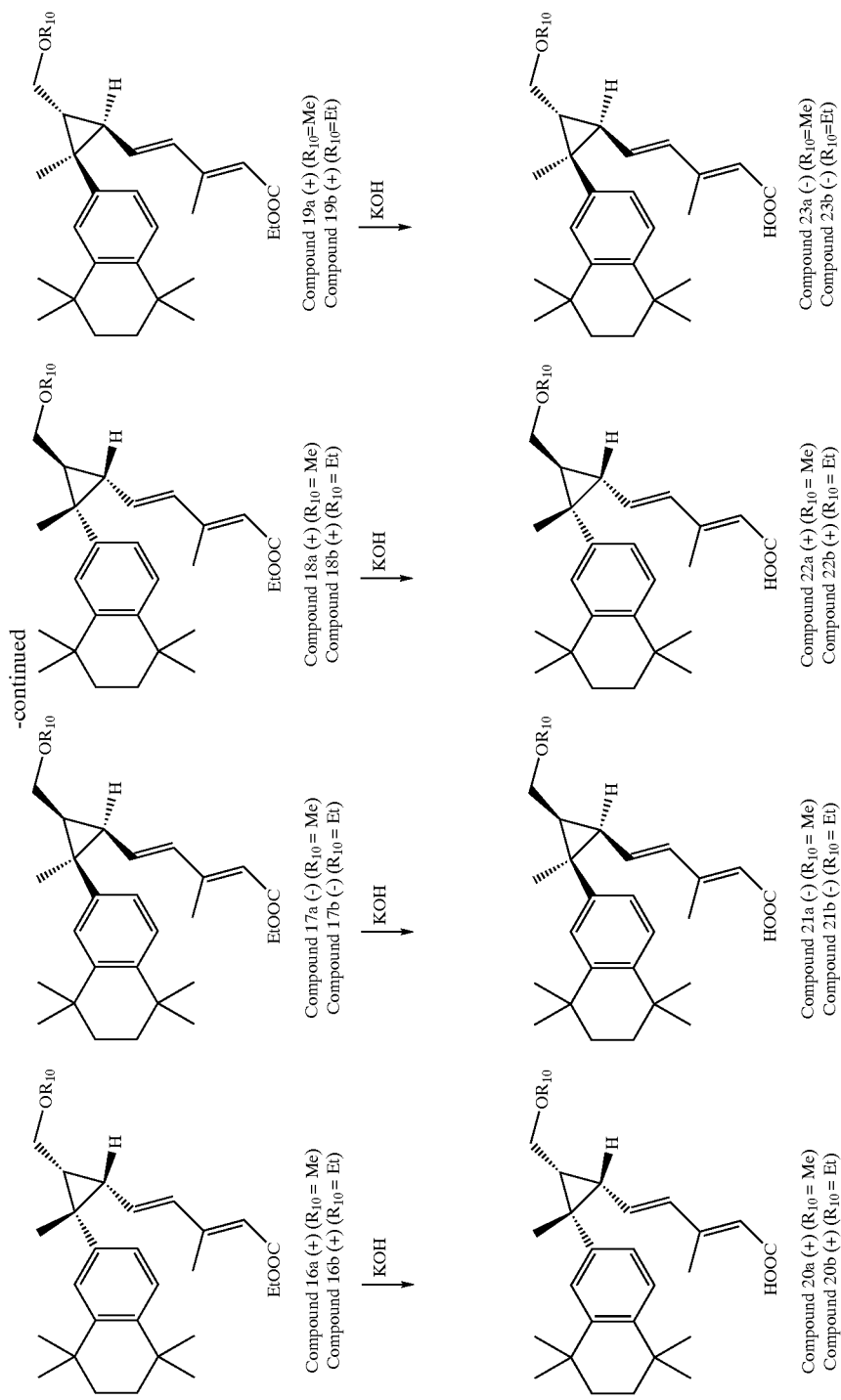

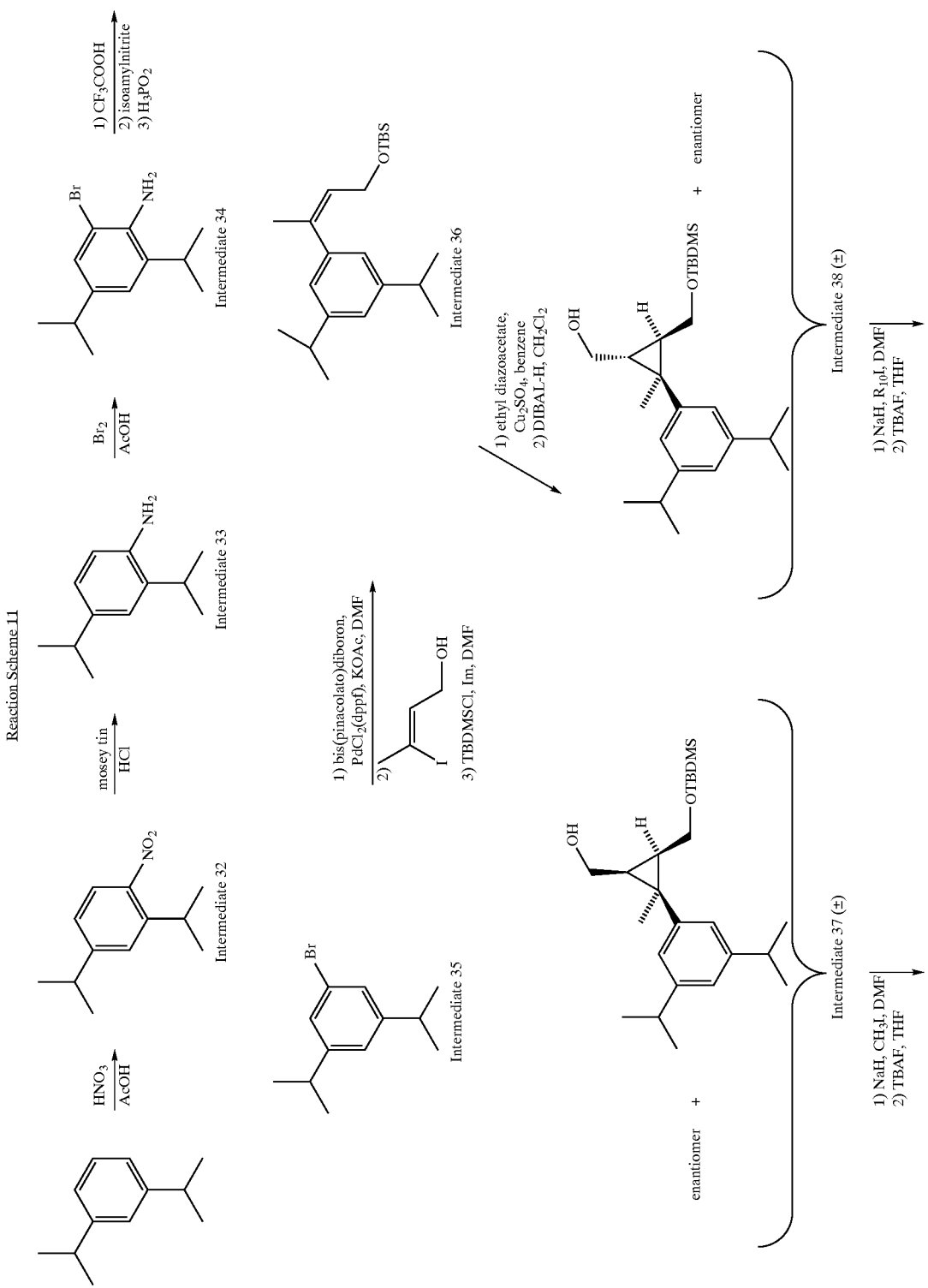

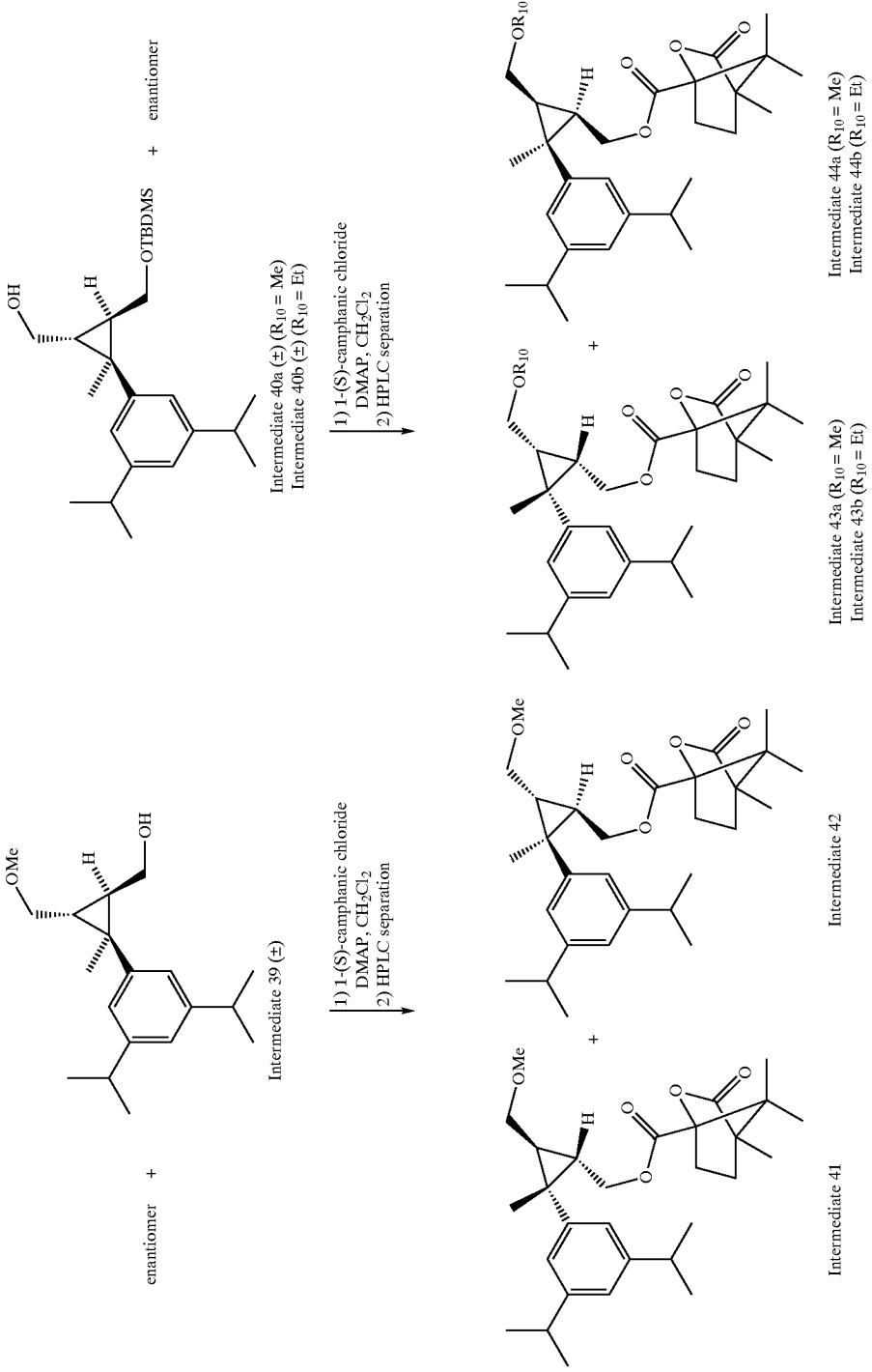

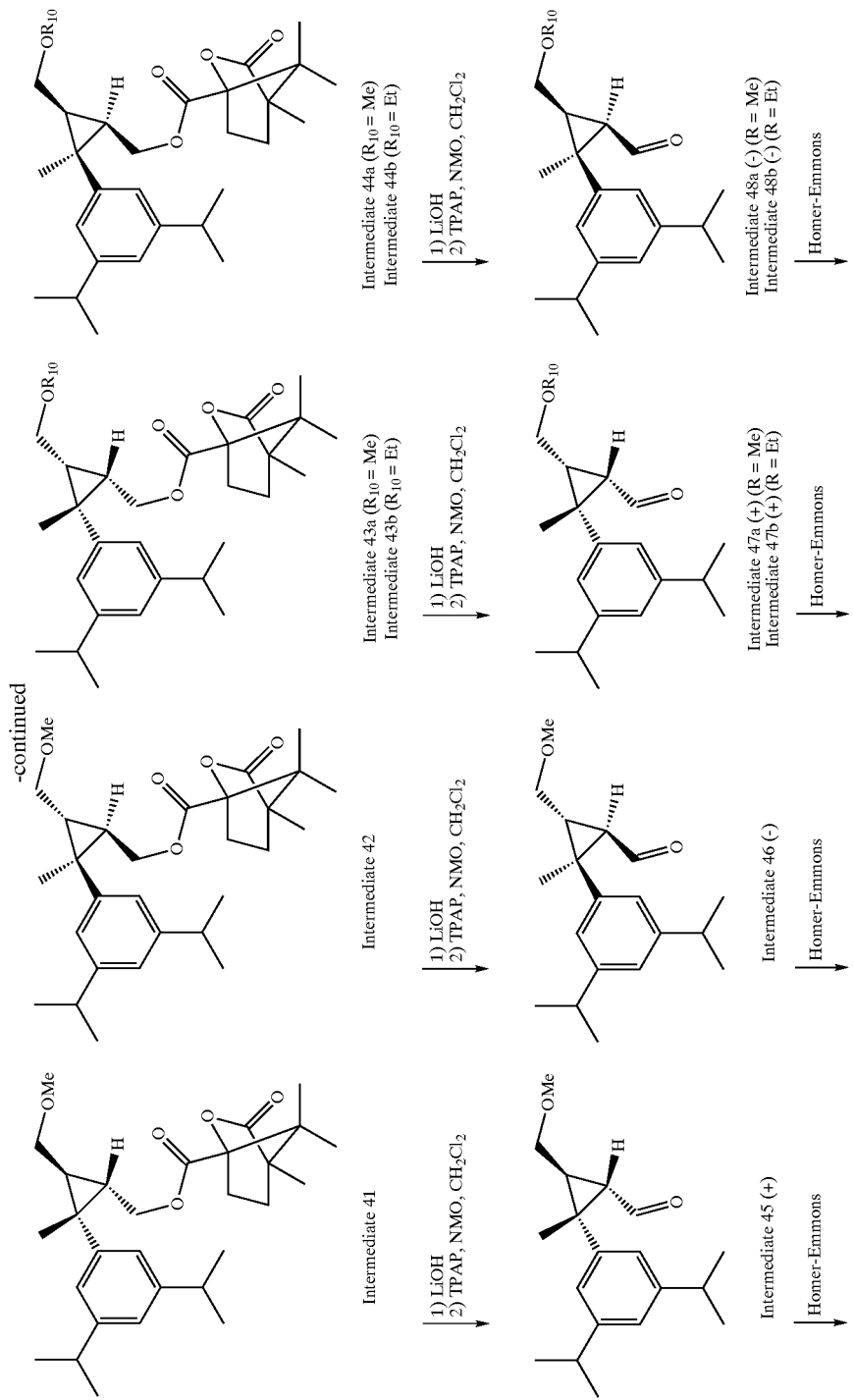

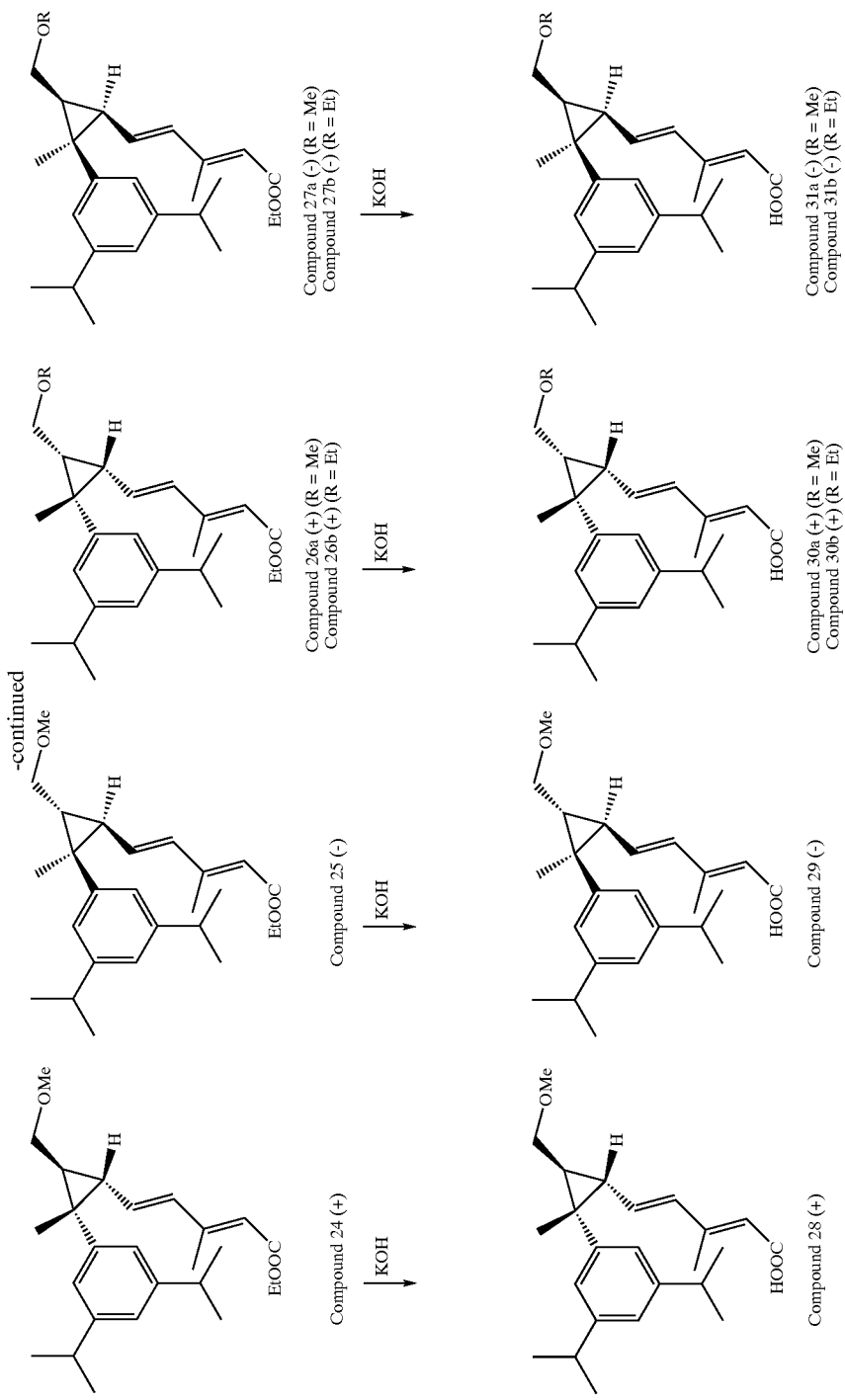

Experimental Procedures For Synthesizing the Exemplary Compounds of the Invention 6-Bromo-1,1,4,4-tetramethyl-1,2,3,4-tetrahydronaphthalene (Intermediate 1)

Aluminum chloride (700 mg, 5.25 mmol) was added slowly to a solution of 2,5-dichloro-2,5-dimethylhexane (11 g, 60 mmol) in bromobenzene (90 mL) at 0° C. After stirred for 20 min, the mixture was diluted with 100 mL of ether:hexane (1:1), washed with ice-water (1×10 mL), 10% HCl (1×10 mL) and brine (1×10 mL), dried (MgSO$_4$) and concentrated to afford a brown oil. The crude was then distilled using Coughler distillation to yield the title compound (13.2 g, 83% yield) as a white solid:

$^1$HNMR (CDCl$_3$, 300 MHz) δ 7.39 (d, J=2.0 Hz, 1H), 7.22, (dd, J=2.0 Hz., 8.1 Hz, 1H), 7.16(d, J=8.1 Hz, 1H), 1.66 (s, 4H), 1.25 (s, 6H).

3-(5,5,8,8-Tetramethyl-5,6,7,8-tetrahydro-naphthalen-2-yl)-but-2Z-en-1-ol (Intermediate 2)

Bis(pinacolato)diboron (5.8 g, 22.5 mmol), potassium acetate (4.5 g, 45 mmol) and [1,1'-bis(diphenylphosphino)-ferrocene]dichloropalladium (PdCl$_2$(dppf)$_2$) (500 mg, 0.6 mmol) were added to a solution of Intermediate 1 (4 g, 15 mmol) in 50 mL of DMF under argon. The mixture was then stirred at 80° C. for 24 h. After cooling to room temperature, 3-iodo-but-2Z-en-1-ol (6 g, 30 mmol), 2M Na$_2$CO$_3$ (30 ml), and PdCl$_2$(dppf)$_2$ (500 mg, 0.6 mmol) were added to the mixture, which was then stirred at 80° C. for another 24 h. The reaction was finally quenched with water (20 mL) and extracted with ether (3×10 mL). The organic layer was washed with brine (2×10 mL), dried (MgSO$_4$) and concentrated to give a crude brown oil. The crude product was purified by flash chromatography using 20% EtOAc in hexane to give the title compound (3 g, 77% yield) as a colorless oil:

$^1$HNMR (CDCl$_3$, 300 MHz) δ 7.26 (d, J=8.1 Hz, 1H), 7.09 (d, J=1.8 Hz, 11), 6.96 (dd, J=1.8 Hz, 8.1 Hz, 1H), 5.69 (t, J=6.3 Hz, 1H), 4.14 (d, J=6.3 Hz, 2H), 2.24 (s, 3H), 1.70 (s, 4H), 1.31 (s, 6H), 1.28 (s, 6H).

tert-Butyldimethyl-[3-(5,5,8,8-tetramethyl-5,6,7,8-tetrahydronaphthalen-2-yl)-but-2Z-enyloxy]silane (Intermediate 3)

tert-Butyldimethylsilyl chloride (2.7 g, 17.5 mmol) was added to the solution of Intermediate 2 (3 g, 11.6 mmol) and imidazole (1.6 g, 23.2 mmol) in 10 mL of DMF. The mixture was then stirred for 16 h at room temperature. After quenching with water, the mixture was extracted with ether (3×10 mL), washed with brine (1×10 mL), dried (MgSO$_4$) and concentrated to give a crude brown oil. The crude product was purified by flash chromatography using 10% EtOAc in hexane to give the title compound (3 g, 70% yield) as a colorless oil:

$^1$HNMR (CDCl$_3$, 300 MHz) δ 7.23 (d, J=8.1 Hz, 1H), 7.15 (d, J=1.8 Hz, 1H), 6.96 (dd, J=1.8 Hz, 8.1 Hz, 1H), 5.63 (t, J=6.3 Hz, 1H), 4.16 (d, J=6.3 Hz, 2H), 2.21 (s, 3H), 1.70 (s, 4H), 1.29 (s, 6H), 1.28 (s, 6H), 0.86 (s, 9H), 0.00 (s, 6H).

(±)-[(S)-3-(tert-Butyldimethylsilanyloymethyl)-2-methyl-2-(5,5,8,8-tetramethyl-5,6,7,8-tetrahydro-naphthalen-2-yl)-cyclopropyl]-methanol (Intermediate 4) and (±)-[(R)-3-(tert-butyl-dimethylsilanyloxymethyl)-2-methyl-2-(5,5,8,8-tetramethyl-5,6,7,8-tetrahydro-naphthalen-2-yl)-cyclopropyl]-methanol (Intermediate 5)

Ethyl diazoacetate (4.5 mL, 42 mmol) in 10 mL of benzene was added slowly with a syringe pump (2 ml/h) to a solution of Intermediate 3 (0.7 g, 1.9 mmol) and anhydrous copper (II) sulfate (60 mg, 376 μmol) in 30 mL of benzene (30 mL) at 80° C. After the addition of ethyl diazoacetate has been completed, the mixture was allowed to stir for 16 h at room temperature in order to decompose the excess of ethyl diazoacetate. The solvent was then evaporated under reduced pressure and the residue was purified by flash chromatography using 2% EtOAc in hexane to yield 1.6 g of a mixture of crude cyclopropyl esters, which were then dissolved in 15 mL of anhydrous THF and cooled to –78° C. with a dry ice/acetone bath. To this solution was added DIBAL-H in hexane (1M, 11 mL, 11 mmol) After stirring at –78° C. for 2 h, the reaction was quenched with saturated NH$_4$Cl (4 mL). Celite (4 g) and ether (50 mL) were then added to the mixture and stirring was continued at 0° C. until all aluminum salt precipitated out. Inorganic material was removed by filtration, and the solvents were removed under reduced pressure to give a brown oil, which was purified by flash chromatography using 20% EtOAc in hexane to give the title compounds, Intermediate 4 (232 mg, 29% yield) and Intermediate 5 (155 mg. 20% yield) as colorless oils $^1$HNMR for Intermediate 4: (CDCl$_3$, 300 MHz) δ 7.11 (d, J=4.8 Hz, 1H), 6.84 (d, J=0.9 Hz, 1H) 6.70 (dd, J=3.3 Hz, 6.9 Hz, 1H), 4.08 (dd, J=3.3 Hz, 6.9 Hz, 1H), 3.87–3.92 (m, 1H), 3.10–3.19 (m, 2H), 1.6 (s, 4H), 1.40–1.45 (m, 1H) 1.19–1.28 (m, 16H), 0.82 (s, 9H), 0.00 (d, J=15.6 Hz, 6H);

$^1$HNMR for Intermediate 5: (CDCl$_3$, 500 MHz) δ 7.26 (d, J=8.5 Hz, 1H), 7.24 (d, J=2.0 Hz, 1H), 7.12 (dd, J=2.0 Hz, 8.5 Hz, 1H), 3.87–3.89 (m, 2H), 3.48 (dd, J=7.0 Hz, 11.0 Hz, 1H), 3.17 (dd, J=7.0 Hz, 11.0 Hz, 1H, 1.73 (s, 3H), 1.46–1.47 (m, 5H), 1.33–1.34 (m,12H), 1.29 (q, J=7.5 Hz, 1H), 0.91 (s, 9H), 0.19 (d, J=9.5 Hz, 6H), (±)-[(S)-3-Methoxymethyl-2-methyl-2-(5,5,8,8-tetramethyl-5,6,7,8-tetrahydronaphthalen-2-yl)-cyclopropyl]-methanol (Intermediate 6a)

Sodium hydride (67 mg, 1.68 mmol) was added slowly to a solution of Intermediate 4 (232 mg, 0.56 mmol) in 5 mL of DMF at 0° C. After stirring for 10 min., methyl iodide (0.103 mL, 1.68 mmol) was added to the mixture, which was then stirred at room temperature for 16 h. The reaction was quenched with saturated NH$_4$Cl, extracted with ether (3×10 mL), washed with brine (1×10 mL), dried (Na$_2$SO$_4$) and concentrated to give a crude brown oil. Purification by flash chromatography using 5% EtOAc in hexane afforded the methoxy intermediate still protected with a tert-butyldimethylsilanyl group (194 mg, 78% yield) as a colorless oil. This: colorless oil was then dissolved in 5 mL of anhydrous THF and cooled to 0° C. with an ice bath. To this solution was added TBAF in THF (1M, 0.7 mL, 0.7 mmol) and the reaction mixture was allowed to stir at room temperature for 2 h. The reaction was finally quenched with water, extracted with ether (3×10 mL), washed with brine; (1×10 mL), dried (Na$_2$SO$_4$) and concentrated to give a crude colorless oil. Purification by flash chromatography using 20% EtOAc in hexane gave the title compound (100 mg, 54% yield) as a colorless oil:

$^1$HNMR (CDCl$_3$, 500 MHz) δ 7.17 (d, J=8.5 Hz, 1H), 6.93 (d, J=2.0 Hz, 1H), 6.77 (dd, J=2.0 Hz, 8.5 Hz, 1H), 3.94 (dd, J=5.5 Hz, 10.5 Hz, 1H), 3.79 (dd, J=5.5 Hz 10.5 Hz, 1H), 3.31 (s, 3H), 3.10(dd, J=10.0 Hz, 1.0 Hz, 1H), 3.00(dd, J=10.0 Hz, 11.0 Hz, 1H), 1.65 (s, 4H), 1.39–1.50 (m, 21), 1.30 (s, 3H), 1.25 (s, 6H), 1.24 (s, 6H).

(±)-[(S)-3-Ethoxymethyl-2-methyl-2-(5,5,8,8-tetramethyl-5,6,7,8-tetrahydro-naphthalen-2-yl)-cyclopropyl]-methanol (Intermediate 6b)

Following a procedure similar to that for the preparation of Intermediate 6a using Intermediate 4 as the starting material and ethyl iodide as alkylating reagent yielded the title compound as a colorless oil (69 mg, 78% yield):

$^1$HNMR (CDCl$_3$, 300 MHz) δ 7.07 (d, J=8.4 Hz, 1H), 6.84 (d, J=2.1 Hz, 1H), 6.67 (dd, J=2.1 Hz, 8.4 Hz, 1H), 3.74–3.89 (m, 2H), 3.25–3.41 (m, 11), 2.89–3.05 (m, 2H), 1.56 (s, 4H), 1.28–1.43 (m, 2H), 1.21 (s, 3H), 1.55 (s, 12H), 1.1 (t, J=6.9 Hz, 3H).

(±)-[(R)-3-Methoxymethyl-2-methyl-2-(5,5,8,8-tetramethyl-5,6,7,8-tetrahydro-naphthalen-2-yl)-cyclopropyl]-methanol (Intermediate 7a)

Following a procedure similar to that for the preparation of Intermediate 6a using Intermediate 5 as the starting material and methyl iodide as the alkylating reagent provided the title compound as a colorless oil (67 mg, 40% yield):

$^1$HNMR (CDCl$_3$, 500 MHz) δ 7.18–7.20 (m, 2H), 7.03 (dd, J=1.5 Hz, 7.5 Hz, 1H), 3.55–3.61 (m, 2H), 3.41 (s, 3H), 3.22–3.21 (m, 2H), 1.65 (s, 3H), 1.34–1.42 (m, 5H), 1.24 (s, 12H), 1.09–1.13 (m, 1H).

(±)-[(R)-3-Ethoxymethyl-2-methyl-2-(5,5,8,8-tetramethyl-5,6,7,8-tetrahydro-naphthalen-2-yl)-cyclopropyl]-methanol (Intermediate 7b)

Following a procedure similar to that for the preparation of Intermediate 6a using Intermediate 5 as the starting material and ethyl iodide as the alkylating reagent provided the title compound (65 mg, 81% yield) as a colorless oil:

$^1$HNMR (CDCl$_3$, 300 MHz) δ 7.12–714 (m, 21), 6.99 (dd, J=1.8 Hz, 8 Hz, 1H), 3.46–3.56 (m, 4H), 3.20 (d, J=7.2 Hz, 2H), 1.59 (s, 41), 1.34–1.37 (m, 4H), 1.03–1.19 (m, 15H), 1.02–1.15 (m, 1H).

(1S, 2R, 3R)-3-Methoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 8a) and (1R, 2S, 3S)-3-Methoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 9a)

1-(S)-(–)-Camphanic chloride (113 mg, 0.75 mmol) and N,N-dimethylaminopyridine (113 mg, 0.93 mmol) were added to a solution of Intermediate 6a (100 mg, 0.46 mmol) in 5 mL of dichloromethane. After stirring at room temperature for 16 h, the mixture was extracted with dichloromethane (2×10 mL), washed with water (1×10 mL), dried (Na$_2$SO$_4$) and concentrated to give a crude colorless oil. Purification by column chromatography using 10% EtOAc in hexane afforded a mixture of Intermediates 8a and 9a in 1:1 ratio (162 mg, 89% yield). Separation of this mixture with normal phase HPLC (Whatman, Partisil-10-PAC HPLC column) using 8% EtOAc in hexane as eluent yielded Intermediate 8a (83 mg, 45% yield) and Intermediate 9a (79 mg, 44% yield) as colorless oils:

$^1$HNMR for Intermediate 8a: (CDCl$_3$, 500 MHz) δ 7.23 (d, J=2.0 Hz, 1H), 7.20 (d, J=8.5 Hz, 1H), 6.97 (dd, J=2.0 Hz, 8.5 Hz, 1H), 4.25–4.29 (m, 1H), 3.97–4.00 (m, 1H), 3.32–3.24 (m, 5H), 2.41–2.46 (m, 1H), 1.94–2.06 (m, 1H), 1.90–1.95 (m, 1H), 1.66–1.72 (m, 4H), 1.56 (s, 4H), 1.37–1.45 (m, 2H), 1.34 (s, 3H), 1.26 (s, 6H), 1.25 (s, 3H), 1.12 (s, 3H), 1.07 (s, 3H), 0.99 (s, 3H);

$^1$HNMR for Intermediate 9a: (CDCl$_3$, 500 MHz) δ 7.22 (d, J=2.0 Hz, 1H); 7.18 (d, J=8.5 Hz, 1H), 6.99 (dd, J=2.0 Hz, 8.5 Hz, 1H), 4.26–4.30 (m, 1H), 3.97–3.99 (m, 1H), 3.31–3.28 (m, 5H), 2.42–2.46 (m, 1H), 1.94–2.06 (m, 1H), 1.90–1.95 (m, 1H), 1.66–1.72 (m, 4H), 1.56 (s, 4H), 1.37–1.45 (m, 2H), 1.34 (s, 3H), 1.26 (s, 6H), 1.25 (s, 3H), 1.12 (s, 3H), 1.07 (s, 3H), 0.99 (s, 3H).

(1S, 2R, 3R)-3-Ethoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 8b) and (1R, 2S, 3S)-3-Ethoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 9b)

Following a procedure, similar to that for the preparations of Intermediates 8a and 9a but using Intermediate 6b as the starting material afforded Intermediate 8b (62 mg, 50% yield) and Intermediate 9b (60 mg, 49% yield) as colorless oils:

$^1$HNMR for Intermediate 8b: (CDCl$_3$, 500 MHz) δ 7.23 (d, J=2.0 Hz, 1H), 7.20 (d, J=8.5 Hz, 1H), 6.97 (dd, J=2.0 Hz, 8.5 Hz, 1H), 4.25–4.29 (m, 1H), 3.97–4.00 (m, 1H),3.40 (q, J=6.9 Hz, 2H), 3.32–3.24 (m, 2H), 2.41–2.46 (m, 1H), 1.94–2.06 (m, 1H), 1.90–1.95 (m, 1H), 1.66–1.72 (m, 4H), 1.56 (s, 4H), 1.37–1.45 (m, 2H), 1.34 (s, 3H), 1.19–1.26 (m, 9H), 1.18 (s, 3H), 1.12 (s, 3H), 1.07 (s, 3H), 0.99 (s, 3H);

$^1$HNMR for Intermediate 9b: (CDCl$_3$, 500 MHz) δ 7.22 (d, J=2.0 Hz, 1H), 7.18 (d, J=8.5 Hz, 1H), 6.99 (dd, J=2.0 Hz, 8.5 Hz, 1H), 4.26–4.30(m, 1H), 3.97–3.99 (m,1H), 3.40 (q, J=6.9 Hz, 2H), 3.31–3.28 (m, 2H), 2.42–2.46 (m, 1H), 1.94–2.06 (m, 1H), 1.90–1.95 (m, 1H), 1.66–1.72 (m, 4H), 1.56 (s, 4H), 1.37–1.45 (m, 2H), 1.34 (s, 3H), 1.19–1.26 (m, 9H), 1.18 (s, 3H), 1.12 (s, 3H), 1.07 (s, 3H), 0.99 (s, 3H).

(1S, 2R, 3S)-3-Methoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 10a) and (1R, 2S, 3R)-3-Methoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 11a)

Following a procedure similar to that for the preparation of Intermediates 8a and 9a while using Intermediate 7a as the starting material and 10% EtOAc in hexane as normal phase HPLC eluent afforded Intermediate 10a (46 mg, 36% yield) and Intermediate 11a (45 mg, 36% yield) from 7a as colorless oils:

$^1$HNMR for Intermediate 10a: (CDCl$_3$, 500 MHz) δ 7.18 (d, J=8.5 Hz, 1H), 7.10 (d, J=2.0 Hz, 1H), 6.95 (dd, J=2.0 Hz, 8.5 Hz, 1H, 3.95–3.99 (m, 1H), 3.80–3.84 (m, 1H), 3.59–3.62 (m, 1H), 3.51–3.55 (m, 1H), 3.40 (s, 3H), 2.41–2.46 (m, 1H), 1.94–2.06 (m, 1H), 1.90–1.95 (m, 1H) 1.66–1.72 (m, 4H), 1.56 (s, 4H), 1.37–1.45 (m, 2H), 1.34 (s, 3H), 1.26 (s, 6H), 1.25 (s, 3H), 1.12 (s, 3H), 1.07 (s, 3H) 0.99 (s, 3H);

$^1$HNMR for Intermediate 11a: (CDCl$_3$, 500 MHz) δ 7.16 (d, J==8.5 Hz, 1H), 7.15 (d, J=2.0 Hz, 1H), 7.02 (dd, J=2.0 Hz, 8.5 Hz, 1H), 3.90–3.94 (m, 1H), 3.72–3.76(m,1H), 3.51–3.55 (m, 1H), 3.44–3.48 (m, 1H), 2.27–2.33 (m, 1H), 1.94–2.06 (m, 1H), 1.90–1.95 (m, 1), 1.66–1.72 (m, 4H), 1.56 (s, 4H), 1.37–1.45 (m, 2H), 1.34(s, 3H), 1.26 (s, 6H), 1.25 (s, 3H), 1.12 (s, 3H), 1.07(s, 3H), 0.99 (s, 3H)

(1S, 2R, 3S)-3-Ethoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 10b) and (1R, 2S, 3R)-3-Ethoxymethyl-2-methyl-2-(5,5,8,8-tetramethyl-5,6,7,8-tetrahydro-naphthalen-2-yl)-cyclopropylmethyl 4,7,7-trimethyl-3-oxo-2-oxa-bicyclo[2.2.1]heptane-1-carboxylate (Intermediate 11b)

Following a procedure similar to that for the preparation of Intermediates 8a and 9a but using intermediate 7b as the starting material and 10% EtOAc in hexane as normal phase HPLC eluent afforded Intermediate 10b (49 mg, 42% yield) and Intermediate 11b (48 mg, 42% yield) from 7b as colorless oils:

¹HNMR for Intermediate 10b: (CDCl₃, 300 MHz) δ 7.25 (d, J=8.5 Hz, 1H), 7.18 (d, J=2.0 Hz, 1H), 7.02 (dd, J=2.0 Hz, 8.5 Hz, 1H), 3.95–3.99 (m,1H), 3.78–3.85 (m, 1H), 3.51–3.67 (m, 4H), 2.41–2.46 (m, 1H), 1.94–2.06 (m, 1H), 1.90–1.95 (m, 1H), 1.66–1.72 (m, 4H), 1.56 (s, 4H), 1.37–1.45 (m, 2H), 1.34 (s, 3H), 1.15–1.26 (s, 12H), 1.1 (s, 3H), 1.02 (s, 3H) 0.96 (s, 3H);

¹HNMR for Intermediate 11b: (CDCl₃, 300 MHz) δ 7.25 (d, J=8.5 Hz, 1H), 7.18 (d, J=2.0 Hz, 1H), 7.02 (dd, J=2.0 Hz, 8.5 Hz, 1H), 3.95–4.01 (m, 1H), 3.78–3.84 (m, 1H), 3.51–3.67 (m, 4H), 2.33–2.42 (m, 1R), 1.94–2.02 (m, 1H), 1.89–1.94 (m, 1H), 1.66–1.72 (m, 4H), 1.56 (s, 4H), 1.37–1.45 (m, 2H), 1.34 (s, 3H), 1.15–1.26 (s, 12H), 1.1 (s, 3H), 1.02 (s, 3H), 0.96 (s, 3H).

(+)-(1S, 2R, 3R)-3-Methoxymethyl-2-methyl-2-(5,5,8,8-tetramethyl-5,6,7,8-tetrahydro-naphthalen-2-yl)-cyclopropanecarbaldehyde (Intermediate 12a)

Potassium hydroxide solution (1N, 1 mL) was added to a solution of Intermediate 8a (83 mg, 0.21 mmol) in 4 mL of THF/MeOH (1:1) at room temperature. After stirring for an hour, the mixture was diluted with ethyl acetate (10 mL) and acidified with 1 mL of 1N HCl at 0° C. The organic layer was then washed with brine (1×5 mL), dried (Na₂SO₄) and concentrated. The residue was purified, by flash chromatography using 20% EtOAc in hexane to give the corresponding alcohol (45 mg, 100% yield). This alcohol was subsequently dissolved in dichloromethane (5 mL) and acetonitrile (0.5 mL). To this solution was added molecular sieve (45 mg), 4-methylmorpholine N-oxide (23 mg, 0.40 mmol) and tetrapropylammonium perruthenate (5 mg, 0.01 mmol). After stirring at room temperature for 45 min, the solvent was then removed under reduced pressure and the residue was purified by flash chromatography using 10% EtOAc in hexane to obtain the title compound in optically pure form (44 mg, 99% yield) as a colorless oil:

¹HNMR (CDCl₃, 300 Hz) δ 8.8 (d, J=7.5 Hz, 1H), 7.15–7.18 (m, 2H), 6.90 (dd, J=4 Hz, 14 Hz, 1H), 3.63–6.68 (m, 1H), 3.26–3.41 (m, 1H), 3.26 (s, 3H), 1.88–1.97 (m, 2H), 1.60 (s, 4H), 1.35 (s, 3H), 1.19 (s, 12H).

(+)-(1S, 2R, 3R)-3-Ethoxymethyl-2-methyl-2-(5,5,8,8-tetramethyl-5,6,7,8-tetrahydro-naphthalen-2-yl)-cyclopropanecarbaldehyde (Intermediate 12b)

Following a procedure similar to that for the preparation of Intermediate 12a but using Intermediate 8b as the starting material afforded the title compound (36 mg, 97% yield) as a colorless oil:

¹HNMR (CDCl₃, 300 MHz) δ 8.8 (d, J=7.5 Hz, 1H), 7.15–7.18 (m, 2H), 6.90 (dd, J=4 Hz, 14 Hz, 1H), 3.67=3.73 (m, 1H), 3.31–3.45 (m, 3H), 1.88–1.97 (m, 2H), 1.60 (s, 4H), 1.35 (s, 3H), 1.19 (s, 12H), 1.11 (t, J=7 Hz, 3H).

(−)-(1R, 2S, 3S)-3-Methoxymethyl-2-methyl-2-(5,5,8,8-tetramethyl-5,6,7,8-tetrahydro-naphthalen-2-yl)-cyclopropanecarbaldehyde (Intermediate 13a)

Following a procedure similar to that for the preparation of Intermediate 12a but using Intermediate 9a as the starting material afforded the title compound (42 mg, 99% yield) as a colorless oil:

¹HNMR (CDCl₃, 300 MHz) δ 8.8 (d, J=7.5 Hz, 1H), 7.15–7.18 (m, 2H), 6.90 (dd, J=4 Hz, 14 Hz, 1H), 3.62–3.68 (m, 1H), 3.26–3.41 (m, 1H), 3.26 (s, 3H), 1.88–1.97 (m, 2H), 1.60 (s, 4H), 1.35 (s, 3H), 1.19 (s, 12H).

(−)-(1R, 2S, 3S)-3-Ethoxymethyl-2-methyl-2-(5,5,8,8-tetramethyl-5,6,7,8-tetrahydro-naphthalen2-yl)-cyclopropanecarbaldehyde (Intermediate 13b)

Following a procedure similar to that for the preparation of Intermediate 12a but using Intermediate 9b as the starting material afforded the title compound (36 mg, 94% yield) as a colorless oil:

¹HNMR (CDCl₃, 300 MHz) δ 8.8 (d, J=7.5 Hz, 1H), 7.15–7.18 (m, 2H), 6.90 (dd, J=4 Hz, 14 Hz, 1H), 3.67–3.73 (m, 1H), 3.31–3.45 (m, 3H), 1.88–1.97 (m, 2H), 1.60 (s, 4H), 1.35 (s, 3H), 1.19 (s, 12H), 1.11 (t, J=7 Hz, 3H).

(+)-(1S 2R, 3S)-3-Methoxymethyl-2-methyl-2-(5,5,8,8-tetramethyl-5,6,7,8-tetrahydro-naphthalen-2-yl)-cyclopropanecarbaldehyde (Intermediate 14a)

Following a procedure similar to that for the preparation of Intermediate 12a but using Intermediate 10a as the starting material afforded the title compound (23 mg, 84% yield) as a colorless oil:

¹HNMR(CDCl₃, 300 MHz) δ 8.38 (d, J=7.8 Hz, 1H), 7.11–7.19 (m, 2H), 6.90 (dd, J=2.1 Hz, 8.1 Hz, 1H), 3.47–3.65 (m, 2H), 3.36 (s, 3H) 2.30–2.37 (m, 1H), 1.67–1.71 (m, 1H), 1.58 (s, 4H), 1.38 (s, 3H), 1.16–1.19 (m, 12H).

(+)-(1S, 2R, 3S)-3-Ethoxymethyl-2-methyl-2-(5,5,8,8-tetramethyl-5,6,7,8-tetrahydro-naphthalen-2-yl)-cyclopropanecarbaldehyde (Intermediate 14b)

Following a procedure similar to that for the preparation of Intermediate 12a but using Intermediate 10b as the starting material afforded the title compound (27 mg, 98% yield) as a colorless oil:

¹HNMR (CDCl₃, 300 MHz) δ 8.37 (d, J=7.2 Hz, 1H), 7.11–7.19 (m, 2H), 6.90 (dd, J=2.1 Hz, 8.1 Hz, 1H), 3.46–3.67 (m, 4H), 2.32–2.37 (m, 1H), 1.67–1.71 (m, 1H) 1.59 (s, 4H), 1.38 (s, 3H), 1.19 (s, 6H), 1.18 (s, 6H), 1.16 (t, J=6.5 Hz, 3H).

(−)-(1R, 2S, 3R)-3-Methoxymethyl-2-methyl-2-(5,5,8,8-tetramethyl-5,6,7,8-tetrahydro-naphthalen-2-yl)-cyclopropanecarbaldehyde (Intermediate 15a)

Following a procedure similar to that for the preparation of Intermediate 12a but using Intermediate 11a as the starting material afforded the title compound (25 mg, 81% yield) as a colorless oil:

¹HNMR (CDCl₃, 300 MHz) δ 8.38 (d, J=7.8 Hz, 1H), 7.11–7.19 (m, 2H), 6.90 (dd, J=2.1 Hz, 8.1 Hz, 1H), 3.47–3.65 (m, 2H), 3.36 (s, 3H), 2.30–2.37 (m, 1H), 1.67–1.71 (m, 1H), 1.58 (s, 4H), 1.38 (s, 1H), 1.16–1.19 (m, 12H).

(−)-(1R, 2S, 3R)-3-Ethoxymethyl-2-methyl-2-(5,5,8,8-tetramethyl-5,6,7,8-tetrahydro-naphthalen-2-yl)-cyclopropanecarbaldehyde (Intermediate 15b)

Following a procedure similar to that for the preparation of Intermediate 12a but using Intermediate 11b as the starting material afforded the title compound (25 mg, 97% yield) as a colorless oil:

¹HNMR (CDCl₃, 300 MHz) δ 8.37 (d, J=7.2 Hz, 1H), 7.11–7.19 (m, 2H), 6.90 (dd, J=2.1 Hz, 8.1 Hz, 1H), 3.46–3.67 (m, 4H), 2.32–2.37 (m, 1H), 1.67–1.71 (m, 1H), 1.59 (s, 4H), 1.38 (s, 3H), 1.19 (s, 6H), 1.18 (s, 6), 1.16 (t, J=6.5 Hz, 3H).

Ethyl (+)-(1S, 2R, 3R)-5-[3-methoxymethyl-2-methyl-2-(5,5,8,8-tetramethyl-5,6,7,8-tetrahydro-naphthalen-2-yl)-cyclopropyl]-3-methyl-penta-2E,4E-dienoate (Compound 16a)

n-Butyl lithium in hexane(1.6 M, 1.25 mL, 2.0 mmol) was added to a solution of triethylphosphono-3-methyl-2E-butenoate (available from Aldrich) (528 mg, 2.0 mmol) in 5 mL of THF and 3 mL of 1,3-dimethyl-3,4,5,6-tetrahydro-2

(1H)-pyrimidinone (DMPU) at −78° C. After stirring for 5 min, a solution of Intermediate 12a (44 mg, 0.20 mmol) in 1 mL of THF was added by cannulation. The resulting solution was stirred at −78° C. for 2 h before it was quenched with saturated NH$_4$Cl. The mixture was then extracted with ether (3×5 mL), washed with brine (1×10 mL), dried (Na$_2$SO$_4$) and concentrated to give a crude colorless oil. Purification by column chromatography using 5% EtOAc in hexane afforded the title compound (59 mg, 70% yield) as a white solid:

$^1$HNMR (CDCl$_3$, 300 MHz) δ 7.17 (d, J=8.4 Hz, 1H), 7.07 (d, J=1.8 Hz, 1H), 6.88 (dd, J=1.8 Hz, 1.8 Hz, 1H), 6.25 (d, J=15.6 Hz, 1H), 5.61 (s, 1H), 5.44 (dd, J=10.8 Hz, 15.6 Hz, 1H), 4.07 (q, J=7.2 Hz, 2H), 3.29–3.35 (m, 1H), 3.23 (s, 3H), 3.10–3.16 (dd, J=7.8 Hz, 2.4 Hz, 1H), 2.02 (s, 3H), 1.77–1.83 (m, 1H), 1.59 (s, 4H), 1.52–1.57 (m, 1H), 1.30 (s, 3H), 1.18–1.22 (m, 15H).

Ethyl (+)-(1S, 2R, 3R)-5-[3-ethoxymethyl-2-methyl-2-(5,5, 8,8-tetramethyl-5,6,7,8-tetrahydro-2-yl)-cyclopropyl]-3methyl-penta-2E,4E-dienoate (Compound 16b)

Following a procedure similar to that for the preparation of Compound 16a but using Intermediate 12b as the starting material afforded the title compound (42 mg, 88% yield) as a white solid:

$^1$HNMR (CDCl$_3$, 500 MHz) δ 7.12 (d, J=8.4 Hz, 1H), 7.07 (d, J—1.8 Hz, 1H), 6.90 (dd, J=1.8 Hz, 1.8 Hz, 1H), 6.23 (d, J=15.6 Hz, 1H), 5.61 (s, 1H), 5.44 (dd, J=10.8 Hz, 15.6 Hz, 1H); 4.08 (q, J=7.2 Hz, 2H), 3.32–3.37 (m, 3H), 3.15–3.19 (m, 1H), 2.02 (s, 3H), 1.77–1.83 (m, 1H), 1.59 (s, 4H), 1.52–1.57 (m, 1H), 1.30 (s, 3H), 1.17–1.30 (m, 18H).

Ethyl (−)-(1R, 2S, 3S)-5-[3-methoxymethyl-2-methyl-2-(5, 5,8,8-tetramethyl-5,6,7,8-tetrahydro-naphthalen-2-yl)-cyclopropyl]-3-methyl-penta-2E,4E-dienoate (Compound 17a)

Following a procedure similar to that for the preparation of Compound 16a but using Intermediate 13a as the starting material afforded the title compound (53 mg, 66% yield) as a white solid:

$^1$HNMR (CDCl$_3$, 500 MHz) δ 7.17 (d, J=8.4 Hz, 1H), 7.07 (d, J=1.8 Hz, 1H), 6.88 (dd, J=1.8 Hz, 1.8 Hz, 1H), 6.25 (d, J=15.6 Hz, 1H), 5.61 (s, 1H), 5.44 (dd, J=10.8 Hz, 15.6 Hz, 1H), 4.07 (q, J=7.2 Hz, 2H), 3.29–3.35 (m, 1H), 3.23 (s, 3H), 3.10–3.16 (dd, J=7.8 Hz, 2.4 Hz, 1H), 2.02 (s, 3H), 1.77–1.83 (m, 1H), 1.59 (s, 4H), 1.52–1.57 (m, 1H), 1.30 (s, 3H), 1.18–1.22 (m, 15H).

Ethyl (−)-(1R, 2S, 3S)-5-[3-ethoxymethyl-2-methyl-2-(5,5, 8,8-tetramethyl-5,6,7,8-tetrahydro-naphthalen-2-yl)-cyclopropyl]-3-methyl-penta-2E,4E-dienoate (Compound 17b)

Following a procedure similar to that for the preparation of Compound 16a but using Intermediate 13b as the starting material afforded the title compound (44 mg, 92% yield) as a white solid:

$^1$HNMR (CDCl$_3$, 500 MHz) δ 7.12 (d, J=8.4 Hz, 1H), 7.07(d, J=1.8 Hz, 1H), 6.90 (dd, J=1.8 Hz, 1.8 Hz, 1H), 6.23 (d, J=15.6 Hz, 1H), 5.61 (s, 1H), 5.44 (dd, J=10.8 Hz, 15.6 Hz, 1H), 4.08 (q, J=7.2 Hz, 2H), 3.32–3.37 (m, 3H), 3.15–1.19 (m, 1H), 2.02 (s, 3H), 1.77–1.83 (m, 1H), 1.59 (s, 4H), 1.52–1.57 (m, 1H), 1.30 (s, 3H), 1.17–1.30 (m, 18H).

Ethyl (+)-(1S, 2R, 3S)-5-[3-methoxymethyl-2-methyl-2-(5, 5,8,8-tetramethyl-5,6,7,8-tetrahydro-naphthalen-2-yl)-cyclopropyl]3-methyl-penta-2E,4E-dienoate (Compound 18a)

Following a procedure similar to that for the preparation of Compound 16a but using Intermediate 14a as the starting material afforded the title compound (32 mg, 76% yield) as a white solid:

$^1$HNMR (CDCl$_3$, 300 MHz) δ 7.14 (d, J=8.4 Hz, 1H), 7.02 (d, J=2.1 Hz, 1H), 6.93 (dd, J=2.1 Hz, 8.4 Hz, 1H), 6.10 (d, J=15.6 Hz, 1H), 5.54 (s, 1H), 5.17 (dd, J=9.6 Hz, 15.3 Hz, 1H), 4.07 (q, J=7.0 Hz, 2H), 3.53–3.58 (m, 2H), 3.35 (s, 3H), 1.91 (s, 3H), 1.47–1.58 (m, 6H), 1.34 (s, 3H), 1.11–1.22 (m, 18H).

Ethyl (+)-(1S, 2R, 3S)-5-[3-ethoxymethyl-2-methyl-2-(5,5, 8,8-tetramethyl-5,6,7,8-tetrahydro-naphthalen-2-yl)-cyclopropyl]-3-methyl-penta-2E,4E-dienoate (Compound 18b)

Following a procedure similar to that for the preparation of Compound 16a but using Intermediate 14b as the starting material afforded the title compound (38 mg, 74% yield) as a white solid:

$^1$HNMR (CDCl$_3$, 300 MHz) δ 7.14 (d, J=8.4 Hz, 1H), 7.02 (d, J=2.1 Hz, 1H), 6.94 (dd, J=2.1 Hz, 8.4 Hz, 1H), 6.10 (d, J=15.6 Hz, 1H), 5.54 (s, 1H), 5.17 (dd, J=9.6 Hz, 15.3 Hz, 1H), 4.05 (q, J=7.0 Hz, 2H), 3.45–3.66 (m, 4H), 1.91 (s, 3H), 1.47–1.58 (m, 6H), 1.34 (s, 3H), 1.11–1.22 (m, 21H).

Ethyl (−)-(1R, 2S, 3R)-5-[3-methoxymethyl-2-methyl-2-(5, 5,8,8-tetramethyl-5,6,7,8-tetrahydro-naphthalen-2-yl)-cyclopropyl]-3-methyl-penta-2E,4E-dienoate (Compound 19a)

Following a procedure similar to that for the preparation of Compound 16a but using Intermediate 15a as the starting material afforded the title compound (34 mg, 75% yield) as a white solid:

$^1$HNMR (CDCl$_3$, 300 MHz) δ 7.14 (d, J=8.4 Hz, 1H), 7.02 (d, J=2.1 Hz, 1H), 6.93 (dd, J=2.1 Hz, 8.4 Hz, 1H), 6.10 (d, J=15.6 Hz, 1H), 5.54 (s, 1H), 5.17 (dd, J=9.6 Hz, 15.3 Hz, 1H), 4.07 (q, J=7.0 Hz, 2H), 3.53–3.58 (m, 2H), 3.35 (s, 3H), 1.91 (s, 3H), 1.47–1.58 (m, 6H), 1.34 (s, 3H), 1.11–1.22 (m, 18H).

Ethyl (−)-(1R, 2S, 3R)-5-[3-ethoxymethyl-2-methyl-2-(5,5, 8,8-tetramethyl-5,6,7,8-tetrahydro-naphthalen-2-yl)-cyclopropyl]-3-methyl-penta-2E,4E-dienoate (Compound 19b)

Following a procedure similar to that for the preparation of Compound 16a but using Intermediate 15b as the starting material afforded the title compound (35 mg, 73% yield) as a white solid:

$^1$HNMR (CDCl$_3$, 300 MHz) δ 7.14 (d, J=8.4 Hz, 1H), 7.02 (d, J=2.1 Hz, 1H), 6.94 (dd, J=2.1 Hz, 8.4 Hz, 1H), 6.10 (d, J=15.6 Hz, 1H), 5.54 (s, 1H); 5.17 (dd, J=9.6 Hz; 15.3 Hz, 1H), 4.05 (q, J=7.0 Hz, 2H), 3.45–3.66 (m, 4H), 1.91 (s, 3H), 1.47–1.58 (m, 6H), 1.34 (s, 3H), 1.11–1.22 (m, 2H).

(+)-(1S, 2R, 3R)-5-[3-Methoxymethyl-2-methyl-2-(5,5,8,8-tetramethyl-5,6,7,8-tetrahydro-naphthalen-2-yl)-cyclopropyl]-3-methyl-penta-2E,4E-dienoic Acid (Compound 20a)

Sodium hydroxide solution (1N, 1 mL) was added to a solution of Compound 16a (59 mg, 0.13 mmol) in 4 mL of THF/MeOH (1:1) at 50° C. After stirring at 50° C. for 16 h, the mixture was diluted with ethyl acetate (10 mL) ad acidified with 1 mL of 1 HCl at 0° C. The organic layer was then washed with brine (1×5 mL), dried (Na$_2$SO$_4$) and concentrated. The residue was purified by flash chromatography using 30% EtOAc in hexane to give the title compound (43 mg, 79% yield) as a white solid:

1HNMR (CDCl$_3$, 300 MHz) δ 7.20 (d, J=8.0 Hz, 1H), 7.14 (d, J=1.8 Hz, 1H), 7.04 (dd, J=1.8 Hz, 8.4 Hz, 1H), 6.35 (d, J=15.3 Hz, 1H), 5.71 (s, 1H), 5.61 (dd, J=10.5 Hz, 15.3 Hz, 1H), 3.32–3.44 (m, 1H), 3.31 (s, 3H), 3.19–3.24 (m, 1H), 2.11 (s, 3H), 1.64–1.85 (m, 1H), 1.64–1.66 (m, 5H), 1.25–1.38 (m, 12H).

(+)-(1S, 2R, 3R)-5-[3-Ethoxymethyl-2-methyl-2-(5,5,8,8-tetramethyl-5,6,7,8-tetrahydro-naphthalen-2-yl)-cyclopropyl]-3-methyl-penta-2E,4E-dienoic acid (Compound 20b)

Following a procedure similar to that for the preparation of Compound 20a but using Compound 16b as the starting material afforded the title compound (36 mg, 91% yield) from 16b as a white solid.

$^1$HNMR (CDCl$_3$, 500 MHz) δ 7.13 (d, J=8.0 Hz, 1H), 7.06 (d, J=1.8 Hz, 1H), 6.90 (dd, J=1.8 Hz, 8.4 Hz, 1H), 6.28 (d, J=15.3 Hz, 1H), 5.64 (s, 1H), 5.50 (dd, J=10.5 Hz, 15.3 Hz, 1H), 3.32–3.38 (m, 3H), 3.16–3.20 (m, 1H), 2.04 (s, 3H), 1.64–1.85 (m, 1H), 1.32–1.59 (m, 5H), 1.31 (s, 3H), 1.25–1.38 (m, 16H).

(−)-(1R, 2S, 3 S)-5-[3-Methoxymethyl-2-methyl-2-(5,5,8,8-tetramethyl-5,6,7,8-tetrahydro-naphthalen-2-yl)-cyclopropyl]-3-methyl-penta-2E,4E-dienoic acid (Compound 21a)

Following a procedure similar to that for the preparation of Compound 20a but using Compound 17a as the starting material afforded the title compound (42 mg, 85% yield) as a white solid:

$^1$HNMR (CDCl$_3$, 300 MHz) δ 7.20 (d, J=8.0 MHz, 1H), 7.14 (d, J=1.8 Hz, 1H), 7.04 (dd, J=1.8 Hz, 8.4 Hz, 1H), 6.35 (d, J=15.3 Hz, 1H), 5.71 (s, 1H), 5.61 (dd, J=10.5 Hz, 15.3 Hz, 1H), 3.32–3.44 (m, 1H), 3.31 (s, 3H), 3.19–3.24 (m, 1H), 2.11 (s, 3H), 1.64–1.85 (m, 1H), 1.64–1.66 (m, 5H), 1.25–1.38 (m, 12H).

(−)-(1R, 2S, 3S)-5-[3-Ethoxymethyl-2-methyl-2-(5,5,8,8-tetramethyl-5,6,7,8-tetrahydro-naphthalen-2-yl)-cyclopropyl]-3-methyl-penta-2E,4E-dienoic acid (Compound 21b)

Following a procedure similar to that for the preparation of Compound 20a but using Compound 17b as the starting, material afforded the title compound (35 mg, 86% yield) as a white solid:

$^1$HNMR (CDCl$_3$, 300 MHz) δ 7.13 (d, J=8.0 Hz, 1H), 7.06 (d, J=1.8 Hz, 1H), 6.90 (dd, J=1.8 Hz, 8.4 Hz, 1H), 6.28 (d, J=15.3 Hz, 1H), 5.64 (s, 1H), 5.50 (dd, J=10.5 Hz, 15.3 Hz, 1H), 3.32–3.38 (m, 3H), 3.16–3.20 (m, 1H), 2.04 (s, 3H), 1.64–1.85 (m, 1H), 1.32–1.59 (m, 5H), 1.31 (s, 3H), 1.25–1.38 (m, 16H).

(+)-(1S, 2R, 3S)-5-[3-Methoxymethyl-2-methyl-2-(5,5,8,8-tetramethyl-5,6,7,8-tetrahydro-naphthalen-2-yl)-cyclopropyl]-3-methyl-penta-2E,4E-dienoic acid (Compound 22a)

Following a procedure similar to that for the preparation of Compound 20a but using Compound 18a as the starting material afforded the title compound (28 mg, 93% yield) as a white solid:

$^1$HNMR (CDCl$_3$, 500 MHz) δ 7.20 (d, J=8.0 Hz, 1H), 7.09 (d, J=2.0 Hz, 1H), 7.00 (dd, J=2.0 Hz, 8.0 Hz, 1H), 6.19 (d, J=15.5 Hz, 1H), 5.63 (s, 1H), 5.30 (dd, J=10 Hz, 15.5 Hz, 1H), 3.62–3.65 (m, 2H), 3.42 (s, 3H), 1.98 (s, 3H), 1.57–1.70 (m, 5H), 1.26–1.42 (s, 16H), 1.17 (s, 3H).

(+)-(1S, 2R, 3S)-5-[3-Ethoxymethyl-2-methyl-2-(5,5,8,8-tetramethyl-5,6,7,8-tetrahydro-naphthalen-2-yl)-cyclopropyl]-3-methyl-penta-2E,4E-dienoic acid (Compound 22b)

Following a procedure similar to that for the preparation of Compound 20a but using Compound 18b as the starting material afforded the title compound (31 mg, 87% yield) as a white solid:

$^1$HNMR (CDCl$_3$, 300 MHz) δ 7.20 (d, J=8.4 Hz, 1H), 7.09 (d, J=1.8 Hz, 1H), 7.00 (dd, J=1.8 Hz, 8.4 Hz, 1H), 6.20 (d, J=15.6 Hz, 1H), 5.62 (s, 1H), 5.25–5.34 (dd, J=9.6 Hz, 15.3 Hz, 1H), 3.52–3.73 (m, 4H), 1.98 (s, 3H), 1.65–1.70 (m, 5H), 1.54–1.60 (m, 1H), 1.22–1.41 (m, 18H).

(−)-(1R, 2S, 3R)-5-[3-Methoxymethyl-2-methyl-2-(5,5,8,8-tetramethyl-5,6,7,8-tetrahydro-naphthalen-2-yl)-cyclopropyl]-3-methyl-penta-2E,4E-dienoic acid (Compound 23a)

Following a procedure similar to that for the preparation of Compound 20a but using Compound 19a as the starting material afforded the title compound (26 mg, 80% yield) as a white solid:

$^1$HNMR (CDCl$_3$, 500 MHz) δ 7.20 (d, J=8.0 Hz, 1H), 7.09 (d, J=2.0 Hz, 1H), 7.00 (dd, J=2.0 Hz, 8.0 Hz, 1H), 6.19 (d, J=15.5 Hz, 1H), 5.63 (s, 1H), 5.30 (dd, J=10 Hz, 15.5 Hz, 1H), 3.62–3.65 (m, 2H), 3.42 (s, 3H), 1.98 (s, 3H), 1.57–1.70 (m, 5H), 1.26–1.42 (s, 16H), 1.17 (s, 3H).

(−)-(1R, 2S, 3R)-5-[3-Ethoxymethyl-2-methyl-2-(5,5,8,8-tetramethyl-5,6,7,8-tetrahydro-naphthalen-2-yl)-cyclopropyl]-3-methyl-penta-2E,4E-dienoic acid (Compound 23b)

Following a procedure similar to that for the preparation of Compound 20a but using Compound 19b as the starting material afforded the title compound (26 mg, 80% yield) as a white solid:

$^1$HNMR (CDCl$_3$, 500 MHz) δ 7.20 (d, J=8.4 Hz, 1H), 7.09 (d, J=1.8 Hz, 1H), 7.00 (dd, J=1.8 Hz, 8.4 Hz, 1H), 6.20 (d, J=15.6 Hz, 1H), 5.62 (s, 1H), 5.25–5.34 (dd, J=9.6 Hz, 15.3 Hz, 1H), 3.52–3.73 (m, 4H), 1.98 (s, 3H), 1.65–1.70 (m, 5H), 1.54–1.60 (m, 1H), 1.22–1.41 (m, 18H).

2,4-Diisopropyl-1-nitro-benzene (Intermediate 32)

Nitric acid (70%) (15.6 g, 185 mmol) was added slowly to a solution of 1,3-di-iso-propyl-benzene (available from Aldrich) (20 g, 123 mmol) in acetic acid (50 mL) and acetic anhydride (50 mL) at 0° C. over 20 min. After stirring at room temperature for 1 hour, the reaction mixture was diluted with water (250 mL) and hexane (500 mL). The organic layer was then washed with with water (50 mL), saturated Na$_2$CO$_3$ (50 mL), dried (Na$_2$SO$_4$) and concentrated to give the title compound in a crude form (25 g, 98% yield) as a colorless oil:

$^1$HNMR (CDCl$_3$, 300 MHz) δ 7.69 (d, J=2.1 Hz, 1H), 7.28 (d, J=2.1 Hz, 1H), 7.14 (dd, J=2.1 Hz, 8.4 Hz, 1H), 3.50 (m, 1H), 2.9 (m, 1H), 1.25 (m, 12H).

2,4-Diisopropyl-1-amino-benzene (Intermediate 33)

Mossey Tin (22 g, 184.5 mmol) was added to a solution of Intermediate 32 (25 g, 120 mmol), followed by conc. HCl (150 mL). After heating at 100° C. for 1 hour, acetic acid (50 mL) was added to the mixture and it was heated for another 30 minutes. After stirring at room temperature overnight, the reaction mixture was diluted with ether (500 mL), washed with water (50 mL) and transferred to a 500 mL beaker. Solid potassium carbonate was carefully added until all acids were quenched (~80 g). The mixture was then extracted with ether (3×100 mL), washed with brine (1×20 mL), dried (Na$_2$SO$_4$) and concentrated to give the title compound in a crude form as a brown oil that was taken to the next step without further purification:

$^1$HNMR (CDCl$_3$, 300 MHz) δ 7.01 (d, J=2.1 Hz, 1H), 6.91 (dd, J=2.1 Hz, 8.1 Hz, 1H), 6.60 (d, J=8.1 Hz, 1H), 5.80 (bs, 2H), 2.80–2.94 (m, 2H), 1.28–1.20 (m, 12H).

2,6-Diisopropyl-1-amino-2-bromo-benzene (Intermediate 34)

Bromine (19.7 mL, 123 mmol) was added to a solution of Intermediate 33 (crude) in acetic acid (100 mL) at 0° C. via addition funnel. After stirring at room temperature for 1 hour, the reaction mixture was diluted with water (200 mL) and diethyl ether (500 mL). The organic layer was then isolated and washed with water (50 mL). Solid potassium carbonate was carefully added to neutralize the solution. The ether layer was separated and washed with brine, dried ($Na_2SO_4$) and concentrated to give. Intermediate 34 as a brown oil which was taken to the next step without further purification:

$^1$HNMR (CDCl$_3$, 300 MHz) δ 7.16 (d, J=2.1 Hz, 1H), 6.93 (d, J=1.8 Hz, 1H), 2.75–2.90 (m, 2H), 1.18–1.26 (m, 12H).

2,5-Diisopropyl-1-bromo-benzene (Intermediate 35)

Trifluoroacetic acid (75 mL was added to a solution of Intermediate 34 in EtOH (100 mL) at 0° C. After stirring for 10 min, iso-amylnitrite (100 mL) was then added and the mixture was stirred for another 70 min. H$_3$PO$_2$ (70 mL) was added slowly and the mixture was warmed to ambient temperature over 5 hours. After dilution with ethyl acetate and sodium bicarbonate solution, the organic layer was separated, dried and concentrated to give the title compound in a crude form (17 g). Purification of the crude product by Kugelrohr distillation gave the title compound in pure form (13 g, 44% yield over 4 steps from 1,3-di-iso-propyl-benzene) as a colorless oil:

$^1$HNMR (CDCl$_3$, 300 MHz) δ 7.18 (d, J=1.5 Hz, 2H), 6.99 (s, 1H), 2.80–2.87 (m, 2H), 1.24 (s, 6H), 1.22 (s, 6H).

tert-Butyl-[3-(3,5-diisopropyl-phenyl)-but-2-enyloxy]-dimethyl-silane (Intermediate 36)

Bis(pinacolato)diboran (5.6 g, 22 mmol), potassium acetate (4.4 g, 44 mmol), and [1,1'-bis(diphenylphosphino) ferrocene]dichloropalladium (PdCl$_2$(dppf)$_2$) (730 mg, 0.89 mmol) were added to a solution of Intermediate 35 (3.5 g, 14.6 mmol) in 50 mL of DMF under argon. The mixture was then stirred at 80° C. for 24 h. After cooling to room temperature, 3-iodo-but-2Z-en-1-ol (obtainable in accordance with U.S. Pat. No. 6,147,224) (5.8 g, 29.2 mmol), 2M Na$_2$CO$_3$ (30 ml), and PdCl$_2$(dppf)$_2$ (730 mg 0.89 mmol) were added to the mixture, which was then stirred at 80° C. for another 24 h. The reaction was finally quenched with water (20 mL) and extracted with diethyl ether (3×10 mL). The organic layer was washed with brine (2×10 mL), dried (MgSO$_4$) and concentrated to give a crude brown oil. The crude oil was purified by flash chromatography using 20% EtOAc in hexane to obtain allylic alcohol (3 g, 88% yield) as a colorless oil.

tert-Butyldimethylsilyl chloride (3.9 g, 25.9 mmol) was added to the solution of allylic alcohol, (3 g, 12.9 mmol) and imidazole (2.6 g, 38.7 mmol) in 10 mL of DMF. The mixture was then stirred for 16 h at room temperature. After quenching with water the mixture was extracted with diethyl ether (3×10 mL), washed with brine (1×10 mL), dried (MgSO$_4$) and concentrated to give a crude brown oil. The crude oil was purified by flash chromatography using 10% EtOAc in hexane to give the title compound (3.6 g, 80% yield) as a colorless oil:

$^1$HNMR (CDCl$_3$, 300 MHz) δ 6.98 (d, J=1.2 Hz, 1H), 6.86 (d, J=1.8 Hz, 2H), 5.65 (t, J=6.9 Hz, 1H), 4.14 (d, J=6.9 Hz, 2H), 2.84–2.94 (m, 2H), 1.29 (s, 3H), 1.27 (s, 6H), 1.25 (S, 6H), 0.86 (s, 9H), 0.00 (s, 6H).

(±)-[(R)-3-(tert-Butyl-dimethyl-silanyloxymethyl)-2-(3,5-diisopropyl-phenyl-2-methyl-cyclopropyl]-methanol (Intermediate 37) and (±)-[(S)-3-(tert-Butyl-dimethyl-silanyloxymethyl)-2-(3,5-diisopropyl-phenyl)-2-methyl-cyclopropyl]-methanol (Intermediate 38)

Ethyl diazoacetate (5 mL, 48 mmol) in 10 mL of benzene was added slowly with a syringe pump (2 ml/h) to a solution of Intermediate 36 (0.7 g, 2 mmol) and anhydrous copper (II) sulfate (60 mg, 376 μmol) in 30 mL of benzene (30 mL) at 80° C. After completion of the addition of ethyl diazoacetate, the mixture was allowed to stir for 16 h at room temperature in order to decompose the excess of ethyl diazoacetate. The solvent was then evaporated under reduced pressure and the residue was purified by flash chromatography using 2% EtOAc in hexane to yield 1.2 g of a mixture of crude cyclopropyl esters, which was then dissolved in 15 mL of anhydrous THF and cooled to −78° C. with a dry ice/acetone bath. To this solution was added di-iso-butyl aluminum hydride (DEBAL-H) in hexane (1M, 10 mL, 10 mmol). After stirring at −78° C. for 2 h, the reaction was quenched with saturated NH$_4$Cl (2 mL). Celite (2 g) and diethyl ether (50 mL) were then added to the mixture and stirring was continued at 0° C. until all aluminum salt precipitated out. Inorganic material was removed by filtration, and solvents were removed under reduced pressure to give a brown oil, which was purified by flash chromatography using 20% EtOAc in hexane to obtain Intermediate 37 (154 mg, 20% yield) and Intermediate 38 (160 mg, 21% yield) as colorless oil:

$^1$HNMR for Intermediate 37: (CDCl$_3$, 300 MHz) δ 6.84 (s, 1H), 6.64 (s, 2H), 4.09 (dd, J=5.4 Hz, 11.7H, 1H), 3.90–3.92 (m, 1H), 3.14 (q, J=11.1 Hz, 2H), 2.75–2.82 (m, 2H), 1.40–1.48 (m, 21), 1.26 (s, 3H), 1.18 (s, 6h), 1.15 (s, 6H), 0.82 (s, 9H), 0.17 (d, J=15.6 Hz, 6H);

$^1$HNMR for Intermediate 38: (CDCl$_3$, 300 MHz) δ 7.00 (s, 2H), 6.96 (s, 1H), 3.85–3.89 (m, 2H), 3.47–3.53 (m, 1H), 3.06–3.13 (m, 1H), 2.86–2.95 (m, 2H), 1.42 (s, 3H), 1.07–1.13 (m, 1H), 0.97–0.93 (m, 1H), 0.90 (s, 9H), 0.00 (d, J=2.1 Hz, 6H).

(±)-[(R)-3-Methoxymethyl-2-methyl-2-(3,5-diisopropyl-phenyl)-cyclopropyl]-methanol (Intermediate 39)

Sodium hydride(40 mg, 1.52 mmol) was added slowly to a solution of Intermediate 37 (50 mg, 0.38 mmol) in 5 mL of DMF at 0° C. After stirring for 10 min, methyl iodide (0.100 mL, 1.52 mmol) was added to the mixture, which was then stirred at room temperature for 16 h. The reaction was quenched with saturated NH$_4$Cl, extracted with diethyl ether (3×10 mL), washed with brine (1×10 mL), dried (Na$_2$SO$_4$) and concentrated to give a crude brown oil. Purification by flash chromatography using 5% EtOAc in hexane afforded the methylated intermediate (136 mg, 87% yield) as a colorless oil, which was then dissolved in 5 mL of anhydrous THF and cooled to 0° C. with an ice bath. To this solution was added TBAF in THF (1M, 0.5 mL, 0.5 mmol) and the reaction mixture was allowed to stir at room temperature for 2 h. The reaction was finally quenched with water, extracted with ether (3×10 mL), washed with brine (1×10 mL), dried (Na$_2$SO$_4$) and concentrated to, give a crude colorless oil. Purification by flash chromatography using 20% EtOAc in hexane gave Intermediate 39 (100 mg, 100% yield) as a colorless oil:

$^1$HNMR (CDCl$_3$, 300 MHz) δ 6.91 (s, 1H), 6.72 (s, 2H), 3.98 (dd, J=4.5 Hz, 12 Hz, 1H), 3.78 (dd, J=5.4 Hz, 10.2 Hz, 1H), 3.31 (s, 3H), 2.96–3.14 (m, 2H), 2.79–2.88 (m, 2H), 1.40–1.50 (m, 2H), 1.33 (s, 3H), 1.24 (s, 6H), 1.21 (s, 6H).

(±)-[(S)-3-Methoxymethyl-2-methyl-2-(3,5-diisopropyl-phenyl)-cyclopropyl]-methanol (Intermediate 40a)

Following a procedure similar to that for the preparation of Intermediate 39 but using Intermediate 38 as the starting material yielded the title compound (35 mg, 48% yield) as a colorless oil:

$^1$HNMR (CDCl$_3$, 300 MHz) δ 7.00 (d, J=1.8 Hz, 1H), 6.96 (s, 1H) 3.55–3.65 (m, 2H), 3.42 (s, 3H), 3.30–3.40 (m, 1H), 3.18–3.22 (m, 1H), 1.80–2.15 (m, 2H), 1.40 (s, 3H), 1.25 (s, 6H), 1.22 (s, 6H).

(±)-[(S)-3-Ethoxymethyl-2-methyl-2-(3,5-diisopropyl-phenyl)-cyclopropyl]-methanol (Intermediate 40b)

Following a procedure similar to that for the preparation of Intermediate 39 but using Intermediate 38 as the starting material and ethyl iodide as alkylating reagent yielded the title compound (89 mg, 77% yield) as a colorless oil:

$^1$HNMR(CDCl$_3$, 300 MHz) δ 6.88 (d, J=1.8 Hz, 2H), 6.82 (d, J=1.5 Hz, 1H), 3.45–3.85 (m, 4H), 3.24–3.30 (m, 1H), 3.05–3.08 (m, 1H), 2.72–2.81 (m, 2H), 1.25–1.38 (m, 4H), 1.15 (s, 6H), 1.13 (s, 6H), 1.00–1.12 (m, 1H).

(1S, 2R, 3R)-3-Methoxymethyl-2-methyl-2-(3,5-diisopropyl-phenyl)-cyclopropylmethyl 4,7,7-trimethyl-3-oxo-2-oxa-bicyclo[2.2.1]heptane-1-carboxylate (Intermediate 41) and (1R, 2S, 3S)-3-Methoxymethyl-2-methyl-2-(3,5-diisopropyl-phenyl)-cyclopropylmethyl 4,7,7-trimethyl-3-oxo-2-oxa-bicyclo[2.2.1]heptane-1-carboxylate (Intermediate 42)

1-(S)-(−)-Camphanic chloride (118 mg, 0.55 mmol) and N,N-dimethylaminopyridine (80 mg, 0.66 mmol) were added to a solution of Intermediate 39 (100 mg, 0.34 mmol) in 5 mL of dichloromethane. After stirring at room temperature for 16 h, the mixture was extracted with dichloromethane (2×10 mL), washed with water (1×10 mL), dried (Na$_2$SO$_4$) and concentrated to give a crude colorless oil. Purification by column chromatography using 10% EtOAc in hexane afforded a mixture of the title compounds in 1:1 ratio (150 mg, 94% yield). Separation of this mixture with normal phase HPLC (Whatman, Partisil-10-PAC HPLC column) using 8% EtOAc in hexane as eluent provided Intermediate 41 (60 mg, 38% yield) and Intermediate 42 (59 mg, 38% yield) as colorless oils:

$^1$HNMR for Intermediate 41: (CDCl$_3$, 300 MHz) δ 6.98 (s, 2H), 6.94 (s 1H), 4.30–4.36 (m, 1H), 3.91–3.97 (m, 1H), 3.18–3.36 (m, 5H), 2.80–2.89 (m, 1H), 2.41–2.50 (m, 1H), 1.88–2.09 (m, 2H), 1.63–1.74 (m, 1H), 1.28–1.44 (m, 5H), 1.24 (s, 6H), 1.22 (s, 6H), 1.12 (s, 3H), 1.08 (s, 3H), 0.98 (s, 3H);

$^1$HNMR for Intermediate 42: (CDCl$_3$, 300 MHz) δ 6.99 (s, 2H), 6.93 (s, 1H), 4.26–4.32 (m, 1H), 3.92–3.99 (m, 1H), 3.20–3.33 (m, 5H), 2.80–2.90 (m, 2H), 2.39–2.48 (m, 1H), 1.87–2.07 (m, 2H), 1.55–1.74 (m, 1H), 1.39–1.46 (m, 5H), 1.37 (s, 3H), 1.25 (s, 6H), 1.22 (s, 3H), 1.12 (s, 3H), 1.06 (s, 3H), 0.99 (s, 3H).

(1S, 2R, 3S)-3-Methoxymethyl-2-methyl-2-(3,5-diisopropyl-phenyl)-cyclopropylmethyl 4,7,7-trimethyl-3-oxo-2-oxa-bicyclo[2.2.1]heptane-1-carboxylate (Intermediate 43a) and (1R, 2S, 3R)-3-Methoxymethyl-2-methyl-2-(3,5-diisopropyl-phenyl)-cyclopropylmethyl 4,7,7-trimethyl-3-oxo-2-oxa-bicyclo[2.2.1]heptane-1-carboxylate (Intermediate 44a)

Following a procedure similar to that for the preparation of Intermediates 41 and 42 but using Intermediate 40a as the starting material and using 10% EtOAc in hexane as normal phase HPLC eluent afforded Intermediate 43a (25 mg, 45% yield) and Intermediate 44a (23 mg, 41% yield) as colorless oils:

$^1$HNMR for Intermediate 43a: (CDCl$_3$, 300 MHz) δ 6.93 (s, 3H), 3.98–4.05 (m, 1H) 3.74–3.81 (m, 1H), 3.41–3.63 (m, 2H), 3.40 (s, 3H), 2.79–2.89 (m, 2H), 2.37–2.45 (m, 1H), 1.91–2.05 (m, 2H), 1.62–1.72 (m, 1H), 1.50–1.54 (m, 1H), 1.39 (s, 3H), 1.23 (s, 6H), 1.21 (s, 6H), 1.10 (s, 3H), 1.05 (s, 3H) 0.94 (s, 3H);

$^1$HNMR for Intermediate 44a: (CDCl$_3$, 300 MHz) δ 6.94 (s, 2H), 6.92 (s, 1H), 3.95–4.01 (m, 1H), 3.76–3.82 (m, 1H), 3.50–3.63 (m, 4H), 3.41 (s, 3H), 2.89–2.89 (m, 2H), 2.33–2.43 (m, 1H), 1.85–2.02 (m, 2H), 1.63–1.72 (m, 1H), 1.46–1.53 (m, 1H), 1.39 (s, 3H), 1.24 (s, 6H), 1.21 (s, 6H), 1.11 (s, 3H), 1.04 (s, 3H), 0.97 (s, 3H).

(1S, 2R, 3S)-3-Ethoxymethyl-2-methyl-2-(3,5-diisopropyl-phenyl)-cyclopropylmethyl 4,7,7-trimethyl-3-oxo-2-oxa-bicyclo[2.2.1]heptane-1-carboxylate (Intermediate 43b) and (1R, 2S, 3R)-3-Ethoxymethyl-2-methyl-2-(3,5-diisopropyl-phenyl)-cyclopropylmethyl 4,7,7-trimethyl-3-oxo-2-oxa-bicyclo[2.2.1]heptane-1-carboxylate (Intermediate 44b)

Following a procedure similar to that for the preparation of Intermediates 41 and 42 but using Intermediate 40b as the starting material, ethyl iodide as the alkylating reagent and using 10% EtOAc in hexane as normal phase HPLC eluent afforded Intermediate 43b (59 mg, 43% yield) and Intermediate 44b (56 mg, 41% yield) as colorless oils:

$^1$HNMR for Intermediate 43b: (CDCl$_3$, 300 MHz) δ 6.93 (d, J=1.5 Hz, 2H), 6.92 (d, J=1.2 Hz, 1H), 3.99–4.05 (m, 1H), 3.74–3.81 (m, 1H), 3.52–3.63 (m, 4H), 2.80–2.89 (m, 2H), 2.37–2.46 (m, 1H), 1.86–2.05 (m, 2H), 1.62–1.72 (m, 1H), 1.47–1.56 (m, 1H), 1.39 (s, 3H), 1.23 (s, 6H), 1.21 (s, 6H), 1.10 (s, 3H), 1.05 (s, 3H), 0.94 (s, 3H);

$^1$HNMR for Intermediate 44b: (CDCl$_3$, 300 MHz) δ 6.94 (s, 2H), 6.91 (s, 1H), 3.94–4.00 (m, 1H), 3.76–3.84 (m, 1H), 3.55–3.62 (m, 4H), 2.82–2.89 (m, 2H), 2.35–2.38 (m, 1H), 1.86–2.03 (m, 2H), 1.67–1.70 (m, 1H), 1.56 (s, 3H), 1.48–1.52 (m, 1H), 1.38 (s, 3H), 1.24 (s, 6H), 1.21 (s, 6H), 1.21 (s, 6H), 1.11 (s,3H), 1.04 (s, 3H), 0.97 (s, 3H).

(+)-(1S, 2R, 3R)-3-Methoxymethyl-2-methyl-2-(3,5-diisopropyl-phenyl)-cyclopropanecarbaldehyde (Intermediate 45)

Potassium hydroxide solution (1N, 1 mL) was added to a solution of Intermediate 41 (26 mg, 0.056 mmol) in 4 mL of THF/MeOH (1:1) at room temperature. After stirring for an hour, the mixture was diluted with ethyl acetate (10 mL) and acidified with 1 mL of 1N HCl at 0° C. The organic layer was then washed with brine (1×5 mL), dried (Na$_2$SO$_4$) and concentrated. The residue was purified by flash chromatography using 20% EtOAc in hexane to give the corresponding alcohol (16 mg, 100% yield). This alcohol was subsequently dissolved in dichloromethane (5 mL) and acetonitrile (0.5 mL). To this solution was added molecular sieve (45 mg), 4-methylmorpholine N-oxide (23 mg, 0.40 mmol) and tetrapropylammonium perruthenate (5 mg, 0.01 mmol). After stirring at room temperature for 45 min, the solvent was then removed under reduced pressure and the residue was purified by flash chromatography using 10% EtOAc in hexane to obtain the title compound in optically pure form (15 mg, 99% yield) as a colorless oil:

$^1$HNMR (CDCl$_3$, 300 MHz) δ 8.8 (d, J=7.5 Hz 1H), 7.15–7.18 (m, 2H), 6.90 (dd, J=4 Hz, 14 Hz, 1H), 3.62–3.68 (m, 1H), 3.26–3.41 (m, 1H), 3.26 (s, 3H), 1.88–1.97 (m, 2H), 1.60 (s, 4H), 1.35 (s, 3H), 1.19 (s, 12H).

(−)-(1R, 2S, 3S)-3-Methoxymethyl-2-methyl-2-(3,5-diisopropyl-phenyl)-cyclopropanecarbaldehyde (Intermediate 46)

Following a procedure similar to that for the preparation of Intermediate 45 but using Intermediate 42 as the starting material afforded the title compound (14 mg, 92% yield) as a colorless oil:

$^1$HNMR (CDCl$_3$, 300 MHz) δ 8.8 (d, J=7.5 Hz, 1H), 7.15–7.18 (m, 2H), 6.90 (dd, J=4 Hz, 14 Hz, 1H), 3.62–3.68 (m, 1H), 3.26–3.41 (m, 1H), 3.26 (s, 3H), 1.88–1.97 (m, 2H), 1.60 (s, 4H), 1.35 (s, 3H), 1.19 (s, 12H).

(+)-(1S, 2R, 3S)-3-Methoxymethyl-2-methyl-2-(3,5-diisopropyl-phenyl)-cyclopropanecarbaldehyde (Intermediate 47a)

Following a procedure similar to that for the preparation of Intermediate 45 but using Intermediate 43a as the starting material afforded the title compound (16 mg, 95% yield) as a colorless oil:

$^1$HNMR (CDCl$_3$, 300 MHz) δ 8.37 (d, J=6.9 Hz, 1H), 6.90 (d, J=1.55 Hz, 2H), 6.88 (d, J=1.2 Hz, 1H), 3.60–3.65 (m, 1H), 3.47–3.53 (m, 1H), 3.37 (s, 3H), 2.83–2.74 (m, 2H), 2.32–2.39 (m, 1H), 1.68–1.72 (m, 1H), 1.40 (s, 3H), 1.16 (s, 6H), 1.14 (s, 6H).

(+)-(1S, 2R, 3S)-3-Ethoxymethyl-2-methyl-2-(3,5-diisopropyl-phenyl)-cyclopropanecarbaldehyde (Intermediate 47b)

Following a procedure similar to that for the preparation of Intermediate 45 but using Intermediate 43b as the starting material afforded the title compound (30 mg, 83% yield) as a colorless oil:

$^1$HNMR (CDCl$_3$, 300 MHz) δ 8.42 (d, J=7.2 Hz, 1H), 6.97 (d, J=1.5 Hz, 2H), 6.94 (d, J=1.2 Hz, 1H), 3.54–3.73 (m, 4H), 2.80–2.90 (m, 2H), 2.39–2.45 (m, 1H), 1.75–1.79 (m, 1H), 1.46 (s, 3H), 1.26 (t, J=7.2 Hz, 3H), 1.23 (s, 6H), 1.21 (s, 6H).

(−)-(1R, 2S, 3R)-3-Methoxymethyl-2-methyl-2-(3,5-diisopropyl-phenyl)-cyclopropanecarbaldehyde (Intermediate 48a)

Following a procedure similar to that for the preparation of Intermediate 45 but using Intermediate 44a as the starting material afforded the title compound (14 mg, 87% yield) as a colorless oil:

$^1$HNMR (CDCl$_3$, 300 MHz) δ 8.37 (d, J=6.9 Hz, 1H), 6.90 (d, J=1.5 Hz, 2H), 6.88 (d, J=1.2 Hz, 1H), 3.60–3.65 (m, 1H), 3.47–3.53 (m, 1H), 3.37 (s, 3H), 2.83–2.74 (m, 2H), 2.32–2.39 (m, 1H), 1.68–1.72 (m, 1H), 1.40 (s, 3H), 1.16 (s, 6H), 1.14 (s, 6H).

(−)-(1R, 2S, 3R)-3-Ethoxymethyl-2-methyl-2-(3,5-diisopropyl-phenyl)-cyclopropanecarbaldehyde (Intermediate 48b)

Following a procedure similar to that for the preparation of Intermediate 45 but using Intermediate 44b as the starting material afforded the title compound (39 mg, 98% yield) as a colorless oil:

$^1$HNMR (CDCl$_3$, 300 MHz) δ 8.42 (d, J=7.2 Hz, 1H), 6.97 (d, J=1.5 Hz, 2H), 6.94 (d, J=1.2 Hz, 1H), 3.54–3.73 (m, 4H), 2.80–2.90 (m, 2H), 2.39–2.45 (m, 1H), 1.75–1.79 (m, 1H), 1.46 (s, 3H), 1.26 (t, J=7.2 Hz, 3H), 1.23 (s, 6H), 1.21 (s, 6H).

Ethyl (+)-(1S, 2R, 3R)-5-[3-methoxymethyl-2-methyl-2-(3,5-diisopropyl-phenyl)-cyclopropyl]-3-methyl-penta-2E,4E-dienoate (Compound 24)

n-Butyl lithium in hexane (1.6 M, 0.56 mL, 0.89 mmol) was added to a solution of triethylphosphono-3-methyl-2E-butenoate (264 mg, 1.0 mmol) in 5 mL of THF and 3 mL of 1,3-dimethyl-3,4,5,6-tetrahydro-2(1H)-pyrimidinone (DMPU) at −78° C. After stirring for 5 min, a solution of Intermediate 45 (15 mg, 0.20 mmol) in 1 mL of TF was added by cannulation. The resulting solution was stirred at −7° C. for 2 h and then quenched with saturated NH$_4$Cl. The mixture was then extracted with diethyl ether (3×5 mL), washed with brine (1×10 mL), dried (Na$_2$SO$_4$) and concentrated to give a crude colorless oil. Purification by column chromatography using 5%. EtOAc in hexane afforded the title compound (20 mg, 85% yield) as a white solid:

$^1$HNMR(CDCl$_3$, 300 MHz) δ 6.87 (s, 3H), 6.24 (d, J=15.6 Hz, 1H), 5.62 (s, 1H), 5.44 (dd, J=10.5 Hz, 15.3 Hz, 1H), 4.07 (q, J=6.9 Hz, 2H), 3.15–3.26 (m, 5H), 2.73–2.85 (m, 2H), 2.03 (s, 3H), 1.71–1.81 (m, 1H), 1.50–1.58 (m, 1H), 1.33 (s, 3H), 1.14–1.25 (m, 15H).

Ethyl (−)-(1R, 2S, 3S)-5-[3-methoxymethyl-2-methyl-2-(3,5-diisopropyl-phenyl)-cyclopropyl]-3-methyl-penta-2E,4E-dienoate (Compound 25)

Following a procedure similar to that for the preparation of Compound 24 but using Intermediate 46 as the starting material afforded the title compound (15 mg, 76% yield) as a white solid:

$^1$HNMR(CDCl$_3$, 300 MHz) δ 6.87 (s, 3H), 6.24 (d, J=15.6 Hz, 1H), 5.62 (s, 1H), 5.44 (dd, J=10.5 Hz, 15.3 Hz, 1H), 4.07 (q, J=6.9 Hz, 2H), 3.15–3.26 (m, 5H), 2.73–2.85 (m, 2H), 2.03 (s, 3H), 1.71–1.81 (m, 1H), 1.50–1.58 (m, 1H), 1.33 (s, 3H), 1.14–1.25 (m, 15H).

Ethyl (+)-(1S, 2R, 3S)-5-[3-methoxymethyl-2-methyl-2-(3,5-diisopropyl-phenyl)-cyclopropyl]-3-methyl-penta-2E,4E-dienoate (Compound 26a)

Following a procedure similar to that for the preparation of Compound 24 but using Intermediate 47a as the starting material afforded the title compound (19 mg, 85% yield) as a white solid:

$^1$HNMR (CDCl$_3$, 300 MHz) δ 6.83 (d, J=1.5 Hz, 1H), 6.82 (d, J=1.5 Hz, 2H), 6.10 (d, J=15.5 Hz, 1H), 5.55 (s, 1H); 5.18 (dd, J=10 Hz, 16 Hz, 1H), 4.07 (q, J=7.0 Hz, 2H), 3.53–3.60 (m, 2H), 3.36 (s, 3H), 2.74–2.80 (m, 2H), 1.92 (s, 3H), 1.60–1.62 (m, 1H), 1.50–1.59 (m, 1H), 1.36 (s, 3H), 1.21 (t, J=7.5 Hz, 3H), 1.15 (s, 6H), 1.13 (s, 1H).

Ethyl (+)-(1S, 2R, 3S)-5-[3-ethoxymethyl-2-methyl-2-(3,5-diisopropyl-phenyl)-cyclopropyl]-3-methyl-penta-2E,4E-dienoate (Compound 26b)

Following a procedure similar to that for the preparation of Co pound 24 but using Intermediate 47b as the starting material afforded the title compound (37 mg, 90% yield) as a white solid:

$^1$HNMR (CDCl$_3$, 300 MHz) δ 6.83 (s, 3H), 6.10 (d, J=15.3 Hz, 1H), 5.55 (s, 1H), 5.18 (dd, J=10 Hz, 16 Hz, 1H), 4.07 (q, J=7.0 Hz, 2H), 3.61 (d, J=6.9 Hz, 2H), 3.45–3.59 (m, 2H), 2.73–2;82 (m, 2H), 1.92 (s, 3H), 1.60–1.62 (m, 1H), 1.5–1.59 (m, 1H), 1.36 (s, 3H), 1.21 (t, J=7.0 Hz, 3H), 1.15 (s, 6H), 1.13 (s, 6H).

Ethyl (−)-(1R, 2S, 3R)-5-[3-methoxymethyl-2-methyl-2-(3,5-diisopropyl-phenyl)-cyclopropyl]-3-methyl-penta-2E,4E-dienoate (Compound 27a)

Following a procedure similar to that for the preparation of Compound 24 but using Intermediate 48a as the starting material afforded the title compound (14 mg, 73% yield) as a white solid:

$^1$HNMR (CDCl$_3$, 300 MHz) δ 6.83 (d, J=1.5 Hz, 1H), 6.82 (d, J=1.5 Hz, 2H), 6.10 (d, J=15.5 Hz, 1H), 5.55 (s, 1H), 5.18 (dd, J=10 Hz, 16 Hz, 1H), 4.07 (q, J=7.0 Hz, 2H), 3.53–3.60 (m, 2H), 3.36 (s, 3H), 2.74–2.80 (m, 2H), 1.92 (s, 3H), 1.60–1.62 (m, 1H), 1.50–1.59 (m, 1H), 1.36 (s, 3H), 1.21 (t, J=7.5 Hz, 3H), 1.15 (s, 6H), 1.13 (s, 6H).

Ethyl (−)-(1R, 2S, 3R)-5-[3-ethoxymethyl-2-methyl-2-(3,5-diisopropyl-phenyl)-cyclopropyl]-3-methyl-penta-2E,4E-dienoate (Compound 27b)

Following a procedure similar to that for the preparation of Compound 24 but using Intermediate 48b as the starting material afforded the title compound (36 mg, 73% yield) as a white solid:

$^1$HNMR (CDCl$_3$, 300 MHz) δ 6.83 (s, 3H), 6.10 (d, J=15.3 Hz, 1H), 5.55 (s, 1H), 5.18 (dd, J=10 Hz, 16 Hz, 1H), 4.07 (q, J=7.0 Hz, 2H), 3.61 (d, J=6.9 Hz, 2H), 3.45–3.59 (m, 2H), 2.73–2.82 (m, 2H), 1.92 (s, 3H), 1.60–1.62 (m, 1H), 1.50–1.59 (m, 1H), 1.36 (s, 3H), 1.21 (t, J =7.0 Hz, 3H), 1.15 (s, 6H), 1.13 (s, 6H).

(+)-(1S, 2R, 3R)-5-[3-Methoxymethyl-2-methyl-2-(3,5-diisopropyl-phenyl)-cyclopropyl]-3-methyl-penta-2E,4E-dienoic acid (Compound 28)

Sodium hydroxide solution (1N, 1 mL) was added to a solution of Compound 24 (20 mg, 0.05 mmol) in 4 mL of THF/MeOH (1:1) at 50° C. After stirring at 50° C. for 16 h, the mixture was diluted with ethyl acetate (10 mL) and acidified with 1 mL of 1 HCl at 0° C. The organic layer was then washed with brine (1×5 mL), dried ($Na_2SO_4$) and concentrated. The residue was purified by flash chromatography using 30% EtOAc in hexane to give the title compound (17 mg, 91% yield) as a white solid:

$^1$HNMR ($CDCl_3$, 300 MHz) δ 6.94 (s, 3H), 6.35 (d, J=15.6 Hz, 1H ), 5.71 (s, 1H), 5.66 (dd, J=10.5 Hz, 15.3 Hz, 1H), 3.23–3.32 (m, 5H), 2.80–2.88 (m, 2H), 2.10 (s, 3H), 1.82–1.92 (m, 1H), 1.63–1.65 (m, 1H), 1.41 (s, 3H), 1.24 (s, 6H), 1.2 (s, 6H).

(−)-(1R, 2S, 3S)-5-[3-Methoxymethyl-2-methyl-2-(3,5-diisopropyl-phenyl)-cyclopropyl]-3-methyl-penta-2E,4E-dienoic acid (Compound 29)

Following a procedure similar to that for the preparation of Compound 28 but using Compound 25 as the starting material afforded the title compound (10 mg, 73% yield) as a white solid:

$^1$HNMR ($CDCl_3$, 300 MHz) δ 6.94 (s, 3H), 6.35 (d, J=15.6 Hz, 1H), 5.71 (s, 1H), 5.66 (dd, J=10.5 Hz, 15.3 Hz, 1H), 3.23–3.32 (m, 5H), 2.80–2.88 (m, 2H), 2.10 (s, 3H), 1.82–1.92 (m, 1H), 1.63–1.65 (m, 1H), 1.41 (s, 3H), 1.24 (s, 6H), 1.21 (s, 6H).

(+)-(1s, 2R, 3S)-5-[3-Methoxymethyl-2-methyl-2-(3,5-diisopropyl-phenyl)-cyclopropy]-3-methyl-penta-2E,4E-dienoic Acid (Compound 30a)

Following a procedure similar to that for the preparation of Compound 28 but using Compound 26a as the starting material afforded the title compound (8 mg, 47% yield) as a white solid:

$^1$HNMR ($CDCl_3$, 300 MHz) δ 6.83 (d, J=1.5 Hz, 1H), 6.82 (d, J=1.5 Hz, 2H), 6.12 (d, J=15.6 Hz, 1H), 5.57 (s, 1H), 5.26 (dd, J=9.6 Hz 15.6 Hz, 1H), 3.58 (d, J=7.2 Hz, 2H), 3.36 (s, 3H), 2.73–2.82 (m, 2H), 1.92 (s, 3H), 1.60–1.66 (m, 1H), 1.49–1.52 (m, 1H), 1.36 (s, 3H), 1.15 (s, 61H), 1.13 (s, 6H).

(+)-(1S, 2R, 3S)-5-[3-Ethoxymethyl-2-methyl-2-(3,5-diisopropyl-phenyl)-cyclopropyl]-3-methyl-penta-2E,4E-dienoic acid (Compound 30b)

Following a procedure similar to that for the preparation of Compound 28 but using Compound 26b as the starting material afforded the title compound (29 mg, 84% yield) as a white solid:

$^1$HNMR ($CDCl_3$, 300 MHz) δ 6.90 (d, J=1.5 Hz, 1H), 6.89 (d, J=1.5 Hz, 2H), 6.18 (d, J=15.5 Hz, 1H), 5.63 (s, 1H), 5.29 (dd, J=9.6 Hz, 15.6 Hz, 1H), 3.65–3.73 (m, 2H), 3.54–3.63 (m, 2H), 2.81–2.87 (m, 2H), 1.98 (s, 3H), 1.70–1.72 (m, 1H), 1.57–1.68 (m, 1H), 1.43 (s, 3H), 1.28 (t, J=7 Hz, 3H), 1.22 (m, 6H), 1.20 (s, 6H).

(−)-(1R, 2S, 3R)-5-[3-Methoxymethyl-2-methyl-2-(3,5-diisopropyl-phenyl)-cyclopropyl]-3-methyl-penta-2E,4E-dienoic acid (Compound 31a)

Following a procedure similar to that for the preparation of Compound 28 but using Compound 27a as the starting material afforded the title compound (9 mg, 70% yield) as a white solid:

$^1$HNMR ($CDCl_3$, 300 MHz) δ 6.83 (d, J=1.5 Hz, 1H), 6.82 (d, J=1.5 Hz, 2H), 6.12 (d, J=15.6 Hz, 1H), 5.57 (s, 1H), 5.26 (dd, J=9.6 Hz, 15.6 Hz, 1H), 3.58 (d, J=7.2 Hz, 2H), 3.36 (s, 31), 2.73–2.82 (m, 2H), 1.92 (s, 3H), 1.60–1.66 (m, 1H), 1.49–1.52 (m, 1H), 1.36 (s, 3H), 1.15 (s, 6H), 1.13 (s, 6H).

(−)-(1R, 2S, 3R)-5-[3-Ethoxymethyl-2methyl-2-(3,5-diisopropyl-phenyl)-cyclopropyl]-3-methyl-penta-2E,4E-dienoic acid. (Compound 31b)

Following a procedure similar to that for the preparation of Compound 28 but using Compound 27b as the starting material afforded the title compound (28 mg, 85% yield) as a white solid:

$^1$HNMR ($CDCl_3$, 300 MHz) δ 6.90 (d, J=1.5 Hz, 1H), 6.89 (d, J=1.5 Hz, 2H), 6.18 (d, J=15.5 Hz, 1H), 5.63 (s, 1H), 5.29 (dd, J=9.6 Hz, 15.6 Hz, 1H), 3.65–3.73 (m, 2H), 3.54–3.63 (m, 2H), 2.81–2.87 (m, 2H), 1.98 (s, 3H), 1.70–1.72 (m, 1H), 1.57–1.68 (m, 1H), 1.43 (s, 3H), 1.28 (t, J=7 Hz, 3H), 1.22 (m, 6H), 1.20 (s, 6H).

Biological Activity, Modes of Administration

It has been discovered in accordance with the present invention that compounds of this invention are capable of significantly reducing serum glucose levels and reducing or maintaining serum triglyceride levels in diabetic mammals, without the undesirable side effects of reducing serum thyroxine levels (hypothyroidism) and transiently raising triglyceride levels (hypertriglyceridemia). The compounds of the invention were tested in certain assays for activity as agonists of RAR and RXR retinoid receptors. These assays demonstrated that the compounds of the invention are partial agonists of the RXR receptors.

Specifically, one such assay is a chimeric receptor transactivation assay which tests for agonist-like activity in the $RAR_\alpha$, $RAR_\beta$ and $RAR_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the, chimeric receptor transactivation assay. The results of the ligand binding assay are expressed in $K_i$ numbers. (See Cheng et al. Biochemical Pharmacology Vol. 22 pp 3099–3108, expressly incorporated herein by reference.)

Efficacy in a transactivation assay is expressed as a percentage of the maximum potency attained by the compound compared to a standard which, in this, case, is the compound named (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. This standard compound is described in U.S. Pat. No. 6,114,533.

Table 1 discloses the activity of certain exemplary tetrahydronaphthale compounds of the invention in the above-described RXR receptor transactivation and binding assays. In the chimeric receptor transactivation assay the compounds were essentially inactive in activating $RAR_\alpha$, $RAR_\beta$ and $RAR_\gamma$ receptors and these data are not shown. The transactivation data pertaining to the activation of RXR receptors were obtained in the holoreceptor assay.

TABLE 1

| Compound # | Structure | Binding (nM) | | | Transactivation (nM) (% Efficiency) | | |
| --- | --- | --- | --- | --- | --- | --- | --- |
| | | α | β | γ | α | β | γ |
| 23a (−) | | 18 | 188 | ND | 27 (9) | 546 (9) | 60 (9) |
| 21a (−) | | 5 | 48 | ND | 4 (39) | 36 (38) | 6 (41) |
| 23b (−) | | 27 | 121 | ND | NA | NA | NA |
| 21b (−) | | 17 | 227 | ND | 28 (41) | >1k | 44 (34) |

Note:
NA = Not Active;
ND = Not Determined

Table 2 discloses the activity of certain exemplary phenyl compounds of the invention in the above-described RXR receptor transactivation and binding assays. In the chimeric receptor transactivation assay the compounds were essentially inactive in activating $RAR_\alpha$, $RAR_\beta$ and $RAR_\gamma$ receptors and these data are not shown.

TABLE 2

| Compound # | Structure | Binding (nM) α | β | γ | Transactivation (nM) (% Efficiency) α | β | γ |
|---|---|---|---|---|---|---|---|
| 29 (−) | (structure: 3,5-diisopropylphenyl cyclopropyl with OMe, H, and HOOC-diene substituents) | 11 | 49 | ND | 5 (24) | 47 (34) | 16 (35) |
| 31a (−) | (structure: 3,5-diisopropylphenyl cyclopropyl with OMe, H, and HOOC-diene substituents) | 7.6 | 25 | ND | 2.7 (104) | 17 (90) | 3.6 (101) |
| 31b (−) | (structure: 3,5-diisopropylphenyl cyclopropyl with OMe, H, and HOOC-diene substituents) | 24 | 96 | ND | 48 (45) | >3K | 4482 (39) |

Note:
NA = Not Active;
ND = Not Determined

In Tables 1 and 2 the binding $K_i$ numbers are indicated in the first 3 columns. In the second set of three columns the numbers in parentheses indicate efficacy as a percentage compared to the standard compound, (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid and the other numbers indicate the measured $EC_{50}$ in nanomolar concentration.

An assay described below tests the effect of compounds of the invention on serum glucose, tryglyceride and thyroxine levels in female 9–10 weeks old db/db mice.

Description of Assay.

Female diabetic db/db (9–10 weeks old) mice were maintained on standard laboratory food and treated by oral gavage with vehicle (corn oil), standard compound (2E, 4E, 1'S, 2S)-3-methyl-5-[2'-methyl-2'-(5,5,8,8-tetramethyl-5,6,7,8-tetrahydro-naphthalen-2-yl)-cyclopropyl]-penta-2,4-dienoic acid (5 mg/kg) or the test compound (5–100 mg/kg, as described in Table 2) daily for seven days at 8:00 AM. Blood samples (70 µl) were taken by orbital bleeding at 11:00 AM on day 0 (pre-treatment), day 3, and day 6. On day 7, a blood sample (700 µl) was taken at 11:00 AM and the animals were sacrificed. Glucose, triglyceride and thyroxine (T4) levels were determined on a Boehringer Manheim Hatachi Clinical Chemistry Analyzer using standard protocols provided by the manufacturer and reagents that were supplied in commercially available kits (glucose and T4: Boehringer Manheim; triglycerides: Roche Diagnostics). Seven animals were treated in each group. The results of the assays are summarized in Table 3.

TABLE 3

| Treatment | Glucose (mg/dl) | | | Triglycerides (mg/dl) | | | T4 (µg/dL) |
|---|---|---|---|---|---|---|---|
| (dose) | Day 0 | Day 3, 3 h | Day 6, 3 h | Day 0 | Day 3, 3 h | Day 6, 3 h | Day 7 |
| Vehicle (Corn oil) | 478 ± 141 | 449 ± 64 | 569 ± 94 | 240 ± 102 | 326 ± 69 | 393 ± 116 | 3.3 ± 0.4 |
| Standard compound (4 mg/kg) | 423 ± 57 | 315 ± 105 | 268 ± 242 | 300 ± 76 | 219 ± 80 | 117 ± 22 | 1.1 ± 0.2 |
| Compound 21a (50 mg/kg) | 445 ± 66 | 339 ± 194 | 314 ± 196 | 271 ± 80 | 130 ± 71 | 180 ± 63 | 4.2 ± 0.3 |

As the data indicate, the compounds of the invention not only cause significant decrease in serum glucose levels and maintain, or reduce triglyceride levels in diabetic mammals, but in contrast with the prior art standard compound (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid do not have the undesirable side effect of reducing serum thyroxine levels.

Modes of Administration, Dosing

To treat diabetic mammals, including humans for the purpose of reducing serum glucose levels in said mammals a pharmaceutical composition containing one or more compound of the invention is administered to the mammal in daily doses in the range of 1 to 100 mg per kg bodyweight of the mammal. Preferably the daily dose is between 10 to 50 mg per kg body weight of the mammal.

Generally speaking the compounds of the invention are also useful for preventing or treating diseases and conditions that are responsive to compounds that promote the expression of or bind to receptors belonging to the steroid or thyroid receptor superfamily. More specifically the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age, and photo damage to the skin. The compounds are also useful for the prevention and treatment of metabolic diseases and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, heoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions, and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

To treat diabetes the compounds of this invention are preferably administered, orally.

For the prevention or treatment of other diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the co pound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

What is claimed is:

1. A compound of the formula

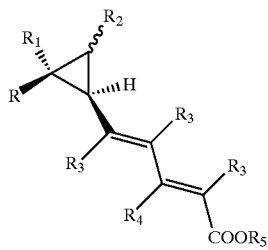

where a wavy line represents a bond in the up or in the down configuration, a dashed arrow represents a bond in the down configuration, a solid arrow represents a bond in the up configuration, $R_1$ is H, methyl, or ethyl, fluoro-substituted methyl or fluoro-substituted ethyl;

$R_2$ is normal alkyl of 1 to 4 carbons, fluoro-substituted normal alkyl of 1 to 4 carbons, $CH_2OCH_3$, $CH_2$—O—$CH_2$—$CH_3$, $CH_2$—O—$CH_2$—$OCH_3$, $CH_2$—$CH_2$—O—$CH_3$, $CH_2SCH_3$, $CH_2$—S—$CH_2$—$CH_3$, $CH_2$—S—$CH_2$—$OCH_3$, $CH_2$—$CH_2$—S—$CH_3$, $CH_2$—S—$CH_2$—S—$CH_3$, $CH_2$—O—$CH_2$—S—$CH_3$, $CH_2NHCH_3$, $CH_2$—NH—$CH_2$—$CH_3$, $CH_2$—NH—$CH_2$—$OCH_3$, $CH_2$—$CH_2$—NH—$CH_3$, $CH_2$—O—$CH_2$—$NHCH_3$;

$R_3$ is H or F;

$R_4$ is H, alkyl of 1 to 3 carbons;

$R_5$ is H, alkyl of 1 to 6 carbons, $CH_2OR_6$ or $CH_2OCOR_6$ where $R_6$ is alkyl of 1 to 3 carbons, and R is selected from the groups consisting of the radicals defined by formulas (a) and (b):

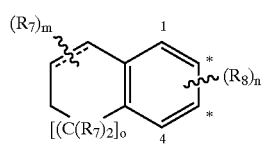

Formula (a)

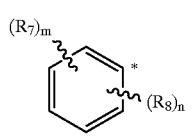

Formula (b)

where the dashed line in a ring represents a bond, or absence of a bond, a * denotes a ring carbon to which the pentadienoyl-cyclopropyl group is attached, with the proviso that the pentadienoyl-cyclopropyl group is attached to only one carbon on the ring;

m is an integer having the values 0 to 6;

n is an integer having the values 0 to 3;

o is an integer having the values 0 or 1;

$R_7$ is independently H, alkyl of 1 to 6 carbons, F, Cl, Br or I, and $R_8$ is independently H, alkyl of 1 to 6 carbons, F, Cl, Br, I, $OC_{1-6}$alkyl or $SC_{1-6}$alkyl.

2. A compound in accordance with claim 1 where $R_2$ is $CH_2OCH_3$ or $CH_2OCH_2CH_3$.

3. A compound in accordance with claim 1 where $R_7$ is alkyl of 1 to 6 carbons.

4. A compound in accordance with claim 1 where $R_8$ is H or alkyl of 1 to 6 carbons.

5. A compound in accordance with claim 1 where R is represented by formula (a).

6. A compound in accordance with claim 5 where the dashed line in formula (a) represents absence of a bond, and where o is one (1).

7. A compound in accordance with claim 6 where $R_2$ is $CH_2OCH_3$ or $CH_2OCH_2CH_3$.

8. A compound in accordance with claim 6 where $R_7$ is alkyl of 1 to 6 carbons.

9. A compound in accordance with claim 6 where $R_8$ is H or alkyl of 1 to 6 carbons.

10. A compound in accordance with claim 1 where R is represented by formula (b).

11. A compound in accordance with claim 10 where $R_2$ is $CH_2OCH_3$ or $CH_2OCH_2CH_3$.

12. A compound in accordance with claim 10 where $R_7$ is alkyl of 1 to 6 carbons.

13. A compound in accordance with claim 10 where $R_8$ is H or alkyl of 1 to 6 carbons.

14. A compound of the formula

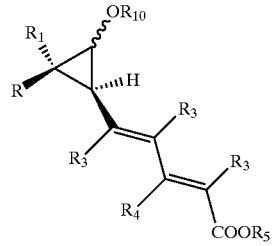

where a wavy line represents a bond in the up or in the down configuration, a dashed arrow represents a bond in the down configuration, a solid arrow represents a bond in the up configuration, $R_1$ is H, methyl, or ethyl, fluoro-substituted methyl or fluoro-substituted ethyl;

$R_{10}$ is $CH_3$, $CH_2$—$CH_3$, or $CH_2$—$OCH_3$, $R_3$ is H or F;

$R_4$ is H, alkyl of 1 to 3 carbons;

$R_5$ is H, alkyl of 1 to 6 carbons, $CH_2OR_6$ or $CH_2OCOR_6$ where $R_6$ is alkyl of 1 to 3 carbons, and R is selected from the groups consisting of the radicals defined by formulas (g) and (h)

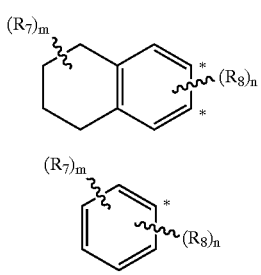

formula (g)

formula (h)

where a * denotes a ring carbon to which the pentadienoyl-cyclopropyl group is attached, with the proviso that the pentadienoyl-cyclopropyl group is attached to only one carbon on the ring;

m is an integer having the values 0 to 8;

n is an integer having the values 0 to 3;

$R_7$ is independently H, alkyl of 1 to 6 carbons, F, Cl, Br or I;

$R_8$ is independently H, alkyl of 1 to 6 carbons, F, Cl, Br, I, $OC_{1-6}$alkyl or $SC_{1-6}$alkyl, or a pharmaceutically acceptable salt of said compound.

15. A compound in accordance with claim 14 where R is represented by formula (g).

16. A compound in accordance with claim 15 where R is represented by the formula

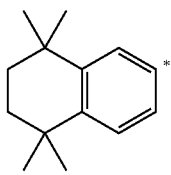

where the * denotes a ring carbon to which the pentadienoyl-cyclopropyl group is attached.

17. A compound in accordance with claim 14 where R is represented by the formula

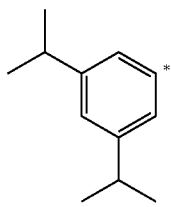

where the * denotes a ring carbon to which the pentadienoyl-cyclopropyl group is attached.

18. A compound of the formula

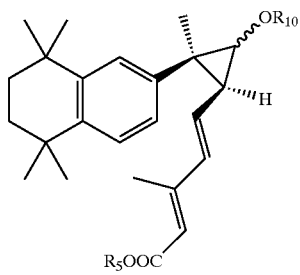

where a wavy line represents a bond in the up or in the down configuration, a dashed arrow represents a bond in the down configuration, a solid arrow represents a bond in the up configuration, $R_{10}$ is methyl or ethyl, and $R_5$ is H, alkyl of 1 to 6 carbons, $CH_2OR_6$ or $CH_2OCOR_6$ where $R_6$ is alkyl of 1 to 3 carbons, or a pharmaceutically acceptable salt of said compound.

19. A compound in accordance with claim 18 where the wavy line represents a bond in the up configuration.

20. A compound in accordance with claim 19 where $R_{10}$ is methyl.

21. A compound in accordance with claim 20 where $R_5$ is H, ethyl, or a pharmaceutically acceptable salt of said compound.

22. A compound in accordance with claim 19 where $R_{10}$ is ethyl.

23. A compound in accordance with claim 22 where $R_5$ is H, ethyl, or a pharmaceutically acceptable salt of said compound.

24. A compound in accordance with claim 18 where the wavy line represents a bond in the down configuration.

25. A compound in accordance with claim 24 where $R_{10}$ is methyl.

26. A compound in accordance with claim 25 where $R_5$ is H, ethyl, or a pharmaceutically acceptable salt of said compound.

27. A compound in accordance with claim 24 where $R_{10}$ is ethyl.

28. A compound in accordance with claim 27 where $R_5$ is H, ethyl, or a pharmaceutically acceptable salt of said compound.

29. A compound of the formula

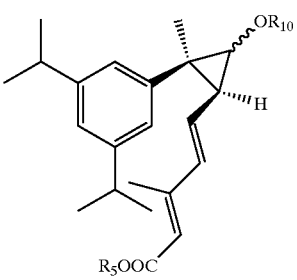

where a wavy line represents a bond in the up or in the down configuration, a dashed arrow represents a bond in the down configuration, a solid arrow represents a bond in the up configuration, $R_{10}$ is methyl or ethyl, and $R_5$ is H, alkyl of 1 to 6 carbons, $CH_2OR_6$ or $CH_2OCOR_6$ where $R_6$ is alkyl of 1 to 3 carbons, or a pharmaceutically acceptable salt of said compound.

30. A compound in accordance with claim 29 where the wavy line represents a bond in the up configuration.

31. A compound in accordance with claim 30 where $R_{10}$ is methyl.

32. A compound in accordance with claim 31 where $R_5$ is H, ethyl, or a pharmaceutically acceptable salt of said compound.

33. A compound in accordance with claim 30 where $R_{10}$ is ethyl.

34. A compound in accordance with claim 33 where $R_5$ is H, ethyl, or a pharmaceutically acceptable salt of said compound.

35. A compound in accordance with claim 20 where the wavy line represents a bond in the down configuration.

36. A compound in accordance with claim 35 where $R_{10}$ is methyl.

37. A compound in accordance with claim 36 where $R_5$ is H, ethyl, or a pharmaceutically acceptable salt of said compound.

38. A process for administering to a diabetic mammal to reduce the serum glucose level of said mammal a compound of the formula:

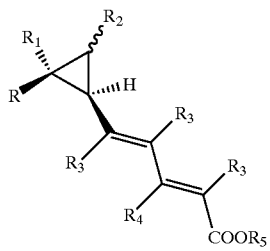

where a wavy line represents a bond in the up or in the down configuration,
a dashed arrow represents a bond in the down configuration,
a solid arrow represents a bond in the up configuration,
$R_1$ is H, methyl, or ethyl, fluoro-substituted methyl or fluoro-substituted ethyl;
$R_2$ is normal alkyl of 1 to 4 carbons, fluoro-substituted normal alkyl of 1 to 4 carbons, $CH_2OCH_3$, $CH_2$—O—$CH_2$—$CH_3$, $CH_2$—O—$CH_2$—$OCH_3$, $CH_2$—$CH_2$—O—$CH_3$, $CH_2SCH_3$, $CH_2$—S—$CH_2$—$CH_3$, $CH_2$—S—$CH_2$—$OCH_3$, $CH_2$—$CH_2$—S—$CH_3$, $CH_2$—S—$CH_2$—S—$CH_3$, $CH_2$—S—$CH_3$, $CH_2$—O—$CH_2$—S—$CH_3$, $CH_2NHCH_3$, $CH_2$—NH—$CH_2$—$CH_3$, $CH_2$—NH—$CH_2$—$OCH_3$, $CH_2$—$CH_2$—NH—$CH_3$, $CH_2$—O—$CH_2$—$NHCH_3$;
$R_3$ is H or F;
$R_4$ is H, alkyl of 1 to 3 carbons;
$R_5$ is H, alkyl of 1 to 6 carbons, $CH_2OR_6$ or $CH_2OCOR_6$ where $R_6$ is alkyl of 1 to 3 carbons, and
R is selected from the groups consisting of the radicals defined by formulas (a) and (b):

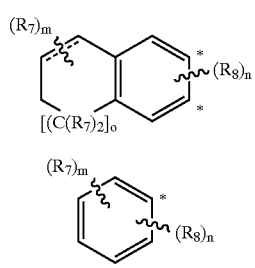

where the dashed line in a ring represents a bond, or absence of a bond,
a * denotes a ring carbon to which the pentadienoyl-cyclopropyl group is attached, with the proviso that the pentadienoyl-cyclopropyl group is attached to only one carbon on the ring;
m is an integer having the values 0 to 6;
n is an integer having the values 0 to 3;
o is an integer having the values 0 or 1;
$R_7$ is independently H, alkyl of 1 to 6 carbons, F, Cl, Br or I, and
$R_8$ is independently H, alkyl of 1 to 6 carbons, F, Cl, Br, I, $OC_{1-6}$alkyl or $SC_{1-6}$alkyl.

39. A process in accordance with claim 38 where the compound used in the process is in accordance with the formula

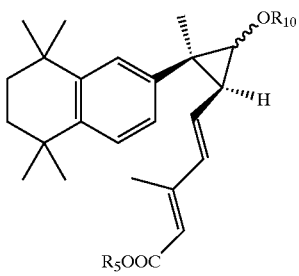

where $R_{10}$ is methyl or ethyl.

40. A process in accordance with claim 38 where the compound used in the process is in accordance with the formula:

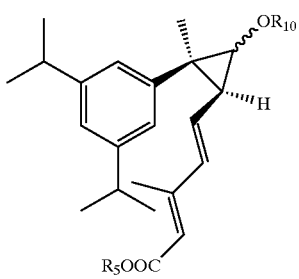

where $R_{10}$ is methyl or ethyl.

41. A compound of the formula:

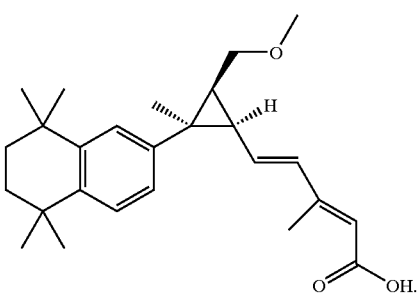

42. A process in accordance with claim 38 where the compound used has the formula:

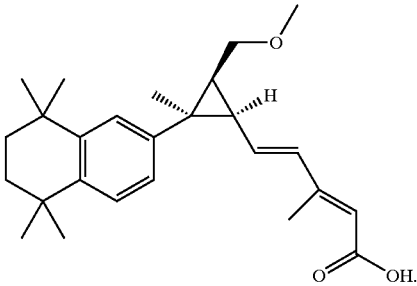

* * * * *

UNITED STATES PATENT AND TRADEMARK OFFICE
CERTIFICATE OF CORRECTION

PATENT NO. : 6,936,636 B2
DATED : August 30, 2005
INVENTOR(S) : Sinha et al.

It is certified that error appears in the above-identified patent and that said Letters Patent is hereby corrected as shown below:

Column 3,
Line 56, "X is Q" should be -- X is O --.
Line 66, "H alkyl" should be -- H, alkyl --.

Column 4,
Line 67, "group" should be -- group. --.

Column 12,
Line 22, "(UPLC)" should be -- (HPLC) --.

Column 13,
Formula 39, "m($R_7$)" should be -- ($R_7$)m --.

Column 29,
After Intermediate 3, "DIBAL-H, $CH_2C12$" should be -- DIBAL-H, $CH_2Cl_2$ --.

Column 35,
Compound 19a (+)($R_{10}$=Me), "Compound 19a (+)($R_{10}$=Me)" should be
-- Compound 19a (-)($R_{10}$=Me) --.

Column 35,
Compound 19b (+)($R_{10}$=Me), "Compound 19b (+)($R_{10}$=Et)" should be
-- Compound 19b (-)($R_{10}$=Et) --.

Column 38,
Intermediate 38, " " should be

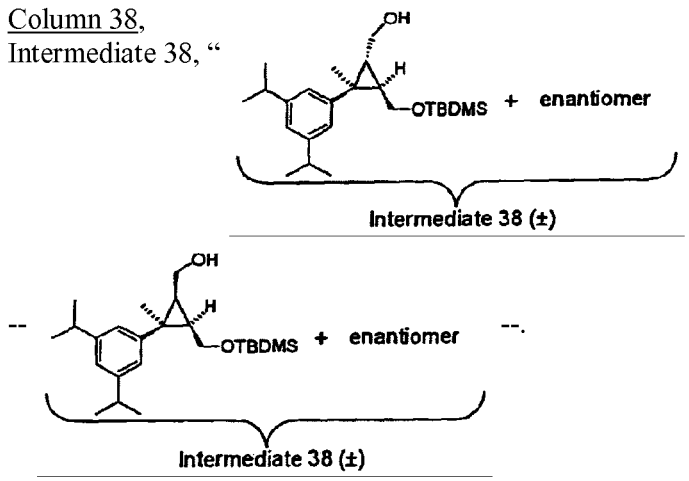

-- --.

UNITED STATES PATENT AND TRADEMARK OFFICE
CERTIFICATE OF CORRECTION

PATENT NO. : 6,936,636 B2  Page 2 of 3
DATED : August 30, 2005
INVENTOR(S) : Sinha et al.

It is certified that error appears in the above-identified patent and that said Letters Patent is hereby corrected as shown below:

Column 39,
Intermediate 40, " 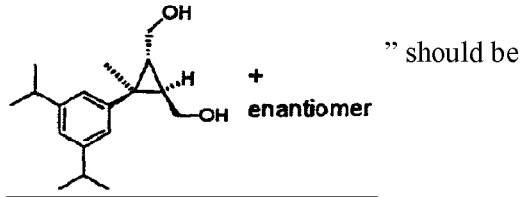 " should be

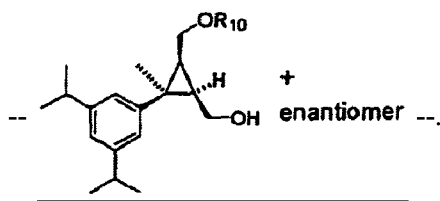 --.

Column 46,
Line 43, "This: colorless" should be -- This colorless --.
Line 56, , "1.0 Hz" should be -- 11.0 Hz --.

Column 47,
Line 28, "1.59 (s, 41)" should be -- 1.59 (s, 4H) --.

Column 48,
Line 54, "1.90-1.95 (m, 1)" should be -- 1.90-1.95 (m, 1H) --.

Column 49, -
Line 15, "2.33-2.42 (m, 1R)" should be -- 2.33-2.42 (m, 1H) --.
Line 41, "3.63-6.68" should be -- 3.62-6.68 --.

Column 50,
Line 58, "1.18 (s,6)" should be -- 1.18 (s,6H) --.

Column 55,
Line 1, "to give. Intermediate" should be -- to give Intermediate --.

Column 56,
Line 45, "to, give a crude" should be -- to give a crude --.

Column 59,
Line 5, "J=1.55 Hz" should be -- J=1.5 Hz --.
Line 57, "-7° C" should be -- -78° C --.

UNITED STATES PATENT AND TRADEMARK OFFICE
CERTIFICATE OF CORRECTION

PATENT NO. : 6,936,636 B2
DATED : August 30, 2005
INVENTOR(S) : Sinha et al.

It is certified that error appears in the above-identified patent and that said Letters Patent is hereby corrected as shown below:

Column 60,
Line 31, "Co pound" should be -- Compound --.

Column 61,
Line 40, "1.15 (s, 61H)" should be -- 1.15 (s, 6H) --.

Column 66,
Line 53, "2S)" should be -- 2'S) --.

Column 68,
Line 47, "co pound" should be -- compound --.

Column 72,
Line 64, "A compound in accordance with claim 20 where the wavy line represents a bond in the down configuration." should be -- A compound in accordance with claim 29 where the wavy line represents a bond in the down configuration. --.

Signed and Sealed this

Twenty-first Day of March, 2006

JON W. DUDAS
*Director of the United States Patent and Trademark Office*

Disclaimer

6,936,636—Santosh Sinha, Irvine, CA (US); Kwok Yin Tsang, Irvine, CA (US); Smita Bhat, Irvine, CA (US); Roshantha A. Chandraratna, Laguna Hills, CA (US). 5-[PHENYL-TETRAHYDRONAPHTHALEN-2-YL DIHYDRONAPHTHALENE-2YL AND HETEROARYL-CYCLOPROPYL]-PENTADIENOIC ACID DERIVATIVES HAVING SERUM GLUCOSE REDUCING ACTIVITY. Patent dated August 30, 2005. Disclaimer filed August 8, 2011, by the assignee, Allergan, Inc., Irvine, CA (US).

Hereby disclaims all of the claims 1-42 of said patent.

*(Official Gazette November 22, 2011)*